(12) United States Patent
Fan et al.

(10) Patent No.: US 10,358,668 B2
(45) Date of Patent: Jul. 23, 2019

(54) BIOLOGICAL PLATFORM FOR PRODUCTION OF COMMODITY CHEMICALS

(71) Applicant: The Regents of the University of California, Oakland, CA (US)

(72) Inventors: Zhiliang Fan, Davis, CA (US); Amanda Hildebrand, Davis, CA (US)

(73) Assignee: The Regents Of The University Of California, Oakland, CA (US)

( * ) Notice: Subject to any disclaimer, the term of this patent is extended or adjusted under 35 U.S.C. 154(b) by 0 days.

(21) Appl. No.: 15/307,803

(22) PCT Filed: Apr. 28, 2015

(86) PCT No.: PCT/US2015/028090
§ 371 (c)(1),
(2) Date: Oct. 28, 2016

(87) PCT Pub. No.: WO2015/168184
PCT Pub. Date: Nov. 5, 2015

(65) Prior Publication Data
US 2017/0044583 A1 Feb. 16, 2017

Related U.S. Application Data

(60) Provisional application No. 61/985,379, filed on Apr. 28, 2014.

(51) Int. Cl.
*C12P 19/12* (2006.01)
*C12N 9/42* (2006.01)
(Continued)

(52) U.S. Cl.
CPC .............. *C12P 19/12* (2013.01); *C07K 14/37* (2013.01); *C12N 9/0006* (2013.01); (Continued)

(58) Field of Classification Search
None
See application file for complete search history.

(56) References Cited

U.S. PATENT DOCUMENTS

2012/0129221 A1* 5/2012 Fan ........................... C12P 7/10
435/74

FOREIGN PATENT DOCUMENTS

WO 2012/138474 A1 10/2012
WO WO 2013/022594 * 2/2013

OTHER PUBLICATIONS

Beaudoin. The Biofilm-Specific Antibiotic Resistance Gene ndvB Is Important for Expression of Ethanol Oxidation Genes in Pseudomonas aeruginosa Biofilms. J. Bacteriol. Jun. 2012 , vol. 194, No. 12, 3128-3136.*

(Continued)

*Primary Examiner* — Yong D Pak
(74) *Attorney, Agent, or Firm* — Morrison & Foerster LLP

(57) ABSTRACT

The present disclosure generally relates to biological platforms for the conversion of cellulosic biomass into fuels and chemicals. More specifically, the present disclosure relates to the conversion of cellulosic materials into sugar acids or their salts, which may then be used to produce commodity chemicals. In one aspect, the present disclosure relates to a recombinant host cell including: reduced activity of one or more polypeptides having β-glucosidase activity as compared to a corresponding wild type cell, where each of said one or more polypeptides are encoded by a gene that has at least 80% sequence identity to a gene.

7 Claims, 24 Drawing Sheets

Specification includes a Sequence Listing.

(51) Int. Cl.
| | |
|---|---|
| C12N 15/00 | (2006.01) |
| C07H 21/04 | (2006.01) |
| C07H 21/02 | (2006.01) |
| C12N 1/14 | (2006.01) |
| C12N 15/80 | (2006.01) |
| C07K 14/37 | (2006.01) |
| C12P 19/44 | (2006.01) |
| C12N 9/04 | (2006.01) |
| C12N 9/02 | (2006.01) |
| C12N 9/10 | (2006.01) |

(52) U.S. Cl.
CPC ......... *C12N 9/0061* (2013.01); *C12N 9/1051* (2013.01); *C12N 9/2445* (2013.01); *C12N 15/80* (2013.01); *C12P 19/44* (2013.01); *C12Y 110/03002* (2013.01); *C12Y 204/01* (2013.01); *C12Y 302/01021* (2013.01); *C12P 2203/00* (2013.01)

(56) References Cited

OTHER PUBLICATIONS

Rauscher. Transcriptional Regulation of xyn1, Encoding Xylanase I, in Hypocrea jecorina. Eukaryot Cell. Mar. 2006; 5(3): 447-456.*
Nihira. Discovery of cellobionic acid phosphorylase in cellulolytic bacteria and fungi. FEBS Letters. 587 (2013) 3356-3561.*
Sun. Identification of the CRE-1 cellulolytic regulon in Neurospora crassa.PLoS One 6:e25654. 2011.*
Schmoll. Unravelling the molecular basis for light modulated cellulase gene expression—the role of photoreceptors in Neurospora crassa BMC Genomics 2012, 13:127.*
Aro. ACEI of Trichoderma reesei is a Repressor of Cellulase and Xylanase Expression. Appl Environ Microbiol 69:56-65. 2003.*
Extended European Search Report (includes Supplementary European Search Report and Search Opinion) received for European Patent Application No. 15786112.1, dated Oct. 25, 2017, 9 pages.
Fan et al., "A Novel Biochemical Route for Fuels and Chemicals Production from Cellulosic Biomass", Plos One, vol. 7, No. 2, Feb. 2012, pp. 1-8.
Hildebrand et al., "Engineering Neurospora Crassa for Improved Cellobiose and Cellobionate Production", Applied and Environmental Microbiology, vol. 81, No. 2, Jan. 2015, pp. 597-603.
Hildebrand et al., "Production of Cellobionate from Cellulose using an Engineered Neurospora Crassa Strain with Laccase and Redox Mediator Addition", Plos One, vol. 10, No. 4, Apr. 7, 2015, pp. 1-12.
International Preliminary Report on Patentability received for PCT Patent Application No. PCT/US2015/028090, dated Nov. 10, 2016, 8 pages.
International Search Report and Written Opinion received for PCT Patent Application No. PCT/US2015/028090, dated Aug. 10, 2015, 12 pages.
Wu et al., "Direct Cellobiose Production from Cellulose using Sextuple Beta-Glucosidase Gene Deletion Neurospora Crassa Mutants", Enzyme and Microbial Technology, vol. 52, 2013, pp. 184-189.
Znameroski et al., "Induction of Lignocellulose-Degrading Enzymes in Neurospora Crassa by Cellodextrins", PNAS, vol. 109, No. 16, Apr. 17, 2012, pp. 6012-6017.
Lin et al., "Engineering Neurospora Crassa for Cellobionate Production Directly From Cellulose Without Any Enzyme Addition", Enzyme and Microbial Technology 99 Jan. 2017, pp. 25-31.

* cited by examiner

FIG. 6

| | Starting Avicel (g) | Residual Avicel (g) | Cellulose Conversion (%) | Mycelium produced (g) | Yield of cellulose and cellulose breakdown from consumed Avicel (%) | Yield of mycelium and non-consumed Avicel (g/g Avicel) |
|---|---|---|---|---|---|---|
| Wild Type | 1.0 | 0.47±0.05 | 53±5% | 0.28±0.02 | 0 | 52±5% |
| Wild Type + CDH | 1.0 | 0.40±0.03 | 60±3% | 0.31±0.04 | 0 | 51±7% |
| F5 | 1.0 | 0.36±0.01 | 64±1% | 0.14±0.02 | 52±7% | 22±2% |
| F5 + CDH | 1.0 | 0.35±0.0002 | 65±0.02% | 0.16±0.01 | 49±2% | 24±1% |

A

B

C

BIOLOGICAL PLATFORM FOR PRODUCTION OF COMMODITY CHEMICALS

CROSS-REFERENCE(S) TO RELATED APPLICATION(S)

This application is a U.S. National Phase patent application of PCT/US2015/028090, filed Apr. 28, 2015, which claims the benefit of U.S. Provisional Application Ser. No. 61/985,379 filed on Apr. 28, 2014, the disclosures of which are herein incorporated by reference in their entirety.

STATEMENT REGARDING FEDERALLY-SPONSORED RESEARCH

This invention was made with government support under Grant No. 2011-67009-20060 awarded by United States Department of Agriculture-National Institute of Food and Agriculture (USDA-NIFA). The government has certain rights in the invention. This invention was also made with State of California support under California Energy Commission Grant number 55779A/08-03. The Energy Commission has certain rights to this invention.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 514112007800SEQLIST.TXT, date recorded: Oct. 28, 2016, size: 97 KB).

FIELD

The present disclosure generally relates to biological platforms for the conversion of cellulosic biomass into fuels and chemicals. More specifically, the present disclosure relates to the conversion of cellulosic materials into sugar acids or their salts, which may then be used to produce commodity chemicals.

BACKGROUND

Cellulosic biomass, which is available at low cost and in large abundance, is one of the only foreseeable sustainable sources for organic fuels, chemicals and materials (Lynd et al., 2005; Lynd et al., 2002, Lynd et al., 1999). In particular, ethanol production from cellulosic biomass has near-zero greenhouse emissions and offers many other environmental benefits (Lynd et al., 2005; Lynd et al., 1999; Lynd et al., 1991). The primary obstacle impeding production of ethanol and other chemicals from cellulosic biomass is the lack of technology for low-cost production (Lynd et al., 1999).

Traditional biochemical platforms or methods for fuel- and chemical-production generate sugars from cellulosic feedstock as reactive intermediates. These sugars can then be fermented to produce fuels and chemicals. There are five key steps involved in the current biochemical platform: (1) pre-treatment, (2) cellulase production, (3) enzymatic hydrolysis, (4) fermentation, and (5) product recovery. The first three steps: pre-treatment, cellulase production, and enzymatic hydrolysis are the three most costly steps in the production process, constituting approximately 65% of the overall processing cost.

The first step, pre-treatment, is a process to remove hemicellulose and lignin to increase the susceptibility of cellulose to subsequent enzymatic hydrolysis, thus allowing the exposed cellulose to be hydrolyzed into sugars by cellulases. The pre-treatment process tends to be thermochemical. Techniques used in the process include treatment with acid or base, or through steam or ammonia explosions. Most of the techniques are energy-intensive, expensive, and often polluting. In addition, capital cost for pre-treatment reactors are extremely high due to specific material requirements for acid or alkali resistance at elevated temperatures.

After the pre-treatment step, cellulases are added in a second step to hydrolyze cellulose, resulting in the production of sugars. While cellulase production costs have dropped significantly due to industrial production of enzymes, costs of this step still remain high. Lowering the processing costs of the two aforementioned steps is crucial for the realization of cost-effective production of ethanol and chemicals from biomass. Thus, there exists a need for improved compositions and methods for conversion of cellulosic biomass into commodity chemicals.

BRIEF SUMMARY

In one aspect, the present disclosure relates to a recombinant host cell including: a) reduced activity of one or more polypeptides having β-glucosidase activity as compared to a corresponding wild type cell, where each of said one or more polypeptides are encoded by a gene that has at least 80% sequence identity to a gene selected from the group of NCU00130, NCU04952, NCU05577, NCU07487, NCU08755, and NCU03641 genes; b) reduced activity of a polypeptide having cellobionate phosphorylase activity as compared to a corresponding wild type cell, where said polypeptide is encoded by a gene that has at least 80% sequence identity to NCU09425 (NdvB); c) reduced activity of a polypeptide encoded by a gene that has at least 80% sequence identity to NCU08807 (CRE-1) as compared to a corresponding wild type cell; and d) reduced activity of a polypeptide encoded by a gene that has at least 80% sequence identity to NCU09333 (ACE-1) as compared to a corresponding wild type host cell. In some embodiments, the host cell is a fungal cell. In some embodiments, the fungal cell is *Neurospora crassa*. In some embodiments that may be combined with any of the preceding embodiments, reduced activity of one or more of the polypeptides having β-glucosidase activity is due to a genetic mutation. In some embodiments, a genetic mutation is present in two or more, three or more, four or more, five or more, or six or more genes encoding the polypeptides having β-glucosidase activity. In some embodiments, at least one of the genetic mutations is a knockout mutation. In some embodiments that may be combined with any of the preceding embodiments, reduced activity a polypeptide having cellobionate phosphorylase activity is due to a genetic mutation. In some embodiments, the genetic mutation is a knockout mutation. In some embodiments that may be combined with any of the preceding embodiments, reduced activity of a polypeptide encoded by a gene that has at least 80% sequence identity to NCU08807 (CRE-1) is due to a genetic mutation. In some embodiments, the genetic mutation is a knockout mutation. In some embodiments that may be combined with any of the preceding embodiments, reduced activity of a polypeptide encoded by a gene that has at least 80% sequence identity to NCU09333 (ACE-1) is due to a genetic mutation. In some embodiments, the genetic mutation is a knockout mutation. In some embodiments that may be combined with any of the preceding embodiments, the host cell further comprises reduced activity of a polypeptide encoded by a gene that has at least 80% sequence identity to NCU08290 (MUS51) as compared to a corresponding wild type cell. In some embodiments, reduced activity of a polypeptide encoded by a gene that has at least 80% sequence identity to NCU08290 (MUS51) is due to a genetic mutation. In some embodiments, the genetic mutation is a knockout mutation. In some embodiments that may be combined with any of the preceding embodiments, the host cell further comprises a polypeptide having increased laccase expression or activity as compared to a corresponding wild type cell. In some embodiments, the polypeptide is encoded by a gene that has at least 80% sequence identity to NCU04528. In some embodiments, expression of the polypeptide is under the control of a constitutive promoter. In some embodiments that may be combined with any of the preceding embodiments, the host cell further comprises a polypeptide having increased cellobiose dehydrogenase expression or activity as compared to a corresponding wild type cell. In some embodiments, expression of the polypeptide having increased cellobiose dehydrogenase expression or activity is under the control of a constitutive promoter. In some embodiments that may be combined with any of the preceding embodiments, the host cell produces a sugar acid from cellulose. In some embodiments that may be combined with any of the preceding embodiments, the host cell produces cellobiose. In some embodiments that may be combined with any of the preceding embodiments, the sugar acid is cellobionate. In some embodiments, consumption of cellobionate by the host cell is reduced by at least 80% as compared to a corresponding wild type cell.

In another aspect, the present disclosure relates to a recombinant *N. crassa* cell including: a) a mutation in each of NCU00130, NCU04952, NCU05577, NCU07487, NCU08755, and NCU03641 genes, where said mutation reduces β-glucosidase activity of polypeptides encoded by said genes; b) a mutation in the NCU09425 (NdvB) gene, where said mutation reduces cellobionate phosphorylase activity of the polypeptides encoded by said gene; c) a mutation in each of NCU08807 (CRE-1) and NCU09333 (ACE-1) genes, where said mutations reduce activity of polypeptides encoded by said genes; d) a laccase having increased expression or activity as compared to a wild type *N. crassa* cell, and where the recombinant *N. crassa* cell produces cellobionate from cellulose.

In another aspect, the present disclosure relates to a method of producing sugar acids, the method including: a) providing a host cell having i) reduced activity of one or more polypeptides having β-glucosidase activity as compared to a corresponding wild type cell, where each of said one or more polypeptides are encoded by a gene that has at least 80% sequence identity to a gene selected from the group of NCU00130, NCU04952, NCU05577, NCU07487, NCU08755, and NCU03641 genes; ii) reduced activity of a polypeptide having cellobionate phosphorylase activity as compared to a corresponding wild type cell, where said polypeptide is encoded by a gene that has at least 80% sequence identity to NCU09425 (NdvB); iii) reduced activity of a polypeptide encoded by a gene that has at least 80% sequence identity to NCU08807 (CRE-1) as compared to a corresponding wild type cell; and iv) reduced activity of a polypeptide encoded by a gene that has at least 80% sequence identity to NCU09333 (ACE-1) as compared to a corresponding wild type host cell; b) culturing the host cell in a medium including cellulose, where the host cell produces a sugar acid from the cellulose.

In another aspect, the present disclosure relates to a method of producing sugar acids, the method including a) providing a host cell of any of the preceding embodiments, and b) culturing the host cell in a medium including cellulose, where the host cell produces a sugar acid from the cellulose. In some embodiments, the method further includes a step of substantially purifying the sugar acid from the medium. In some embodiments that may be combined with any of the preceding embodiments, the host cell produces cellobiose. In some embodiments that may be combined with any of the preceding embodiments, the sugar acid is cellobionate. In some embodiments, consumption of cellobionate by the host cell is reduced by at least 80% as compared to a corresponding wild type cell. In some embodiments that may be combined with any of the preceding embodiments, the host cell is cultured in the presence of an exogenous source of laccase. In some embodiments that may be combined with any of the preceding embodiments, the host cell is cultured in the presence of an exogenous source of cellobiose dehydrogenase. In some embodiments that may be combined with any of the preceding embodiments, the medium further includes a redox mediator.

DESCRIPTION OF THE FIGURES

The patent or application file contains at least one drawing executed in color. Copies of this patent or patent application publication with color drawings will be provided by the office upon request and payment of the necessary fee.

FIG. 6 illustrates a summary of cellulose conversion and mycelial mass production.

DETAILED DESCRIPTION

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described herein and shown, but are to be accorded the scope consistent with the claims.

Overview

The present disclosure generally relates to biological platforms for the conversion of cellulosic biomass into fuels and chemicals. More specifically, the present disclosure relates to the conversion of cellulosic materials into sugar acids or their salts, which may then be used to produce commodity chemicals.

Figure 1:
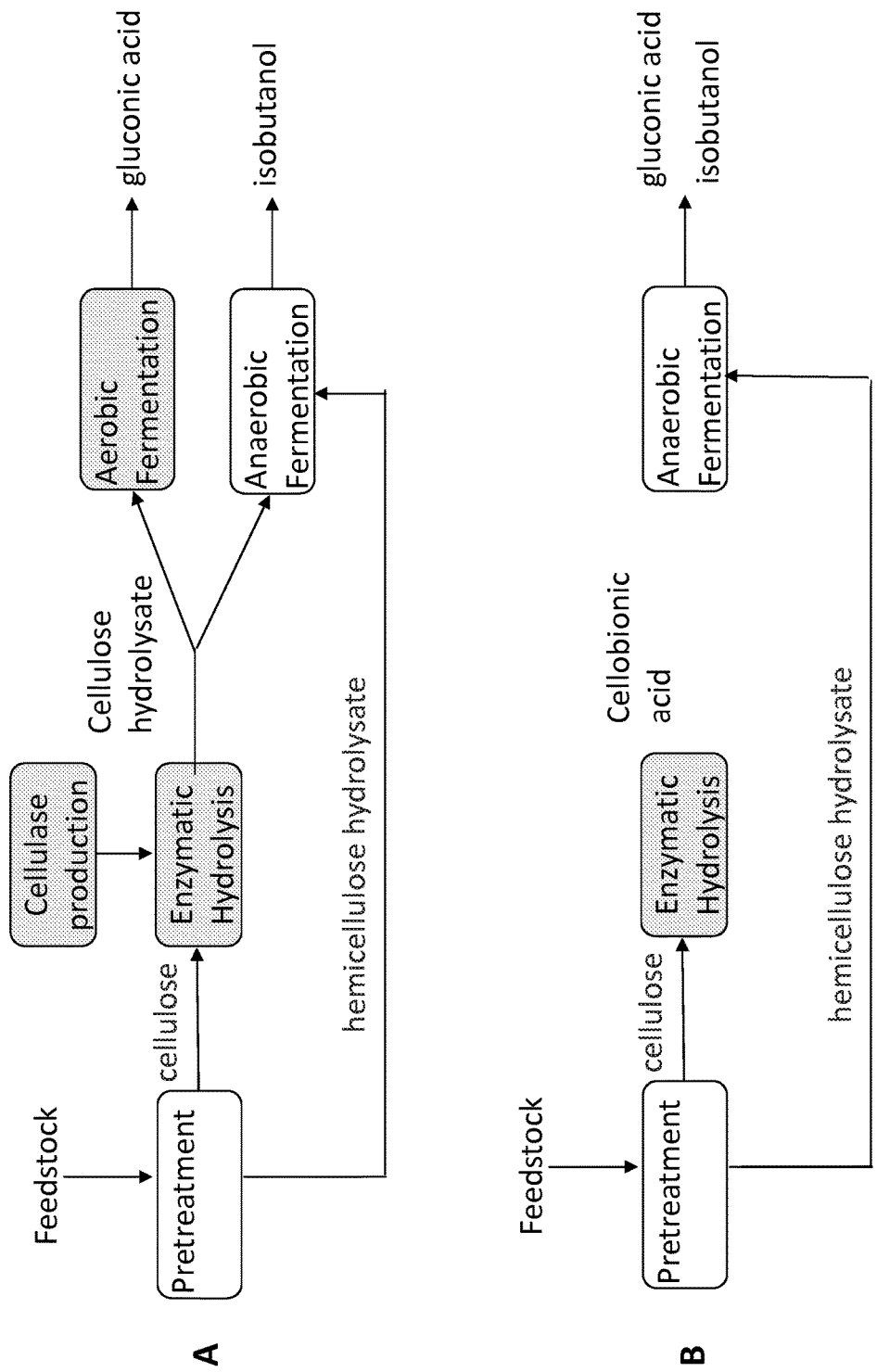
FIG. 1A illustrates a flow chart of the conventional steps used in methods of producing commodity chemicals from cellulosic biomass.
FIG. 1B illustrates a flow chart for methods of direct enzymatic hydrolysis of cellulose.
Figure 2:
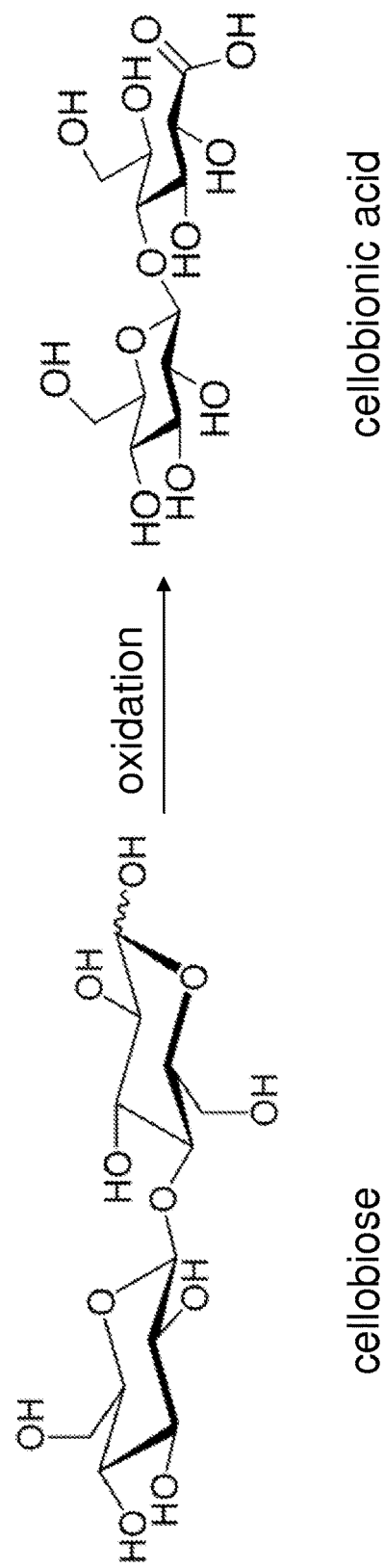
FIG. 2 illustrates the chemical conversion of cellobiose to cellobionic acid.

FIG. 1A illustrates the conventional steps used in the production of gluconic acid and isobutanol from cellulosic biomass, which involves the production of cellulase and a step of aerobic fermentation. Applicants propose an alternative route, outlined in FIG. 1B, which circumvents the need for cellulase production, but is instead based on the direct enzymatic hydrolysis of cellulose to produce sugar acids, such as cellobionic acid (See also FIG. 2), and subsequent downstream products.

Figure 3:
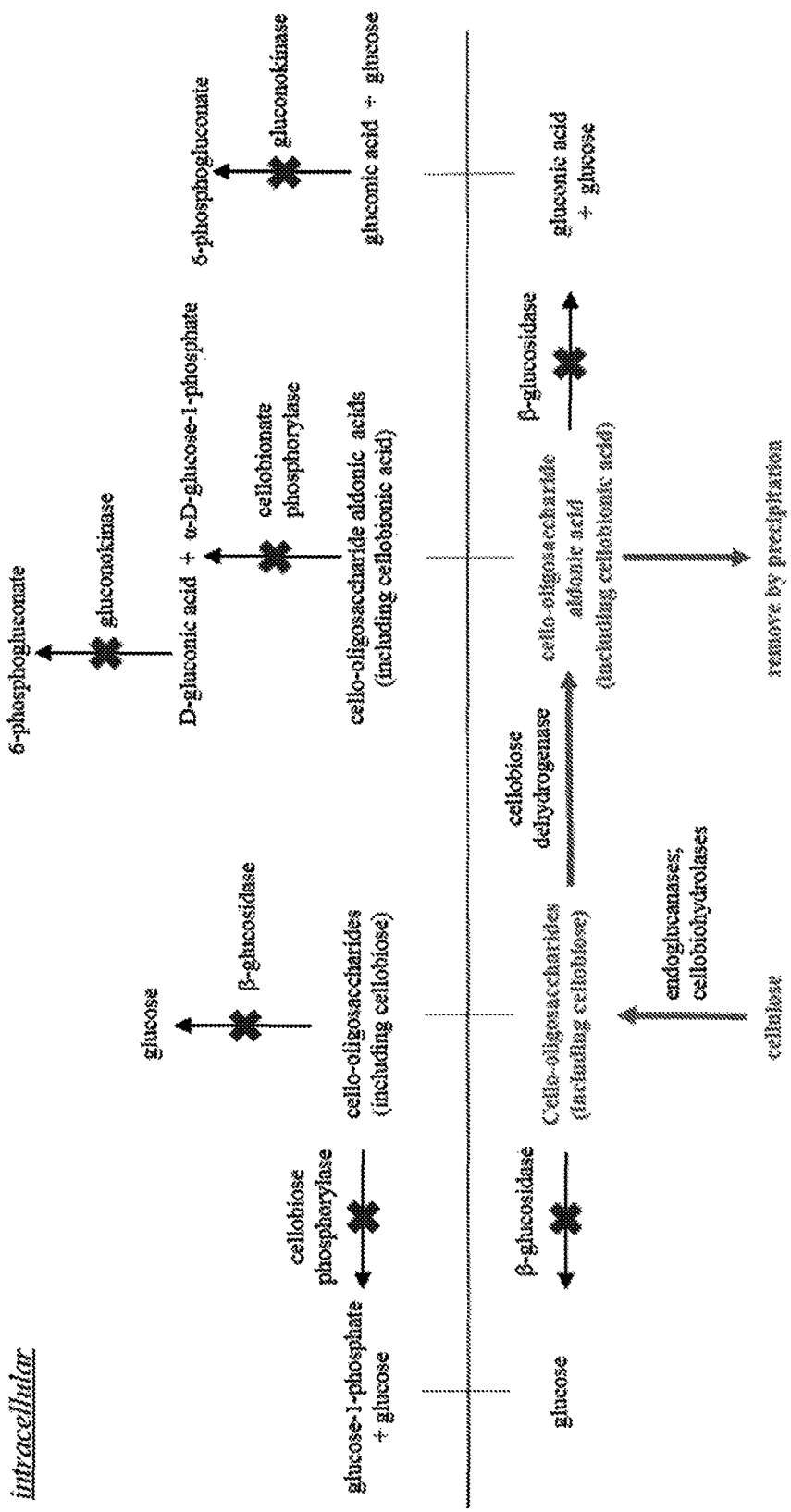
FIG. 3 illustrates the cellulose degradation mechanism for some cellulolytic microorganisms, such as *Neurospora crassa*.

Cellulolytic microorganisms are capable of hydrolyzing cellulose, and thus such organisms may be used as work horses for the production of commodity chemicals. FIG. 3 shows the cellulose degradation mechanism for some cellulolytic microorganisms, including Neurospora crassa. Cellulose is hydrolyzed by endoglucanases and exoglucanases to cello-oligosaccharides, with cellobiose as the main component. The resultant cellobiose as the main component is oxidized by cellobiose dehydrogenase to produce cellobiono-1,5-lactone, which reacts spontaneously with water to form cellobionic acid. In addition, cellobionic acid is released from cellulose by the combined action of lytic polysaccharide monooxygenase and cellobiohydrolase. The cellobionic acid is transported into the cytoplasm, followed by phosphorolysis by cellobionic acid phosphorylase (NCU09425) to produce αGlc1P and D-gluconic acid. The released αGlc1P is converted into D-glucose 6-phosphate by a-phosphoglucomutase (EC 2.7.5.1) to enter the glycolysis pathway. The released D-gluconic acid is converted into ribulose 5-phosphate via 6-phosphogluconate by the sequential reaction of gluconokinase (EC 2.7.1.12) and 6-phosphogluconate dehydrogenase (EC 1.1.1.44) to enter the pentose phosphate pathway (Nihira et al., 2013). One of the notable features of the metabolic pathway for cellulose described herein is that the fungus uses ATP-derived energy efficiently, because it is possible to phosphorylate a D-glucose residue of cellobionic acid directly without consuming ATP by ATP-dependent carbohydrate kinase. Cellobionic acid appears to be a less ideal substrate for β-glucosidase because the hydrolysate of this reaction, D-gluconic acid, is a non-competitive inhibitor of β-glucosidase (Nihira et al., 2013). In addition, it should be noted that a variety of cellulolytic fungi of the phylum Ascomycota also possess a cellobionic acid phosphorylase homologous protein.

After the generation of cello-oligosaccharides, β-glucosidase enzymes can then hydrolyze cello-oligosaccharides into glucose, which can be metabolized by fungi. If β-glucosidase enzyme activity is reduced and cellobiose dehydrogenase (CDH) activity is increased, carbon flow can be directed toward aldonic acid production. These organic acids can be continuously removed from the broth, such as by calcium hydroxide precipitation, to avoid any possible inhibition. In practice, some β-glucosidase activity must remain intact in the cell to support cell growth and enzyme production. Gluconic acid utilization can be prevented by reducing the activity of gluconokinases, thus leaving this compound available for subsequent ethanol fermentation. Gluconic acid was found to be a non-competitive product inhibitor to the β-glucosidase for *A. niger*, and its presence could inhibit any noticeable hydrolysis of cellobionate by the residual β-glucosidase activity. Further, hydrolysis experiments revealed that cellobionic acid was hydrolyzed by β-glucosidase at a rate almost 10-fold lower than for cellobiose and the formed gluconic acid was an inhibitor of the β-glucosidase (Cannella, 2012).

Applicants disclose herein compositions and methods for conversion of cellulose into downstream products. The present disclosure is based, at least in part, on Applicant's discovery that a *Neurospora crassa* engineered to contain mutations in six β-glucosidase genes, a mutation in the CRE-1 gene, a mutation in the ACE-1 gene, a mutation in the NdvB cellobionate phosphorylase gene, and either engineered to overexpress a laccase gene or cultured in the presence of exogenous laccase enzyme, produced surprisingly high amounts of cellobionic acid (cellobionate). This engineered strain concomitantly failed to metabolize the cellobionate that was produced, allowing cellobionate to accumulate. As described above, cellobionate may be used for the production of downstream products, such as gluconic acid and isobutanol.

Polypeptides Having Modified Activity

The present disclosure relates to recombinant host cells having modified activity of various polypeptides as compared to corresponding control cells, such as wild type cells. As used herein, a "polypeptide" is an amino acid sequence including a plurality of consecutive polymerized amino acid residues (e.g., at least about 15 consecutive polymerized amino acid residues). As used herein, "polypeptide" refers to an amino acid sequence, oligopeptide, peptide, protein, or portions thereof, and the terms "polypeptide" and "protein" are used interchangeably.

β-Glucosidase Polypeptides

Host cells of the present disclosure have reduced activity of one or more β-glucosidase polypeptides as compared to a corresponding wild type cell.

β-glucosidase (bgl) genes of the present disclosure encode β-glucosidase enzymes. As used herein, "β-glucosidase" refers to a β-D-glucoside glucohydrolase (E.C. 3.2.1.21), which catalyzes the hydrolysis of terminal non-reducing β-D-glucose residues with the release of β-D-glucose. A β-glucosidase is any enzyme that catalyzes the hydrolysis of terminal non-reducing residues in β-D-glucosides, such as cellodextrins, with release of glucose.

β-glucosidases of the present disclosure may be either intracellular β-glucosidases or extracellular β-glucosidases. As used herein "intracellular β-glucosidases" are expressed within lignocellulolytic cells and hydrolyze cellodextrins transported into the cell. As used herein "extracellular β-glucosidases" are expressed and secreted from lignocellulolytic cells or expressed on the surface of lignocellulolytic cells.

In certain embodiments, the β-glucosidase is a glycosyl hydrolase family 1 member. Members of this group can be identified by the motif, [LIVMFSTC]-[LIVFYS]-[LIV]-[LIVMST]-E-N-G-[LIVMFAR]-[CSAGN] (SEQ ID NO: 23). Here, E is the catalytic glutamate. In some embodiments, the β-glucosidase is from *N. crassa*. Other β-glucosidases may include those from the glycosyl hydrolase family 3. These β-glucosidases can be identified by the following motif according to PROSITE: [LIVM](2)-[KR]-x-[EQKRD]-x(4)-G-[LIVMFTC]-[LIVT]-[LIVMF]-[ST]-D-x(2)-[SGADNIT] (SEQ ID NO: 24). Here D is the catalytic aspartate. Typically, any β-glucosidase may be used that contains the conserved domain of β-glucosidase/6-phospho-β-glucosidase/β-galactosidase found in NCBI sequence COG2723.

In certain embodiments, β-glucosidases of the present disclosure include, for example, *N. crassa* β-glucosidases encoded by NCU00130, NCU04952, NCU05577, NCU07487, NCU08054, NCU08755, and NCU03641. Suitable β-glucosidases of the present disclosure also include homologs, orthologs, and paralogs of NCU00130, NCU04952, NCU05577, NCU07487, NCU08054, NCU08755, and NCU03641.

Intracellular β-glucosidases of the present disclosure include, for example, those encoded by NCU00130, NCU05577, NCU07487, NCU08054, homologs thereof, orthologs thereof, and paralogs thereof. Extracellular β-glucosidases of the present disclosure include, for example, those encoded by NCU04952, NCU08755, NCU03641, homologs thereof, orthologs thereof, and paralogs thereof.

In some embodiments, the polypeptide having reduced β-glucosidase activity is a polypeptide encoded by NCU00130, NCU04952, NCU05577, NCU07487, NCU08755, and/or NCU03641. The amino acid sequence of the protein encoded by NCU00130 is set forth herein as SEQ ID NO: 1. The amino acid sequence of the protein encoded by NCU04952 is set forth herein as SEQ ID NO: 3. The amino acid sequence of the protein encoded by NCU05577 is set forth herein as SEQ ID NO: 5. The amino acid sequence of the protein encoded by NCU07487 is set forth herein as SEQ ID NO: 7. The amino acid sequence of the protein encoded by NCU08755 is set forth herein as SEQ ID NO: 9. The amino acid sequence of the protein encoded by NCU03641 is set forth herein as SEQ ID NO: 11. In some embodiments, the polypeptide having reduced β-glucosidase activity is a polypeptide encoded by a gene that has at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to NCU00130, NCU04952, NCU05577, NCU07487, NCU08755, or NCU03641 genes. The nucleotide sequence of NCU00130 is set forth herein as SEQ ID NO: 2. The nucleotide sequence of NCU04952 is set forth herein as SEQ ID NO: 4. The nucleotide sequence of NCU05577 is set forth herein as SEQ ID NO: 6. The nucleotide sequence of NCU07487 is set forth herein as SEQ ID NO: 8. The amino acid sequence of NCU08755 is set forth herein as SEQ ID NO: 10. The nucleotide sequence of NCU03641 is set forth herein as SEQ ID NO: 12.

Various other β-glucosidases are well-known in the art and may be used in the methods and compositions of the present disclosure.

One or more β-glucosidases may have reduced activity in host cells of the present disclosure. Host cells of the present disclosure may have reduced activity of two or more, three or more, four or more, five or more, or six or more polypeptides having β-glucosidase activity.

Cellobionate Phosphorylase Polypeptides

Host cells of the present disclosure have reduced activity of one or more cellobionate phosphorylase proteins as compared to a corresponding wild type cell.

Figure 15:
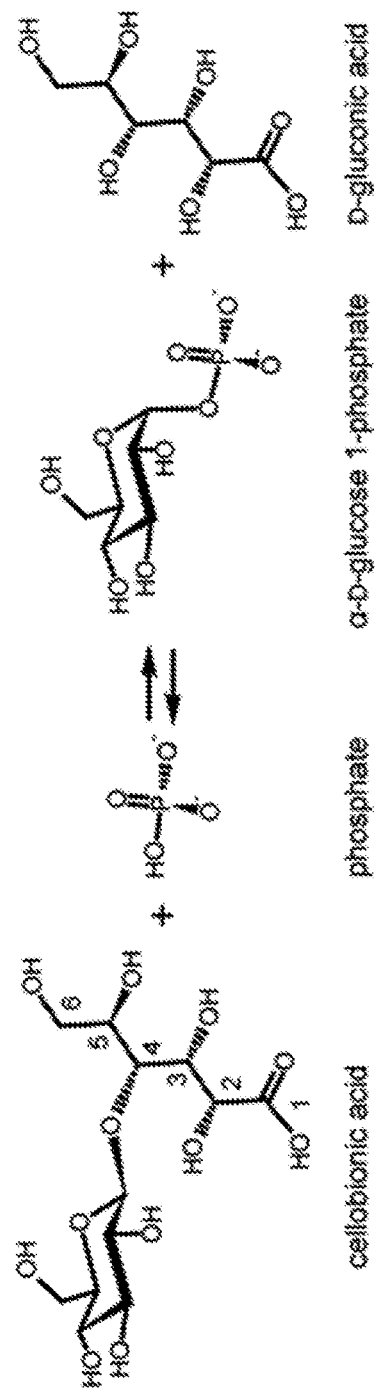
FIG. 15 illustrates the conversion of cellobionic acid to α-D-glucose-1-phosphate and D-gluconic acid.

Cellobionate phosphorylases are well-known in the art and are described herein. Cellobionate phosphorylase catalyzes the reaction outlined in FIG. 15 and has activity associated with EC 2.4.1.321. In this reaction, cellobionate phosphorylase catalyzes the phosphorolysis of cellobionic acid (4-O-β-D-glucopyranosyl-D-gluconate) to produce α-D-glucose-1-phosphate and D-gluconic acid. In some embodiments, cellobionate phosphorylases of the present disclosure contain one or more glycosyltransferase family 36 protein domains.

In some embodiments, the polypeptide having reduced cellobionate phosphorylase activity is a polypeptide encoded by NCU09425, which encodes the NdvB protein from *Neurospora crassa*. The amino acid sequence of the protein encoded by NCU09425 is set forth herein as SEQ ID NO: 13. In some embodiments, the polypeptide having reduced cellobionate phosphorylase activity is a polypeptide encoded by a gene that has at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to NCU09425. The nucleotide sequence of NCU09425 is set forth herein as SEQ ID NO: 14. Various other cellobionate phosphorylases are well-known in the art and may be used in the methods and compositions of the present disclosure. Other exemplary cellobionate phosphorylases include, for example, a glycoside hydrolase family 94 cellobionate phosphorylase from the bacterium *Xanthomonas campestris*.

CRE-1 Polypeptides

Host cells of the present disclosure have reduced activity of a CRE-1 protein as compared to a corresponding wild type cell. CRE-1 proteins are well-known in the art and are described herein. CRE-1 is a transcription factor protein. Transcription factor polypeptides, generally speaking, are polypeptides involved in the regulation of gene expression in a cell. Transcription factor polypeptides may have activity relating to the control of expression of a nucleic acid, such as DNA. Transcription factor activity is well-known in the art. For example, transcription factor polypeptide activity may include DNA-binding activity or activity relating to the regulation of gene expression.

It is thought that CRE-1 is involved in catabolite repression. Deletion of the cre has been shown to increase cellulase expression. A cre-strain has decreased growth rate on preferred carbon sources; however, on Avicel it produces 30-50% more cellulase and consumes avicel faster (Sun et al., 2011), and cre expression correlates with cellulase expression.

In some embodiments, the polypeptide having reduced CRE-1 activity is a polypeptide encoded by NCU08807, which encodes a CRE-1 protein from *Neurospora crassa*. The amino acid sequence of the protein encoded by NCU08807 is set forth herein as SEQ ID NO: 15. In some embodiments, the polypeptide having reduced CRE-1 activity is a polypeptide encoded by a gene that has at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to NCU08807. The nucleotide sequence of NCU08807 is set forth herein as SEQ ID NO: 16. Various other CRE-1 proteins are well-known in the art and may be used in the methods and compositions of the present disclosure.

ACE-1 Polypeptides

Host cells of the present disclosure have reduced activity of an ACE-1 protein as compared to a corresponding wild type cell. ACE-1 proteins are well-known in the art and are described herein. ACE-1 is a zinc finger transcription factor protein. Mutation of the ace-1 gene (ace-) resulted in higher cellulase expression in *T. reesei* (Aro et al., 2003).

In some embodiments, the polypeptide having reduced ACE-1 activity is a polypeptide encoded by NCU09333, which encodes an ACE-1 protein from *Neurospora crassa*. The amino acid sequence of the protein encoded by NCU09333 is set forth herein as SEQ ID NO: 17. In some embodiments, the polypeptide having reduced ACE-1 activity is a polypeptide encoded by a gene that has at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to NCU09333. The nucleotide sequence of NCU09333 is set forth herein as SEQ ID NO: 18. Various other ACE-1 proteins are well-known in the art and may be used in the methods and compositions of the present disclosure.

MUS51 Polypeptides

Host cells of the present disclosure may have reduced activity of a MUSS 1 protein as compared to a corresponding wild type cell. MUSS 1 proteins are well-known in the art and are described herein. MUSS 1 is an ATP-dependent DNA helicase II subunit 1 protein (E.C. 3.6.4.12). MUSS 1 proteins are involved in non-homologous end joining (NHEJ) DNA double strand break repair. Without wishing to be bound by theory, it is thought that reducing MUSS 1 protein activity in a host cell will increase the chances for and/or frequency of homologous recombination in the host cell, which may make genetic modification of the host cell easier.

In some embodiments, the polypeptide having reduced MUSS 1 activity is a polypeptide encoded by NCU08290, which encodes a MUSS 1 protein from *Neurospora crassa*. In some embodiments, the polypeptide having reduced MUSS 1 activity is a polypeptide encoded by a gene that has at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to NCU08290. Various other MUS51 proteins are well-known in the art and may be used in the methods and compositions of the present disclosure.

Laccase Polypeptides

Host cells of the present disclosure may have increased expression or activity of a laccase protein as compared to a corresponding wild type cell. Laccase proteins may also be added exogenously to culture media in methods of the present disclosure. Laccase proteins are well-known in the art and are described herein. Laccases are "blue" copper containing oxidases (E.C. 1.10.3.2). Laccases catalyze the following reaction: 4 benzenediol+$O_2$=4 benzosemiquinone+$2H_2O$. These multi copper enzymes have low specificity acting on both o- and p-quinols, and often acting also on aminophenols and phenylenediamine. Laccases may also act on phenols and similar molecules, performing one-electron oxidations. Because laccase proteins belong to the oxidase enzyme family, these enzymes require oxygen as a second substrate for enzymatic action.

In some embodiments, the polypeptide having increased laccase expression or activity is a polypeptide encoded by NCU04528, which encodes a laccase protein from *Neurospora crassa*. The amino acid sequence of the protein encoded by NCU04528 is set forth herein as SEQ ID NO: 19. In some embodiments, the polypeptide having increased laccase expression or activity is a polypeptide encoded by a gene that has at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to NCU04528. The nucleotide sequence of NCU04528 is set forth herein as SEQ ID NO: 20. Various other laccase proteins are well-known in the art and may be used in the methods and compositions of the present disclosure.

Cellobiose Dehydrogenase Polypeptides

Host cells of the present disclosure may have increased expression or activity of a cellobiose dehydrogenase protein as compared to a corresponding wild type cell. Cellobiose dehydrogenase proteins may also be added exogenously to culture media in methods of the present disclosure. Cellobiose dehydrogenase (CDH) proteins are well-known in the art and are described herein. CDH enzymes catalyze the following reaction: cellobiose+acceptor=cellobiono-1,5-lactone+reduced acceptor (E.C. 1.1.99.18). CDH proteins contain an N-terminal heme domain and a C-terminal dehydrogenase domain. Some CDH proteins also contain a cellulose binding module (CBM) at the C-terminus of the protein. Orthologs of the CDH heme domain are found only in fungal proteins, whereas orthologs of the dehydrogenase domain are found in proteins throughout all domains of life; the dehydrogenase domain is part of the larger GMC oxidoreductase superfamily.

In some embodiments, the polypeptide having increased cellobiose dehydrogenase expression or activity is a polypeptide encoded by NCU00206, which encodes a cellobiose dehydrogenase protein from *Neurospora crassa*. The amino acid sequence of the protein encoded by NCU00206 is set forth herein as SEQ ID NO: 21. In some embodiments, the polypeptide having increased cellobiose dehydrogenase expression or activity is a polypeptide encoded by a gene that has at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 98%, at least 99%, or 100% identity to NCU00206. The nucleotide sequence of NCU00206 is set forth herein as SEQ ID NO: 22. Various other cellobiose dehydrogenase proteins are well-known in the art and may be used in the methods and compositions of the present disclosure. Other cellobiose dehydrogenases include, for example, the polypeptides of Accession Numbers: XM_411367, BAD32781, BAC20641, XM_389621, AF257654, AB187223, XM_360402, U46081, AF081574, AY187232, AF074951, and AF029668.

Polynucleotides Encoding Polypeptides

The present disclosure further relates to polynucleotides that encode polypeptides having modified activity of the present disclosure. Polynucleotides that encode a polypeptide are also referred to herein as "genes." For example, polynucleotides encoding any known or putative β-glucosidase, cellobionate phosphorylase, CRE-1 protein, ACE-1 protein, MUS51 protein, laccase, or cellobiose dehydrogenase polypeptide as described herein are provided. Methods for determining the relationship between a polypeptide and a polynucleotide that encodes the polypeptide are well-known to one of skill in the art. Similarly, methods of determining the polypeptide sequence encoded by a polynucleotide sequence are well-known to one of skill in the art.

As used herein, the terms "polynucleotide," nucleic acid sequence," "nucleic acid," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing non-nucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog, and inter-nucleotide modifications. As used herein, the symbols for nucleotides and polynucleotides are those recommended by the IUPAC-IUB Commission of Biochemical Nomenclature.

Sequences of the polynucleotides of the present disclosure may be prepared by various suitable methods known in the art, including, for example, direct chemical synthesis or cloning. For direct chemical synthesis, formation of a polymer of nucleic acids typically involves sequential addition of 3'-blocked and 5'-blocked nucleotide monomers to the terminal 5'-hydroxyl group of a growing nucleotide chain, wherein each addition is effected by nucleophilic attack of the terminal 5'-hydroxyl group of the growing chain on the 3'-position of the added monomer, which is typically a phosphorus derivative, such as a phosphotriester, phosphoramidite, or the like. Such methodology is known to those of ordinary skill in the art and is described in the pertinent texts and literature (e.g., in Matteucci et al., (1980) *Tetrahedron Lett* 21:719-722; U.S. Pat. Nos. 4,500,707; 5,436,327; and 5,700,637). In addition, the desired sequences may be isolated from natural sources by splitting DNA using appropriate restriction enzymes, separating the fragments using gel electrophoresis, and thereafter, recovering the desired polynucleotide sequence from the gel via techniques known to those of ordinary skill in the art, such as utilization of polymerase chain reactions (PCR; e.g., U.S. Pat. No. 4,683,195).

Methods of Identifying Sequence Similarity

Various methods are known to those of skill in the art for identifying similar (e.g. homologs, orthologs, paralogs, etc.) polypeptide and/or polynucleotide sequences, including phylogenetic methods, sequence similarity analysis, and hybridization methods.

Phylogenetic trees may be created for a gene family by using a program such as CLUSTAL (Thompson et al. *Nucleic Acids Res*. 22: 4673-4680 (1994); Higgins et al. *Methods Enzymol* 266: 383-402 (1996)) or MEGA (Tamura et al. *Mol. Biol. & Evo.* 24:1596-1599 (2007)). Once an initial tree for genes from one species is created, potential orthologous sequences can be placed in the phylogenetic tree and their relationships to genes from the species of interest can be determined. Evolutionary relationships may also be inferred using the Neighbor-Joining method (Saitou and Nei, *Mol. Biol. & Evo.* 4:406-425 (1987)). Homologous sequences may also be identified by a reciprocal BLAST strategy. Evolutionary distances may be computed using the Poisson correction method (Zuckerkandl and Pauling, pp. 97-166 in *Evolving Genes and Proteins*, edited by V. Bryson and H. J. Vogel. Academic Press, New York (1965)).

In addition, evolutionary information may be used to predict gene function. Functional predictions of genes can be greatly improved by focusing on how genes became similar in sequence (i.e. by evolutionary processes) rather than on the sequence similarity itself (Eisen, *Genome Res.* 8: 163-167 (1998)). Many specific examples exist in which gene function has been shown to correlate well with gene phylogeny (Eisen, *Genome Res.* 8: 163-167 (1998)). By using a phylogenetic analysis, one skilled in the art would recognize that the ability to deduce similar functions conferred by closely-related polypeptides is predictable.

When a group of related sequences are analyzed using a phylogenetic program such as CLUSTAL, closely related sequences typically cluster together or in the same clade (a group of similar genes). Groups of similar genes can also be identified with pair-wise BLAST analysis (Feng and Doolittle, *J. Mol. Evol.* 25: 351-360 (1987)). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount, Bioinformatics: Sequence and Genome Analysis Cold Spring Harbor Laboratory Press, Cold Spring Harbor, N.Y., page 543 (2001)).

To find sequences that are homologous to a reference sequence, BLAST nucleotide searches can be performed with the BLASTN program, score=100, wordlength=12, to obtain nucleotide sequences homologous to a nucleotide sequence encoding a protein of the disclosure. BLAST protein searches can be performed with the BLASTX program, score=50, wordlength=3, to obtain amino acid sequences homologous to a protein or polypeptide of the disclosure. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, or PSI-BLAST, the default parameters of the respective programs (e.g., BLASTN for nucleotide sequences, BLASTX for proteins) can be used.

Methods for the alignment of sequences and for the analysis of similarity and identity of polypeptide and polynucleotide sequences are well-known in the art.

As used herein "sequence identity" refers to the percentage of residues that are identical in the same positions in the sequences being analyzed. As used herein "sequence similarity" refers to the percentage of residues that have similar biophysical/biochemical characteristics in the same positions (e.g. charge, size, hydrophobicity) in the sequences being analyzed.

Methods of alignment of sequences for comparison are well-known in the art, including manual alignment and computer assisted sequence alignment and analysis. This latter approach is a preferred approach in the present disclosure, due to the increased throughput afforded by computer assisted methods. As noted below, a variety of computer programs for performing sequence alignment are available, or can be produced by one of skill.

The determination of percent sequence identity and/or similarity between any two sequences can be accomplished using a mathematical algorithm. Examples of such mathematical algorithms are the algorithm of Myers and Miller, CABIOS 4:11-17 (1988); the local homology algorithm of Smith et al., Adv. Appl. Math. 2:482 (1981); the homology alignment algorithm of Needleman and Wunsch, *J. Mol. Biol.* 48:443-453 (1970); the search-for-similarity-method of Pearson and Lipman, *Proc. Natl. Acad. Sci.* 85:2444-2448 (1988); the algorithm of Karlin and Altschul, *Proc. Natl. Acad. Sci. USA* 87:2264-2268 (1990), modified as in Karlin and Altschul, *Proc. Natl. Acad. Sci. USA* 90:5873-5877 (1993).

Computer implementations of these mathematical algorithms can be utilized for comparison of sequences to determine sequence identity and/or similarity. Such implementations include, for example: CLUSTAL in the PC/Gene program (available from Intelligenetics, Mountain View, Calif.); the AlignX program, version10.3.0 (Invitrogen, Carlsbad, Calif.) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. Gene 73:237-244 (1988); Higgins et al. CABIOS 5:151-153 (1989); Corpet et al., *Nucleic Acids Res.* 16:10881-90 (1988); Huang et al. CABIOS 8:155-65 (1992); and Pearson et al., *Meth. Mol. Biol.* 24:307-331 (1994). The BLAST programs of Altschul et al. *J. Mol. Biol.* 215:403-410 (1990) are based on the algorithm of Karlin and Altschul (1990) supra.

Polynucleotides homologous to a reference sequence can be identified by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in references cited below (e.g., Sambrook et al., Molecular Cloning: A Laboratory Manual, 2nd Ed., Vol. 1-3, Cold Spring Harbor Laboratory, Cold Spring Harbor, N.Y. ("Sambrook") (1989); Berger and Kimmel, Guide to Molecular Cloning Techniques, Methods in Enzymology, vol. 152 Academic Press, Inc., San Diego, Calif. ("Berger and Kimmel") (1987); and Anderson and Young, "Quantitative Filter Hybridisation." In: Hames and Higgins, ed., Nucleic Acid Hybridisation, A Practical Approach. Oxford, TRL Press, 73-111 (1985)).

Encompassed by the disclosure are polynucleotide sequences that are capable of hybridizing to the disclosed polynucleotide sequences and fragments thereof under various conditions of stringency (see, for example, Wahl and Berger, *Methods Enzymol.* 152: 399-407 (1987); and Kimmel, *Methods Enzymo.* 152: 507-511, (1987)). Full length cDNA, homologs, orthologs, and paralogs of polynucleotides of the present disclosure may be identified and isolated using well-known polynucleotide hybridization methods.

Vectors for Expressing Polynucleotides

Each polynucleotide of the present disclosure may be incorporated into an expression vector. "Expression vector" or "vector" refers to a compound and/or composition that transduces, transforms, or infects a host cell, thereby causing the cell to express polynucleotides and/or proteins other than those native to the cell, or in a manner not native to the cell. An "expression vector" contains a sequence of polynucleotides (ordinarily RNA or DNA) to be expressed by the host cell. Optionally, the expression vector also includes materials to aid in achieving entry of the polynucleotide into the host cell, such as a virus, liposome, protein coating, or the like. The expression vectors contemplated for use in the present disclosure include those into which a polynucleotide sequence can be inserted, along with any preferred or required operational elements. Further, the expression vector must be one that can be transferred into a host cell and replicated therein. Preferred expression vectors are plasmids, particularly those with restriction sites that have been well-documented and that contain the operational elements preferred or required for transcription of the polynucleotide sequence. Such plasmids, as well as other expression vectors, are well-known in the art.

Incorporation of the individual polynucleotides may be accomplished through known methods that include, for example, the use of restriction enzymes (such as BamHI, EcoRI, HhaI, XhoI, XmaI, and so forth) to cleave specific sites in the expression vector, e.g., plasmid. The restriction enzyme produces single stranded ends that may be annealed to a polynucleotide having, or synthesized to have, a terminus with a sequence complementary to the ends of the cleaved expression vector. Annealing is performed using an appropriate enzyme, e.g., DNA ligase. As will be appreciated by those of ordinary skill in the art, both the expression vector and the desired polynucleotide are often cleaved with the same restriction enzyme, thereby assuring that the ends of the expression vector and the ends of the polynucleotide are complementary to each other. In addition, DNA linkers may be used to facilitate linking of polynucleotide sequences into an expression vector.

A series of individual polynucleotides can also be combined by utilizing methods that are known in the art (e.g., U.S. Pat. No. 4,683,195). For example, each of the desired polynucleotides can be initially generated in a separate PCR. Thereafter, specific primers are designed such that the ends of the PCR products contain complementary sequences. When the PCR products are mixed, denatured, and reannealed, the strands having the matching sequences at their 3' ends overlap and can act as primers for each other. Extension of this overlap by DNA polymerase produces a molecule in which the original sequences are "spliced" together. In this way, a series of individual polynucleotides may be "spliced" together and subsequently transduced into a host cell simultaneously. Thus, expression of each of the plurality of polynucleotides is affected.

Individual polynucleotides, or "spliced" polynucleotides, are then incorporated into an expression vector. The present disclosure is not limited with respect to the process by which the polynucleotide is incorporated into the expression vector. Those of ordinary skill in the art are familiar with the necessary steps for incorporating a polynucleotide into an expression vector. A typical expression vector contains the desired polynucleotide preceded by one or more regulatory regions, along with a ribosome binding site, e.g., a nucleotide sequence that is 3-9 nucleotides in length and located 3-11 nucleotides upstream of the initiation codon in *E. coli*. See Shine and Dalgarno (1975) Nature 254(5495):34-38 and Steitz (1979) Biological Regulation and Development (ed. Goldberger, R. F.), 1:349-399 (Plenum, New York).

The term "operably linked" as used herein refers to a configuration in which a control sequence is placed at an appropriate position relative to the coding sequence of the DNA sequence or polynucleotide such that the control sequence directs the expression of a polypeptide.

Regulatory regions include, for example, those regions that contain a promoter and an operator. A promoter is operably linked to the desired polynucleotide, thereby initiating transcription of the polynucleotide via an RNA polymerase enzyme. An operator is a sequence of polynucleotides adjacent to the promoter, which contains a protein-binding domain where a repressor protein can bind. In the absence of a repressor protein, transcription initiates through the promoter. When present, the repressor protein specific to the protein-binding domain of the operator binds to the operator, thereby inhibiting transcription. In this way, control of transcription is accomplished, based upon the particular regulatory regions used and the presence or absence of the corresponding repressor protein. Examples include lactose promoters (LacI repressor protein changes conformation when contacted with lactose, thereby preventing the LacI repressor protein from binding to the operator) and tryptophan promoters (when complexed with tryptophan, TrpR repressor protein has a conformation that binds the operator; in the absence of tryptophan, the TrpR repressor protein has a conformation that does not bind to the operator). Another example is the tac promoter (see de Boer et al., (1983) Proc Natl Acad Sci USA 80(1):21-25).

Methods of producing host cells of the disclosure may include the introduction or transfer of the expression vectors containing recombinant nucleic acids of the disclosure into the host cell. Such methods for transferring expression vectors into host cells are well-known to those of ordinary skill in the art. For example, one method for transforming cells with an expression vector involves a calcium chloride treatment where the expression vector is introduced via a calcium precipitate. Other salts, e.g., calcium phosphate, may also be used following a similar procedure. In addition, electroporation (i.e., the application of current to increase the permeability of cells to nucleic acid sequences) may be used to transfect the host cell. Cells also may be transformed through the use of spheroplasts (Schweizer, M, Proc. Natl. Acad. Sci., 78: 5086-5090 (1981). Also, microinjection of the nucleic acid sequences provides the ability to transfect host cells. Other means, such as lipid complexes, liposomes, and dendrimers, may also be employed. Those of ordinary skill in the art can transfect a host cell with a desired sequence using these or other methods.

In some cases, cells are prepared as protoplasts or spheroplasts prior to transformation. Protoplasts or spheroplasts may be prepared, for example, by treating a cell having a cell wall with enzymes to degrade the cell wall. Fungal cells may be treated, for example, with chitinase.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host, is integrated into the genome and replicated together with the chromosome(s) into which it has been integrated. Furthermore, a single vector or plasmid or two or more vectors or plasmids that together contain the total DNA to be introduced into the genome of the host, or a transposon may be used.

The vectors preferably contain one or more selectable markers which permit easy selection of transformed host cells. A selectable marker is a gene the product of which provides, for example, biocide or viral resistance, resistance to heavy metals, prototrophy to auxotrophs, and the like. Selection of bacterial cells may be based upon antimicrobial resistance that has been conferred by genes such as the amp, gpt, neo, and hyg genes.

Selectable markers for use in fungal host cells may include, for example, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof.

The vectors may contain an element(s) that permits integration of the vector into the host's genome or autonomous replication of the vector in the cell independent of the genome.

For integration into the host genome, the vector may rely on the gene's sequence or any other element of the vector for integration of the vector into the genome by homologous or nonhomologous recombination. Alternatively, the vector may contain additional nucleotide sequences for directing integration by homologous recombination into the genome of the host. The additional nucleotide sequences enable the vector to be integrated into the host genome at a precise location(s) in the chromosome(s). To increase the likelihood of integration at a precise location, the integrational elements should contain a sufficient number of nucleic acids, such as 100 to 10,000 base pairs, 400 to 10,000 base pairs, or 800 to 10,000 base pairs, which are highly homologous with the corresponding target sequence to enhance the probability of homologous recombination. The integrational elements may be any sequence that is homologous with the target sequence in the genome of the host. Furthermore, the integrational elements may be non-encoding or encoding nucleotide sequences. On the other hand, the vector may be integrated into the genome of the host by non-homologous recombination.

For autonomous replication, the vector may further contain an origin of replication enabling the vector to replicate autonomously in the host in question. The origin of replication may be any plasmid replicator mediating autonomous replication which functions in a cell. The term "origin of replication" or "plasmid replicator" is defined herein as a sequence that enables a plasmid or vector to replicate in vivo.

Various promoters for regulation of expression of a recombinant nucleic acid of the disclosure in a vector are well-known in the art and include, for example, constitutive promoters and inducible promoters. Promoters are described, for example, in Sambrook, et al. Molecular Cloning: A Laboratory Manual, 3rd edition, Cold Spring Harbor Laboratory Press, (2001). Promoter can be viral, bacterial, fungal, mammalian, or plant promoters. Additionally, promoters can be constitutive promoters, inducible promoters, environmentally regulated promoters, or developmentally regulated promoters. Examples of suitable promoters for regulating recombinant nucleic acid of the disclosure may include, for example, the *N. crassa* ccg-1 constitutive promoter, which is responsive to the *N. crassa* circadian rhythm and nutrient conditions; the *N. crassa* gpd-1 (glyceraldehyde 3-phosphate dehydrogenase-1) strong constitutive promoter; the *N. crassa* vvd (light) inducible promoter; the *N. crassa* qa-2 (quinic acid) inducible promoter; the *Aspergillus nidulans* gpdA promoter; the *Aspergillus nidulans* trpC constitutive promoter; the *N. crassa* tef-1 (transcription elongation factor) highly constitutive promoter; and the *N. crassa* xlr-1 (XlnR homolog) promoter, which is used frequently in *Aspergillus* species. In some embodiments, expression of a recombinant polypeptide of the disclosure is under the control of a heterologous promoter. In some preferred embodiments, the promoter is the TEF1 promoter to achieve overexpression of a polypeptide.

More than one copy of a gene may be inserted into the host to increase production of the gene product. An increase in the copy number of the gene can be obtained by integrating at least one additional copy of the gene into the host genome or by including an amplifiable selectable marker gene with the nucleotide sequence where cells containing amplified copies of the selectable marker gene, and thereby additional copies of the gene, can be selected for by cultivating the cells in the presence of the appropriate selectable agent.

The procedures used to ligate the elements described above to construct the recombinant expression vectors of the present disclosure are well-known to one skilled in the art (see, e.g., Sambrook et al., 1989, supra). When only a single expression vector is used (without the addition of an intermediate), the vector will contain all of the nucleic acid sequences necessary.

Host Cells Having Modified Polypeptide Activity

Recombinant host cells of the present disclosure having modified polypeptide activity are capable of producing sugar acids, such as cellobionate, and commodity chemicals from cellulose or cellulosic biomass. The ability to metabolize cellulose is a trait exhibited by lignocellulolytic cells, and thus host cells of the present disclosure are preferably lignocellulolytic cells. As disclosed herein, the lignocellulolytic cells may be either aerobic cells or anaerobic cells. In certain preferred embodiments, the lignocellulolytic cells are aerobic cells.

Lignocellulolytic cells of the present disclosure produce enzymes that degrade lignocellulose or components thereof. The lignocellulolytic cells may degrade the lignocellulose or components thereof under aerobic (i.e., oxygen rich), or anaerobic (i.e., oxygen deficient) conditions. In certain embodiments, the lignocellulolytic cells of the present disclosure are capable of pretreating lignocellulosic biomass. Such lignocellulolytic cells simultaneously degrade lignin, solubilize lignin, or change lignin to a revised form, such as de-methylized lignin. Lignin is an energy-rich compound that can be utilized for energy production (e.g. electricity). In other embodiments, lignocellulolytic cells of the present disclosure produce one or more cellulases, hemicellulases, lignin-solubilizing enzymes, or combinations thereof. In certain embodiments, the one or more hemicellulases and/or lignin-solubilizing enzymes are recombinantly expressed in the lignocellulolytic cells. Accordingly, lignocellulolytic cells of the present disclosure can produce monosaccharides (e.g., glucose) and cellodextrins (e.g., cellobiose, cellotriose, cellotetrose, cellopentose, etc.) from lignocellulosic biomass. Additionally, lignocellulolytic cells of the present disclosure can also produce hemicellulose oligosaccharides, such as xylobiose, from lignocellulosic biomass.

Lignocellulolytic cells of the present disclosure may include, for example, fungi and bacteria. Suitable lignocellulolytic fungi of the present disclosure may include, for example, White Rot Fungi, Brown Rot Fungi, Soft Rot Fungi, and ascomycetes fungi. Suitable lignocellulolytic bacteria of the present disclosure may include, for example, *Clostridium* sp. and *Thermanaerobacterium* sp. Additional examples of suitable host cells may include, for example, *Trichoderma reesei, Clostridium thermocellum, Clostridium papyrosolvens* C7*, Podospera anserine, Chaetomium globosum, Aspergillus nidulans, Aspergillus niger, Aspergillus oryzae, Saccharomyces cerevisiae, Schizosaccharomyces pombe, Phanerochaete chrysosporium, Sporotrichum thermophile* (*Myceliophthora thermophila*)*, Gibberella zeae, Sclerotinia sclerotiorum, Botryotinia fuckelian, Aspergillus niger, Thielavia terrestris, Fusarium* spp.*, Rhizopus* spp.*, Neocallimastix frontalis, Orpinomyces* sp.*, Piromyces* sp.*, Penicillium chrysogenum* cells*, Schizophyllum commune, Postia placenta, Acremonium cellulolyticus, Yarrowia lipolytica, Hansenula polymorpha, Kluyveromyces lactis, Pichia pastoris, Chrysosporium lucknowense, Aspergillus* sp.*, Trichoderma* sp.*, Caldocellulosiruptor* sp.*, Butyrivibrio* sp., *Butyrivibrio* sp., *Eubacterium* sp., *Clostridium* sp., *Bacteroides* sp., *Acetivibrio* sp., *Thermoactinomyces* sp., *Caldibacillus* sp., *Bacillus* sp., *Acidothermus* sp., *Cellulomonas* sp., *Micromonospora* sp., *Actinoplanes* sp., *Streptomyces* sp., *Thermobifida* sp., *Thermomonospora* sp., *Microbispora* sp., *Microbispora* sp., *Fibrobacter* sp., *Sporocytophaga* sp., *Cytophaga* sp., *Flavobacterium* sp., *Achromobacter* sp., *Xanthomonas* sp., *Cellvibrio* sp., *Pseudomonas* sp., *Myxobacter* sp., *Clostridium phytofermentans*, *Clostridium japonicas*, and *Thermoanaerobacterium saccharolyticum* cells.

In certain embodiments, host cells of the present disclosure are filamentous fungal cells including, for example, *Neurospora*, *Trichoderma*, and *Aspergillus* cells. In certain preferred embodiments, the filamentous fungal cells are *Neurospora crassa* cells.

Host cells of the present disclosure are living biological cells that are manipulated to alter, for example, the activity of one or more polypeptides in the cell. For example, host cells may be transformed via insertion of recombinant DNA or RNA. Such recombinant DNA or RNA can be in an expression vector. Further, host cells may be subject to mutagenesis to induce mutations in polypeptide-encoding polynucleotides. Host cells that have been genetically modified are recombinant host cells.

The host cells of the present disclosure may be genetically modified. For example, recombinant nucleic acids may have been introduced into the host cells or the host cells may have mutations introduced into endogenous and/or exogenous polynucleotides, and as such the genetically modified host cells do not occur in nature. A suitable host cell may be, for example, one that is capable of expressing one or more nucleic acid constructs for different functions such as, for example, recombinant protein expression and/or targeted gene silencing.

"Recombinant nucleic acid" or "heterologous nucleic acid" or "recombinant polynucleotide", "recombinant nucleotide" or "recombinant DNA" as used herein refers to a polymer of nucleic acids where at least one of the following is true: (a) the sequence of nucleic acids is foreign to (i.e., not naturally found in) a given host cell; (b) the sequence may be naturally found in a given host cell, but is expressed in an unnatural (e.g., greater than expected) amount; or (c) the sequence of nucleic acids contains two or more subsequences that are not found in the same relationship to each other in nature. For example, regarding instance (c), a recombinant nucleic acid sequence will have two or more sequences from unrelated genes arranged to make a new functional nucleic acid. For example, the present disclosure describes the introduction of an expression vector into a host cell, where the expression vector contains a nucleic acid sequence coding for a protein that is not normally found in a host cell or contains a nucleic acid coding for a protein that is normally found in a cell but is under the control of different regulatory sequences. With reference to the host cell's genome, then, the nucleic acid sequence that codes for the protein is recombinant. As used herein, the term "recombinant polypeptide" refers to a polypeptide generated from a "recombinant nucleic acid" or "heterologous nucleic acid" or "recombinant polynucleotide", "recombinant nucleotide" or "recombinant DNA" as described above.

In some embodiments, the host cell naturally produces any of the polypeptides of the present disclosure. In some embodiments, the genes encoding the desired polypeptides may be heterologous to the host cell or these genes may be endogenous to the host cell but are operatively linked to heterologous promoters and/or control regions that result in, for example, the higher expression of the gene(s) in the host cell or the decreased expression of the gene(s) in the host cell.

In some embodiments, host cells of the present disclosure may be modified to facilitate the metabolism of cellulose. For example, host cells of the present disclosure may be modified to contain one or more cellodextrin transporters. Cellodextrins are glucose polymers of varying length and include, for example, cellobiose (2 glucose monomers), cellotriose (3 glucose monomers), cellotetraose (4 glucose monomers), cellopentaose (5 glucose monomers), and cellohexaose (6 glucose monomers). A cellodextrin transporter is any transmembrane protein that transports a cellodextrin molecule from outside of the cell to the inside of the cell and/or from inside of the cell to outside of the cell. Examples of suitable cellodextrin transporters may include, for example, NCU00801, NCU00809, NCU8114, XP_001268541.1, and LAC2.

Methods of Modifying Polypeptide Activity

Host cells of the present disclosure have modified polypeptide activity as compared to a corresponding control cell, such as a corresponding wild type cell, to facilitate and/or increase the production of sugar acids. Polypeptide activity may be modified such that one or more polypeptides of the present disclosure have increased activity or decreased activity. In some embodiments, a host cell may have one or more polypeptides with increased activity as well as one or more polypeptides with decreased activity. Methods of modifying (e.g. increasing and/or decreasing) the activity of one or more polypeptides of the present disclosure are well-known in the art and are described herein.

Decreased Polypeptide Activity

Host cells of the present disclosure may contain one or more polypeptides with decreased activity as compared to a corresponding control cell, such as a wild type cell. In some embodiments, one or more β-glucosidases, cellobionate phosphorylases, CRE-1 proteins, ACE-1 proteins, and/or MUS51 proteins have decreased activity in a host cell as compared to a corresponding control cell. Methods of decreasing the expression, abundance, and/or activity of a polypeptide are well-known in the art and are described herein.

In some embodiments, decreasing activity of a polypeptide involves overexpressing a polypeptide that is an inhibitor of the polypeptide. Host cells may overexpress an inhibitor that inhibits the expression and/or activity of one or more β-glucosidases, cellobionate phosphorylases, CRE-1 proteins, ACE-1 proteins, and/or MUS51 proteins of the present disclosure. In some embodiments, a recombinant β-glucosidase, cellobionate phosphorylase, CRE-1 protein, ACE-1 protein, and/or MUS51 protein may be expressed in host cells such that the recombinant polypeptide interferes with and decreases the activity of the endogenous polypeptide.

In some embodiments, decreasing the activity of a polypeptide such as, for example, one or more β-glucosidases, cellobionate phosphorylases, CRE-1 proteins, ACE-1 proteins, and/or MUS51 proteins involves decreasing the expression of a nucleic acid encoding the polypeptide.

Decreasing the expression of a nucleic acid may be accomplished by introducing a genetic mutation into a target nucleic acid. Mutagenesis approaches may be used to disrupt or "knockout" the expression of a target gene by generating mutations. In some embodiments, the mutagenesis results in a partial deletion of the target gene. In other embodiments, the mutagenesis results in a complete deletion of the target gene. Methods of mutagenizing microorganisms are well known in the art and include, for example, random mutagenesis and site-directed mutagenesis to induce mutations. Examples of methods of random mutagenesis include, for example, chemical mutagenesis (e.g., using ethane methyl sulfonate), insertional mutagenesis, and irradiation.

One method for reducing or inhibiting the expression of a target gene is by genetically modifying the target gene and introducing it into the genome of a host cell to replace the wild-type version of the gene by homologous recombination (for example, as described in U.S. Pat. No. 6,924,146).

Another method for reducing or inhibiting the expression of a target gene is by insertion mutagenesis using the T-DNA of *Agrobacterium tumefaciens*, or transposons (see Winkler et al., Methods Mol. Biol. 82:129-136, 1989, and Martienssen Proc. Natl. Acad. Sci. 95:2021-2026, 1998). After generating the insertion mutants, the mutants can be screened to identify those containing the insertion in a target gene. Methods to disrupt a target gene by insertional mutagenesis are described in for example, U.S. Pat. No. 5,792,633. Methods to disrupt a target gene by transposon mutagenesis are described in for example, U.S. Pat. No. 6,207,384.

A further method to disrupt a target gene is by use of the cre-lox system (for example, as described in U.S. Pat. No. 4,959,317).

Another method to disrupt a target gene is by use of PCR mutagenesis (for example, as described in U.S. Pat. No. 7,501,275).

Endogenous gene expression may also be reduced or inhibited by means of RNA interference (RNAi), which uses a double-stranded RNA having a sequence identical or similar to the sequence of the target gene. RNAi may include the use of micro RNA, such as artificial miRNA, to suppress expression of a gene.

RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA.

Thus, in some embodiments, reduction or inhibition of gene expression is achieved using RNAi techniques. For example, to achieve reduction or inhibition of the expression of a DNA encoding a protein using RNAi, a double-stranded RNA having the sequence of a DNA encoding the protein, or a substantially similar sequence thereof (including those engineered not to translate the protein) or fragment thereof, is introduced into a host cell of interest. As used herein, RNAi and dsRNA both refer to gene-specific silencing that is induced by the introduction of a double-stranded RNA molecule, see e.g., U.S. Pat. Nos. 6,506,559 and 6,573,099, and includes reference to a molecule that has a region that is double-stranded, e.g., a short hairpin RNA molecule. The resulting cells may then be screened for a phenotype associated with the reduced expression of the target gene, e.g., reduced cellulase expression, and/or by monitoring steady-state RNA levels for transcripts of the target gene. Although the sequences used for RNAi need not be completely identical to the target gene, they may be at least 70%, 80%, 90%, 91%, 92%, 93%, 94%, 95%, 96%, 97%, 98%, 99%, or more identical to the target gene sequence. See, e.g., U.S. Patent Application Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Application Publication No. 2003/0221211.

The RNAi nucleic acids may encompass the full-length target RNA or may correspond to a fragment of the target RNA. In some cases, the fragment will have fewer than 100, 200, 300, 400, or 500 nucleotides corresponding to the target sequence. In addition, in some aspects, these fragments are at least, e.g., 50, 100, 150, 200, or more nucleotides in length. Interfering RNAs may be designed based on short duplexes (i.e., short regions of double-stranded sequences). Typically, the short duplex is at least about 15, 20, or 25-50 nucleotides in length (e.g., each complementary sequence of the double stranded RNA is 15-50 nucleotides in length), often about 20-30 nucleotides, e.g., 20, 21, 22, 23, 24, 25, 26, 27, 28, 29, or 30 nucleotides in length. In some cases, fragments for use in RNAi will correspond to regions of a target protein that do not occur in other proteins in the organism or that have little similarity to other transcripts in the organism, e.g., selected by comparison to sequences in analyzing publicly-available sequence databases. Similarly, RNAi fragments may be selected for similarity or identity with a conserved sequence of a gene family of interest, such as those described herein, so that the RNAi targets multiple different gene transcripts containing the conserved sequence.

RNAi may be introduced into a host cell as part of a larger DNA construct. Often, such constructs allow stable expression of the RNAi in cells after introduction, e.g., by integration of the construct into the host genome. Thus, expression vectors that continually express RNAi in cells transfected with the vectors may be employed for this disclosure. For example, vectors that express small hairpin or stem-loop structure RNAs, or precursors to microRNA, which get processed in vivo into small RNAi molecules capable of carrying out gene-specific silencing (Brummelkamp et al, Science 296:550-553, (2002); and Paddison, et al., Genes & Dev. 16:948-958, (2002)) can be used. Post-transcriptional gene silencing by double-stranded RNA is discussed in further detail by Hammond et al., Nature Rev Gen 2: 110-119, (2001); Fire et al., Nature 391: 806-811, (1998); and Timmons and Fire, Nature 395: 854, (1998).

Methods for selection and design of sequences that generate RNAi are well-known in the art (e.g. U.S. Pat. Nos. 6,506,559; 6,511,824; and 6,489,127).

A reduction or inhibition of gene expression in a host cell of a target gene may also be obtained by introducing into host cells antisense constructs based on a target gene nucleic acid sequence. For antisense suppression, a target sequence is arranged in reverse orientation relative to the promoter sequence in the expression vector. The introduced sequence need not be a full length cDNA or gene, and need not be identical to the target cDNA or a gene found in the cell to be transformed. Generally, however, where the introduced sequence is of shorter length, a higher degree of homology to the native target sequence is used to achieve effective antisense suppression. In some aspects, the introduced antisense sequence in the vector will be at least 30 nucleotides in length, and improved antisense suppression will typically be observed as the length of the antisense sequence increases. In some aspects, the length of the antisense sequence in the vector will be greater than 100 nucleotides. Transcription of an antisense construct as described results in the production of RNA molecules that are the reverse complement of mRNA molecules transcribed from an endogenous target gene. Suppression of a target gene expression can also be achieved using a ribozyme. The production and use of ribozymes are disclosed in U.S. Pat. Nos. 4,987,071 and 5,543,508.

Expression cassettes containing nucleic acids that encode target gene expression inhibitors, e.g., an antisense or siRNA, can be constructed using methods well known in the art. Constructs include regulatory elements, including promoters and other sequences for expression and selection of cells that express the construct. Typically, fungal and/or bacterial transformation vectors include one or more cloned coding sequences (genomic or cDNA) under the transcriptional control of 5' and 3' regulatory sequences and a dominant selectable marker. Such transformation vectors typically also contain a promoter (e.g., a regulatory region controlling inducible or constitutive, environmentally- or developmentally-regulated expression), a transcription initiation start site, an RNA processing signal (such as intron splice sites), a transcription termination site, and/or a polyadenylation signal.

In certain embodiments, a portion of the target nucleic acid may be modified, such as the region encoding the catalytic domain, the coding region, or a control sequence required for expression of the coding region. Such a control sequence of the gene may be a promoter sequence or a functional part thereof, i.e., a part that is sufficient for affecting expression of the gene. For example, a promoter sequence may be inactivated resulting in no expression or a weaker promoter may be substituted for the native promoter sequence to reduce expression of the coding sequence. Other control sequences for possible modification may include, for example, a leader sequence, a propeptide sequence, a signal sequence, a transcription terminator, and a transcriptional activator.

Increased Polypeptide Activity

Host cells of the present disclosure may contain one or more polypeptides with increased expression and/or activity as compared to a corresponding control cell, such as a corresponding wild type cell. In some embodiments, host cells of the disclosure contain a recombinant nucleic acid encoding a recombinant polypeptide of the disclosure such as, for example, a recombinant laccase and/or a recombinant cellobiose dehydrogenase. In certain embodiments, the recombinant nucleic acid is mis-expressed in the host cell (e.g., constitutively expressed, inducibly expressed, etc.) such that mis-expression results in increased polypeptide activity as compared to a corresponding control cell. In some embodiments, a host cell that contains a recombinant nucleic acid encoding a recombinant polypeptide contains a greater amount of the polypeptide than a corresponding control cell that does not contain the corresponding recombinant nucleic acid. When a protein or nucleic acid is produced or maintained in a host cell at an amount greater than normal, the protein or nucleic acid is "overexpressed." In some embodiments, host cells of the disclosure overexpress a polypeptide such as, for example, a laccase and/or cellobiose dehydrogenase. Host cells may overexpress one or more of a laccase and/or cellobiose dehydrogenase polypeptide such that the activity of one or more of these proteins is increased in the host cell as compared to a corresponding control cell. The corresponding control cell may be, for example, a cell that does not overexpress one or more of the polypeptides overexpressed in the host cell, such as a wild type cell. Various control cells will be readily apparent to one of skill in the art.

Various methods of increasing the expression of a polypeptide are known in the art. For example, other genetic regions involved in controlling expression of the nucleic acid encoding the polypeptide, such as an enhancer sequence, may be modified such that expression of the nucleic acid is increased. The level of expression of a nucleic acid may be assessed by measuring the level of mRNA encoded by the gene, and/or by measuring the level or activity of the polypeptide encoded by the nucleic acid.

In some embodiments, host cells overexpress a polypeptide that is an activator of one or more of a laccase and/or cellobiose dehydrogenase polypeptide. Overexpression of an activator polypeptide may lead to increased abundance and activity of the polypeptide activated by the activator. The activator may increase expression of one or more of a laccase and/or cellobiose dehydrogenase polypeptide. The activator may increase activity of one or more of a laccase and/or cellobiose dehydrogenase polypeptide.

Increasing the abundance of a polypeptide of the disclosure such as, for example, a laccase and/or cellobiose dehydrogenase polypeptide, to increase polypeptide activity may be achieved by overexpressing the polypeptide. Other methods of increasing abundance of a polypeptide are known in the art. For example, decreasing degradation of the polypeptide by cellular degradation machinery, such as the proteasome, may increase the stability and the abundance of the polypeptide. The polypeptides may be genetically modified such that they have increased resistance to cellular proteolysis, but exhibit no change in molecular activity. Polypeptides that are inhibitors of cellular factors involved in the degradation of one or more of a laccase and/or cellobiose dehydrogenase polypeptides may be introduced into host cells to increase abundance of the one or more polypeptides. Further, host cells may be treated with chemical inhibitors of the proteasome, such as cycloheximide, to increase the abundance of one or more polypeptides of the disclosure.

Methods of Producing Sugar Acids

Host cells of the present disclosure having modified polypeptide activity are capable of producing sugar acids, such as cellooligosaccharide aldonates, from cellulose or cellulosic materials. Host cells of the present disclosure are capable of metabolizing cellulose (lignocellulolytic cells) and may be able to do so based on the presence of endogenous genetic machinery that facilitates cellulose metabolism, or may be genetically engineered to metabolize cellulose. Thus, host cells of the present disclosure shall express one or more of the following enzymes: cellulases, xylanases, ligninases, oxidases, dehydrogenases, and laccases. Once products from the breakdown of cellulose, such as cellobiose, are generated, these breakdown products may be used for the production of sugar acids by host cells of the present disclosure.

Methods of the present disclosure involve the use of host cells having modified polypeptide activity to produce sugar acids, such as cellobionate, and commodity chemicals from cellulose or cellulosic biomass. Sugar acids, also known as saccharide aldonic acids (SAAs), refer to molecules in which the CHO aldehyde functional group of a saccharide has been replaced with a carboxylic acid functional group (COOH). Sugar acids can be divided into four general categories: (1) oligosaccharide aldonic acid (OAA), (2) di-saccharide aldonic acid (DAA), (3) monosaccharide aldonic acid (MAA), and (4) heteropolysaccharide aldonic acid (HSAA). Examples of oligosaccharide aldonic acid (OAA) include: cellotrionic acid, cellotetraonic acid; cello-heptonic acid, xylotrionic acid, and xylopentaonic acid. Examples of di-saccharide aldonic acid (DAA) include: cellobionic acid (CBA), xylobionic acid, galactonic acid, 4-O-β-D-galactopyranosylgluconic acid, and 6-O-β-D-galactopyranosylgluconic acid. Examples of monosaccharide aldonic acids (MAA) include gluconic acid, xylonic acid, galactonic acid, arabinic acid, and mannonic acid. An example of HSAA is 4-O-methyl-α-D-glucuronopyranosyl acid.

In the case of DAA, OAA and HSAA, the connection between sugar units and between the sugar and the end of the aldonic acid could be straight-chain or branched-chain. For example, gluconic acids could be connected glycosidically on the oxygen atoms in the 1-, 3-, 4- or 6-position of a sugar unit. There could be any combination of sugar and terminal aldonic acid.

In aqueous solution, sugar acids generally exist in salt form. Examples of inorganic and organic salts are ammonium, lithium, sodium, magnesium, calcium and aluminum salts, as well as the salts with ethanolamine, triethanolamine, morpholine, pyridine, and piperidine.

The methods of the present disclosure involve culturing a host cell of the present disclosure in a cellulose-containing medium, where the host cell produces a sugar acids a sugar acid from the cellulose. Host cells of the present disclosure such as, for example, host cells having decreased activity of one or more β-glucosidases, cellobionate phosphorylases, CRE-1 proteins, ACE-1 proteins, and/or MUS51 proteins, and/or increased expression or activity of one or more laccases and/or cellobiose dehydrogenases, are cultured in a growth medium under conditions suitable for the production of sugar acids from cellulose by the host cell.

Host cells of the present disclosure are capable of utilizing cellulose as a carbon source in a growth/culture medium. According to some aspects of the disclosure, the culture media contains cellulose or a source of cellulose as a carbon source for the host cell. "Carbon source" generally refers to a substrate or compound suitable to be used as a source of carbon for cell growth, such as, for example, cellulose or a source of cellulose. In some embodiments, the culture media contains only cellulose or a source of cellulose as the sole carbon source. In other embodiments, the culture media may contain additional carbon sources other than cellulose. Carbon sources may be in various forms such as, for example, polymers, carbohydrates, acids, alcohols, aldehydes, ketones, amino acids, peptides, etc. These include, for example, various monosaccharides, oligosaccharides, polysaccharides, a biomass polymer such as cellulose or hemicellulose, xylose, arabinose, disaccharides, such as sucrose, saturated or unsaturated fatty acids, succinate, lactate, acetate, ethanol, etc., or mixtures thereof. In addition to an appropriate carbon source, culture media may contain suitable minerals, salts, cofactors, buffers and other components, known to those skilled in the art, suitable for the growth of the cultures and promotion of the pathways involved in the production of sugar acids. Standard culture environments for microorganisms, such as those used in methods of the present disclosure, are well-known in the art and are described herein.

Sources of cellulose are well-known in the art and are described herein. For example, cellulose may be purchased commercially and added to culture media as a carbon source. The source of cellulose may be a material that contains cellulose or whose breakdown releases cellulose. As used herein, a "cellulose-containing material" is any material that contains or is capable of generating cellulose, including biomass, such as biomass containing plant material. Biomass suitable for use with the currently disclosed methods include various cellulose-containing materials such as, for example, *Miscanthus*, switchgrass, cord grass, rye grass, reed canary grass, elephant grass, common reed, wheat straw, barley straw, canola straw, oat straw, corn stover, soybean stover, oat hulls, sorghum, rice hulls, rye hulls, wheat hulls, sugarcane bagasse, copra meal, copra pellets, palm kernel meal, corn fiber, Distillers Dried Grains with Solubles (DDGS), Blue Stem, corncobs, pine wood, birch wood, willow wood, aspen wood, poplar wood, energy cane, waste paper, sawdust, forestry wastes, municipal solid waste, waste paper, crop residues, other grasses, and other woods. The source of cellulose may require a pre-treatment to generate and/or liberate cellulose or cellulose breakdown products such as, for example, treatment with high temperature or pressure. Such treatments are well-known to those skilled in the art.

In some embodiments, host cells of the present disclosure are cultured in the presence of exogenously added laccase and/or cellobiose dehydrogenase enzymes. These enzymes may be purchased from a commercial vendor, or they may be recombinantly expressed and purified as will be readily understood by one of skill in the art. In some embodiments, such as those embodiments where exogenous laccase is added to the culture media, the culture media may further contain a compounds which is a redox mediator such as, for example, ABTS (2,2'-azino-bis(3-ethylbenzothiazoline-6-sulphonic acid)).

In some embodiments, after a host cell of the present disclosure has produced a sugar acid, the sugar acid may be precipitated, removed, or substantially purified from the culture media. Methods of substantially purifying sugar acids from culture media are known in the art.

In some embodiments, the methods of the present disclosure involve host cells having an increased sugar acid production rate as compared to a corresponding control cell. Host cells having an increased sugar acid production rate may be those having decreased activity of one or more β-glucosidases, cellobionate phosphorylases, CRE-1 proteins, ACE-1 proteins, and/or MUS51 proteins, and/or increased expression or activity of one or more laccases and/or cellobiose dehydrogenases. The rate of sugar acid production in host cells of the present disclosure may be at least 0.1-fold, at least 0.2-fold, at least 0.3-fold, at least 0.4-fold, at least 0.5-fold, at least 0.6-fold, at least 0.7-fold, at least 0.8-fold, at least 0.9-fold, at least 1-fold, at least 1.25 fold, at least 1.5-fold, at least 1.75-fold, at least 2-fold, at least 2.25-fold, at least 2.5-fold, at least 2.75-fold, at least 3-fold, at least 3.25-fold, at least 3.5-fold, at least 3.75-fold, at least 4-fold, at least 4.25-fold, at least 4.5-fold, at least 4.75-fold, at least 5-fold, at least 5.25-fold, at least 5.5-fold, at least 5.75-fold, at least 6-fold, at least 7-fold, at least 8-fold, at least 9-fold, at least 10-fold, at least 20-fold, or at least 30-fold or more higher than the sugar acid production rate of a corresponding control cell such as, for example, a wild type cell or a cell not having modified polypeptide activity. In some embodiments, the corresponding control cell does not accumulate any sugar acids. In some embodiments, the sugar acid produced by the host cell is cellobionate.

In some embodiments, the methods of the present disclosure involve host cells having a decreased rate of sugar acid consumption as compared to a corresponding control cell. Host cells having a decreased rate of sugar acid consumption may be those having decreased activity of one or more β-glucosidases, cellobionate phosphorylases, CRE-1 proteins, ACE-1 proteins, and/or MUS51 proteins, and/or increased expression or activity of one or more laccases and/or cellobiose dehydrogenases. The consumption of a sugar acid by a host cell of the present disclosure may be reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 99%, or by about 100% as compared to a corresponding control cell such as, for example, a wild type cell or a cell not having modified polypeptide activity. In some embodiments, the consumption of cellobionate by a host cell of the present disclosure is reduced by about 100% as compared to a corresponding control cell.

Methods of measuring the accumulation, production, and/or consumption/degradation rate of a sugar acid by a host cell or a population of cells are well-known in the art and are described herein. For example, determining the sugar acid consumption/degradation rate of a cell or cell population in culture may involve allowing cells to grow in medium containing a sugar acid and measuring the depletion of the sugar acid from the growth medium over time at specified time points and determining the slope of the resulting plotted line to determine sugar consumption/degradation rate (e.g. cellobionate/L/h). Similarly, determining sugar acid accumulation or production may involve culturing a cell or population of cells in a medium containing cellulose and measuring the production of a sugar acid from the cellulose over time at specified time points.

Sugar acids produced using the methods of the present disclosure may be used as starting materials for the production of commodity chemicals, such as fuels or fuel additives. Exemplary commodity chemicals include, for example, alcohol, ethanol, propanol, isopropanol, acetone, butanol, isobutanol, 2-methyl-1-butanol, 3-methyl-1-butanol, phenylethanol, a fatty alcohol, isopentenol, an aldehyde, acetylaldehyde, propionaldehyde, butryaldehyde, isobutyraldehyde, 2-methyl-1-butanal, 3-methyl-1-butanal, phenylacetaldehyde, a fatty aldehyde, a hydrocarbon, an alkane, an alkene, an isoprenoids, a fatty acid, a wax ester, an ethyl ester, hydrogen, and combinations thereof.

EXAMPLES

The following Examples are offered to illustrate provided embodiments and are not intended to limit the scope of the present disclosure.

Example 1: Metabolic Pathway for Direct Sugar Acid and Sugar Oligomer Production from Cellulose This Example demonstrates a pathway for production of sugar acids directly from cellulose. A fungal strain was constructed by deleting various copies of β-glucosidase genes, over-expressing laccase gene, and deleting a cellobionate phosphorylase gene. The engineered fungus was able to directly produce sugar acids (such as cellobionate) directly from cellulose without any exogenous cellulase addition. Sugar acids produced can be used as the starting feedstock for the production of various fuels and chemicals.

Materials and Methods
  Materials
  Wild type *Neurospora crassa* (2489) was obtained from the Fungal Genetics Stock Center (FGSC). The F5 strain used in this study is strain 2489 with six out of seven of its beta-glucosidase (bgl) genes knocked out. Laccase from *Pleurotus ostreatus*, an efficient laccase producer, was obtained from Sigma Aldrich and used in any studies requiring the exogenous addition of laccase.
  2,2'-azino-bis(3-ethylbenzothiazoline-6-sulphonic acid) (ABTS) was obtained from Sigma Aldrich. For experiments requiring exogenous CDH, a recombinant *Pichia pastoris* strain developed by Applicants was used to generate CDH (Zhang et al., 2011).

Strain Construction
  The strain F5Δcre-1 and F5Δacre1 was constructed using the method of targeted gene deletion with marker recycling as previously described (Szewczyk et al., 2013). The F5Δcre-1 and F5 Δacre1 was constructed by genetic crossing (Fan et al., 2012).
  Cellobionate phosphorylase (NdvB) knockout (F5 Δcre-1Δace1ΔndvB) was constructed using the method described using the method of targeted gene deletion with marker recycling as previously described (Szewczyk et al., 2013).

Overexpression of Laccase
  The knock in cassette containing the native laccase gene (NCU04528; Genbank accession # J03505) flanked by the gpdA promoter and trpC terminator from *Aspergillus nidulans* was synthesized and sequence verified by Life Technologies. The region upstream of the gpdA promoter contains a 1020 bp homologous sequence to the 3' end of *N. crassa*'s csr-1 gene, and the region downstream of the trpC terminator contains 1900 bp with homology to the 5' end of the csr-1 gene. The csr-1 gene confers sensitivity to cyclosporin A. Replacing the csr-1 gene with the knock in cassette via homologous recombination renders the strain resistant to cyclosporin A, providing a selection method for homokaryon mutants. 10-day old conidia of the strain F5 Δcre-1Δace1ΔndvB was harvested, filtered through cheese cloth, and washed and centrifuged three times with 50 mL of 1M ice cold sorbitol. The conidia was concentrated to $2.5 \times 10^9$ conidia/mL. 90 μL of cells were mixed with 1000 μg of DNA and chilled on ice for 5 minutes prior to electroporation (0.2 cm cuvette; 1.5 kV/cm; capacitance: 25 uFD; resistance: 600 ohms). Immediately following electroporation, 750 mL of 1M ice cold sorbitol was added to the cuvette, and the suspension was transferred to 2 mL of recovery media containing 1× Vogel's salts and 2% yeast extract. Cells were regenerated in a rotary shaker at 30° C. and 200 rpm for 6 hours. 350 μL of the regenerated solution was spread on plates containing 1× Vogel's salts, 2% yeast extract, 1M sorbitol, 20 g $l^{-1}$ sorbose, 0.5 g $l^{-1}$ fructose, 0.5 g $l^{-1}$ glucose, 5 μg m$L^{-1}$ CsA, and 2% agar. After 4-7 days of growth at 30° C., colonies were transferred to slants (5 μg m$L^{-1}$ CsA, 1× Vogel's, 2% agar) and grown for 4 days at 30° C. Positive transformants were selected by monitoring the extracellular expression of laccase for transformants grown on 1× Vogel's salts with 20 g/L glucose. The parent strain does not produce any detectable laccase under these conditions. Laccase expression was measured by following the increase in absorbance of ABTS according to a previously established method (Baminger et al., 2001). One unit of laccase activity was defined as the amount of enzyme oxidizing 1 mmol of ABTS per min. The strains are designated as the label F5 Δcre-1Δace1ΔndvB+lac.

Figure 4:
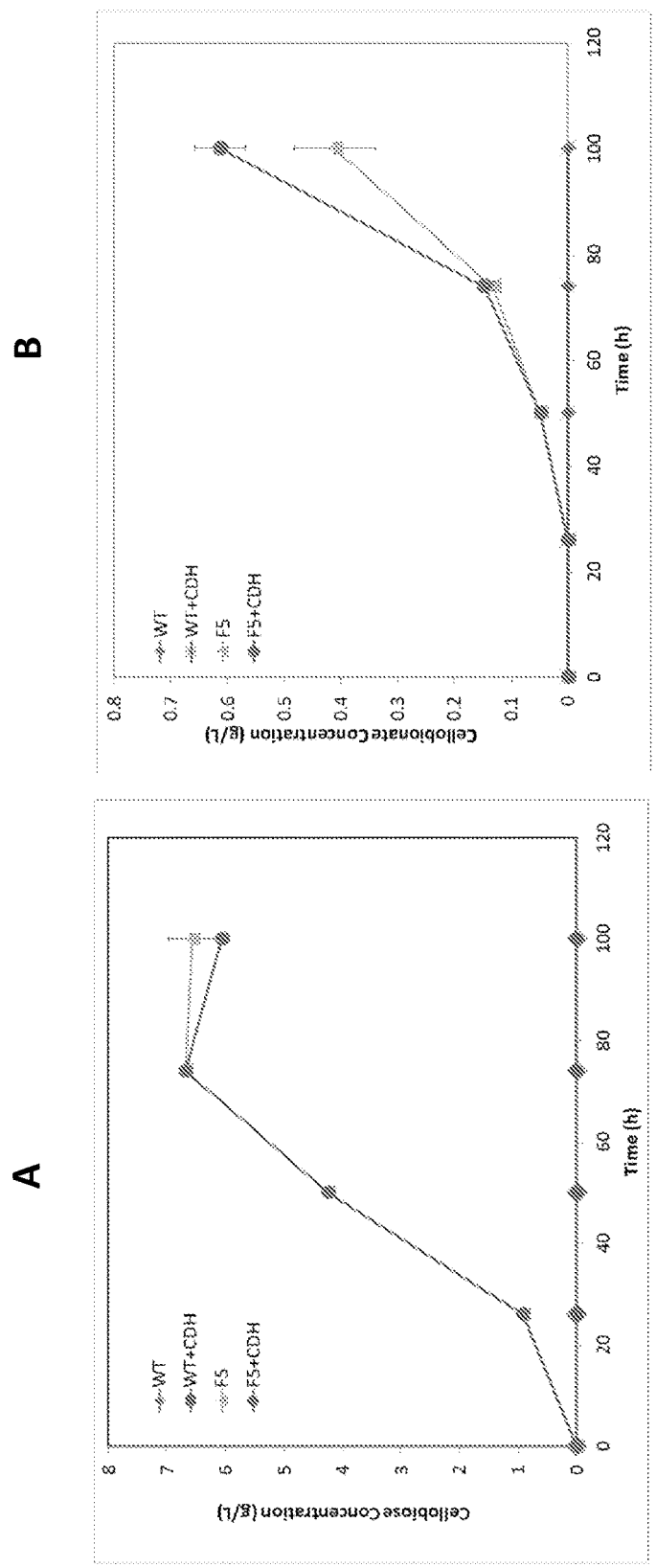
FIG. 4A illustrates cellobiose production by the F5 strain with or without exogenous cellobiose dehydrogenase addition.
FIG. 4B illustrates cellobionate production by the F5 strain with or without exogenous cellobiose dehydrogenase addition.
Figure 5:
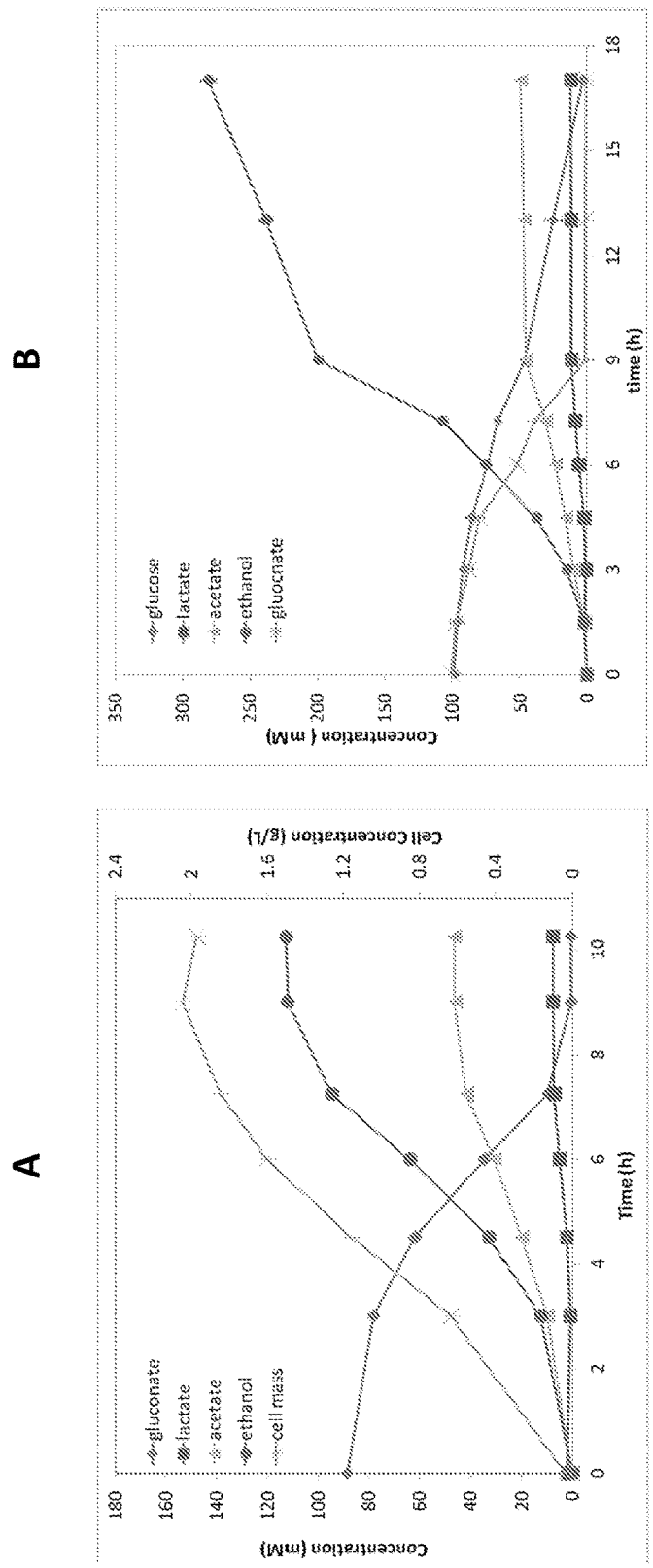
FIG. 5A illustrates conversion of gluconate to ethanol and acetate by the *Escherichia coli* strain KO 11.
FIG. 5B illustrates the conversion of a glucose and gluconate mixture to ethanol and acetate by the *Escherichia coli* strain KO 11.

Results
  Applicants previously constructed seven strains of *N. crassa* which have six out of the seven β-glucosidases (bgl) genes knocked out (sextuple bgl knock out strain), as well as constructing one septuple bgl knockout strain (Fan et al., 2012)(Wu et al., 2013). Applicants demonstrated that cellobionate can be produced from cellulose by one of best strains, which was named F5 (Fan et al., 2012). F5 contains mutations in each of the following β-glucosidase genes: NCU00130, NCU04952, NCU05577, NCU07487, NCU08755, and NCU03641. These results are reiterated in FIG. 4. For example, FIG. 4A demonstrates that the F5 strain, which is a sextuple bgl mutant strain, was able to accumulate cellobiose. FIG. 4B demonstrates that the F5 strain could also accumulate cellobionate, and that the addition of exogenous cellobiose dehydrogenase (CDH) enzyme could increase cellobionate concentrations present in this strain. FIG. 5A and FIG. 5B show that sugar acid alone and sugar plus sugar acids (glucose and gluconate) can be converted to fuels and chemicals (Fan et al., 2012).

Further, FIG. 6 provides a summary of cellulose conversion and mycelial mass production. Wild type cells (which retain full β-glucosidase activity) do not accumulate cellobiose or cellobionate. In contrast, the F5 strain, with or without CDH, accumulates both cellobiose and cellobionate and produces mycelia mass at lower yields than wild-type.

Cellobiose Conversion to Cellobionate with ABTS & Laccase

To further investigate sugar acid production by cellulolytic microorganisms, Applicants generated additional genetically modified N. crassa strains. The F5 strain (described above) was selected for further modification, and mutations in the cre-1 gene and in the ace-1 gene were introduced into the F5 strain. The cre gene is a known catabolite repressor, and deletion of this gene has been shown to increase cellulase expression. A cre-strain has decreased growth rate on preferred carbon sources; however, on Avicel it produces 30-50% more cellulase and consumes avicel faster (Sun et al., 2011), and cre expression correlates with cellulase expression. Mutation of the ace-1 gene (ace-) resulted in higher cellulase expression in T. reesei (Aro et al., 2003).

Figure 7:
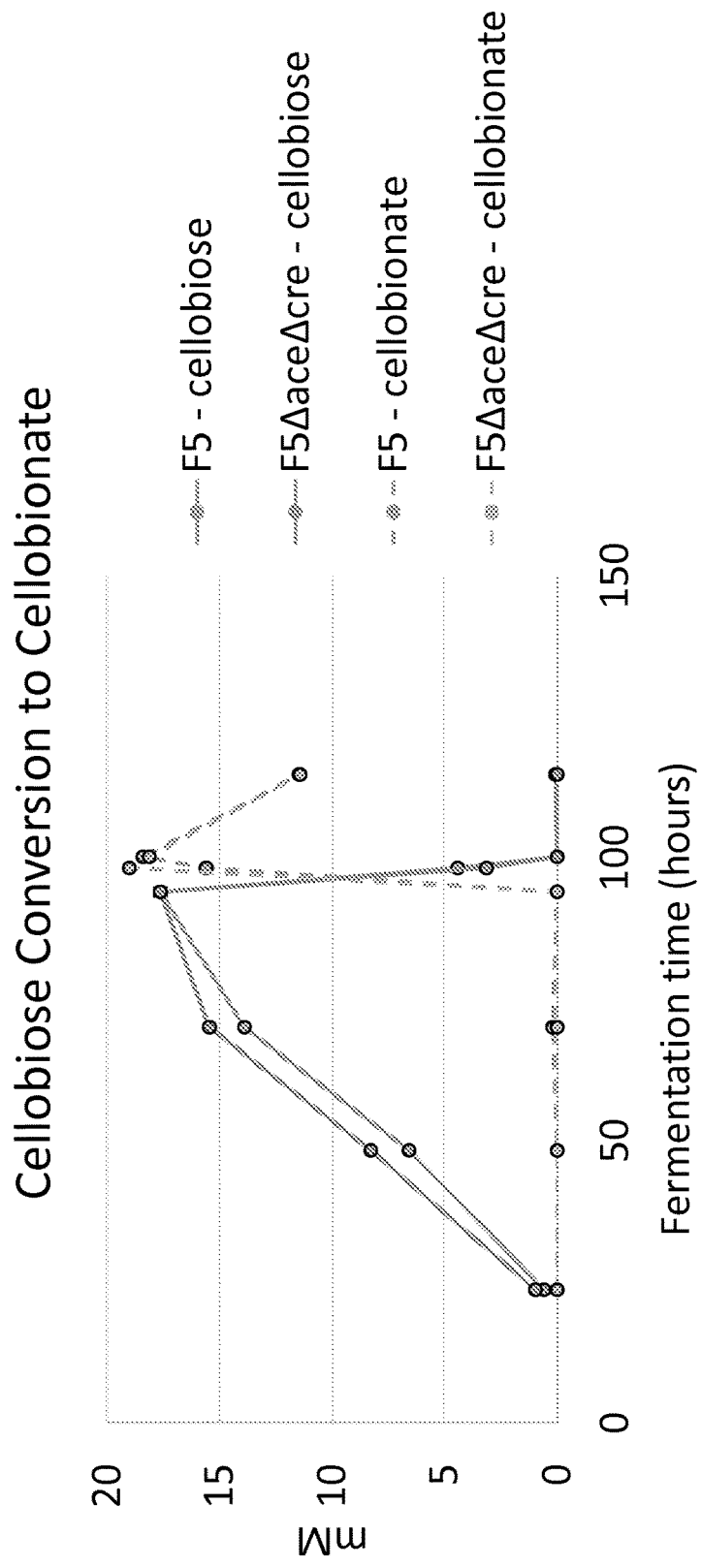
FIG. 7 illustrates the impact of laccase and ABTS on cellobiose and cellobionate production in various strains.

To assay cellobionate production in the F5 and the F5Δcre-1Δace strains, these strains were grown on Vogel's medium+20 g/L Avicel. 0.8 U/mL laccase and 0.1 mM ABTS were added to the culture at 96 hours. As can be seen in FIG. 7, cellobiose accumulated in both the F5 and F5Δcre-1Δace strains. At 96 hours when exogenous laccase and ABTS were added, cellobionate began to accumulate while cellobiose concentrations dropped rapidly. This result suggests that all the cellobiose was converted to cellobionate upon ABTS and laccase addition.

As described above, the addition of ABTS and laccase to the growth culture of both the F5 and F5Δcre-1Δace strains induced the accumulation of cellobionate in the media, as the cellobiose in the media was converted to cellobionate. Without wishing to be bound by theory, it is thought that laccase is involved in regenerating the activity of cellobiose dehydrogenase (CDH) enzymes present in these strains. When a flavo-enzyme, such as CDH, oxidizes a substrate such as cellobiose, it abstracts two electrons from the substrate, converting the substrate into its corresponding lactone which spontaneously hydrolyzes to an aldonic acid. In order for CDH to regain functionality, it must be oxidized. Oxygen is a thermodynamically favorable electron acceptor for CDH; however, it is extremely rate limiting. Laccase is an oxido-reductase, which, in contrast to CDH, is efficiently oxidized by oxygen, with the only byproduct being water. The FAD-containing enzyme cellobiose dehydrogenase (CDH; EC 1.1.99.18) oxidizes lactose at the C-1 position of the reducing sugar moiety to lactobionolactone, which spontaneously hydrolyzes to lactobionic acid. The cation radical of 2,20-azino-bis(3-ethylbenzothiazoline-6-sulfonic acid) (ABTS) is used as one possible electron acceptor (redox mediator) in this reaction, and is continuously reoxidized by laccase (LAC; EC 1.10.3.2), a multi-copper oxidase (van Hecke et al., 2009).

Figure 8:
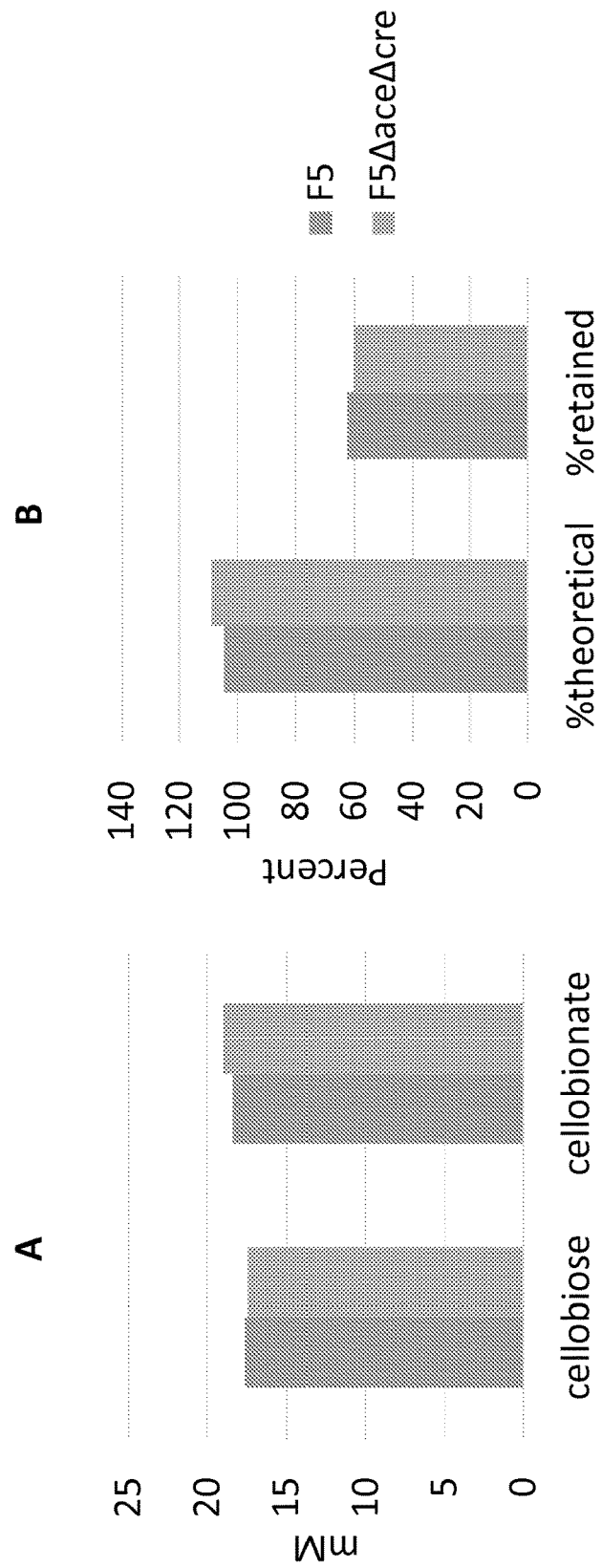
FIG. 8A illustrates cellobiose and cellobionate levels in various strains.
FIG. 8B illustrates theoretical and retained yields of cellobionate.
Figure 9:
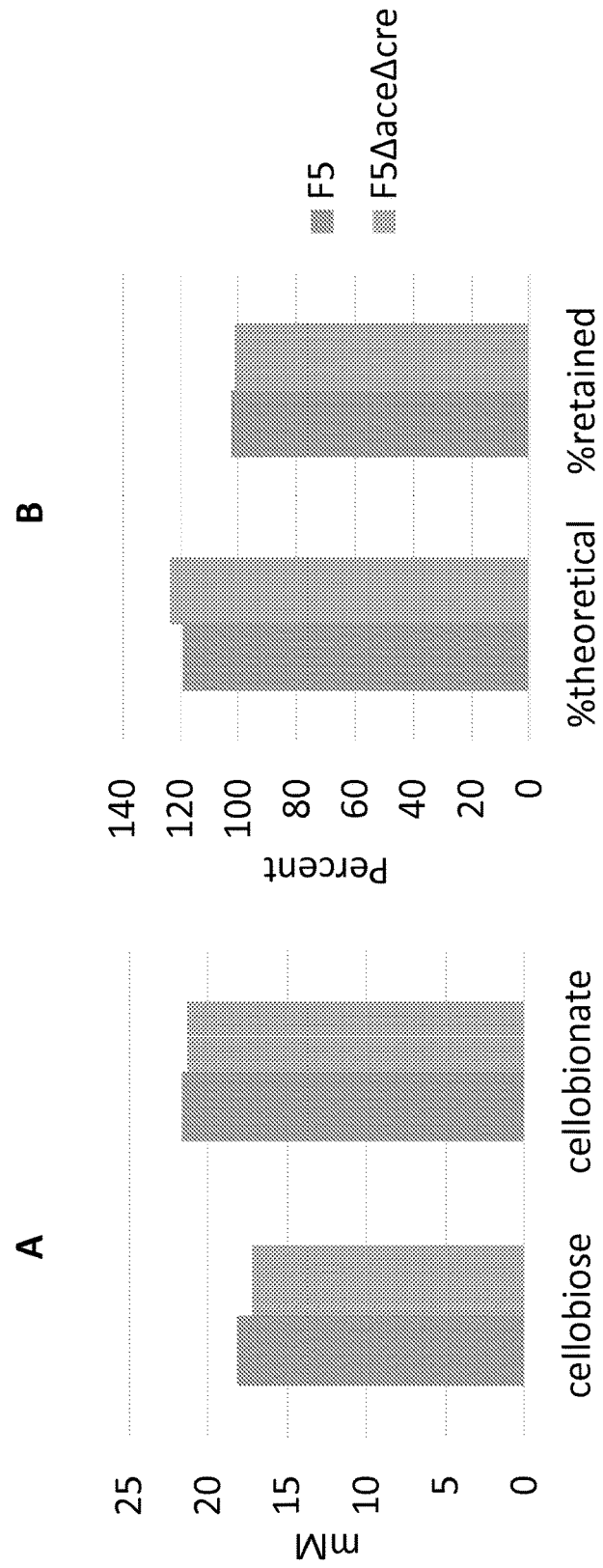
FIG. 9A illustrates cellobiose and cellobionate levels in various strains with cells and cellulose filtered prior to the conversion reaction.
FIG. 9B illustrates theoretical and retained yields of cellobionate.
Figure 10:
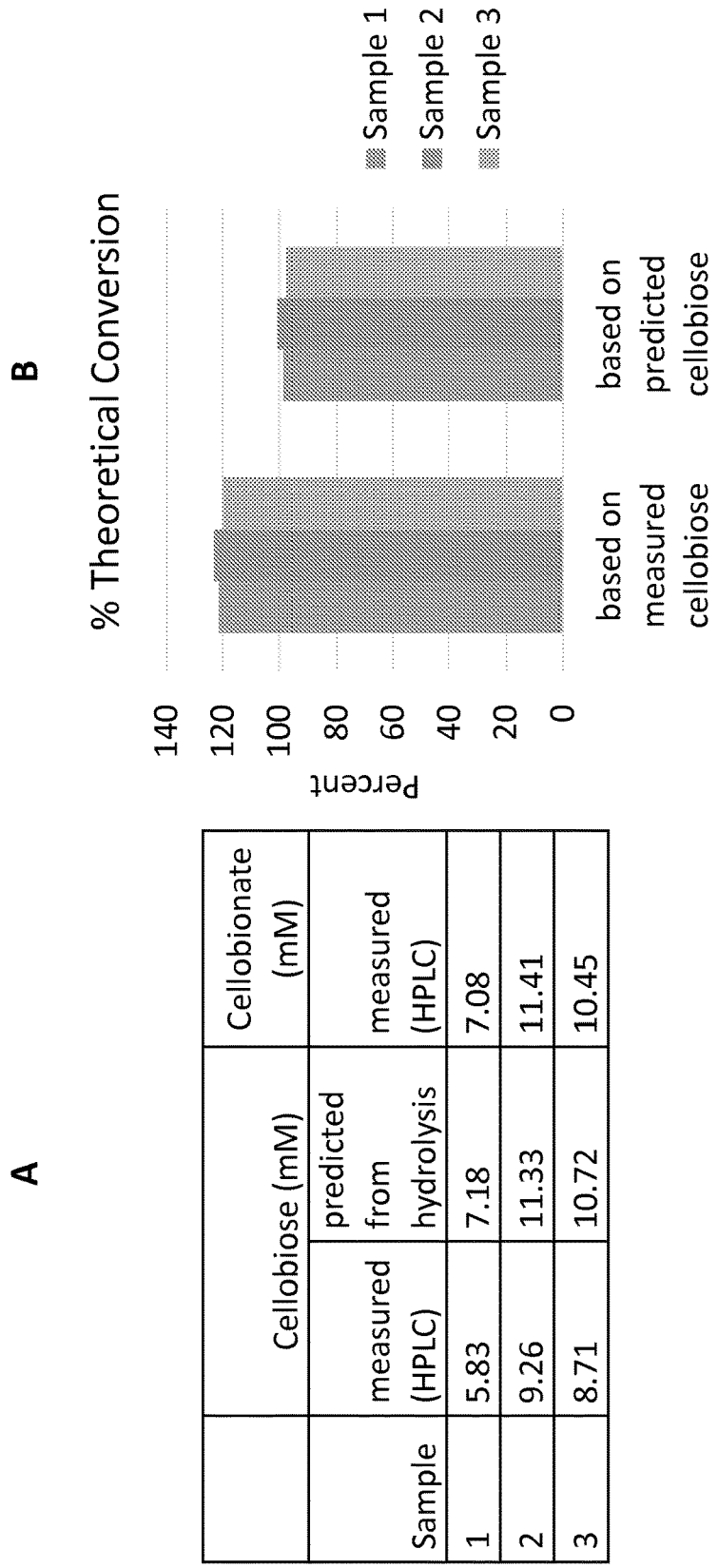
FIG. 10A illustrates a table depicting theoretical cellobiose and cellobionate concentrations.
FIG. 10B illustrates theoretical conversions of cellobionate based on either measured or predicted cellobiose levels.

Applicants further investigated cellobionate accumulation in the F5 and F5Δcre-1Δace strains. Additional experiments with these strains and employing laccase/ABTS in shake flask fermentation are presented in FIG. 8A and FIG. 8B. Cells were grown in Vogel's medium with 20 g/L Avicel, and 96 hours into the fermentation, laccase and ABTS were added. A similar experiment is presented in FIG. 9A and FIG. 9B, except that prior to the addition of laccase and ABTS, cells and cellulose were filtered prior to initiating conversion reaction. Further calculations are provided in FIG. 10A and FIG. 10B. The conversion calculations are based on a theoretical conversion of 1 mole of cellobiose to 1 mole of cellobionate. For example, if 15 mM of cellobionate is obtained from 20 mM of cellobiose, the conversion % is 75%. If 22 mM of cellobionate is obtained from 20 mM of cellobiose, the conversion % is 110%. As can be seen, more than 100% percent of theoretical maximal cellobiose conversion to cellobionate was observed. This may be because some other cello-oligosaccharides in the broth are converted to cellobionate via the CDH-laccase-ABTS redox-mediated system. The residual % is the amount of cellobionate detected at a given time compared to the maximum amount of cellobionate detected at a previous time point. For example, if the maximum amount of cellobionate detected is 15 mM, and the amount of cellobionate detected 24 hours later is 10 mM, the residual % of cellobionate is 66%. Without wishing to be bound by theory, it is thought that either cellulose is continuously converted as cellobiose is converted (relieved inhibition), or that cello-oligosaccharides are also converted to cellobionate.

NdvB Knockout Strains

Figure 11:
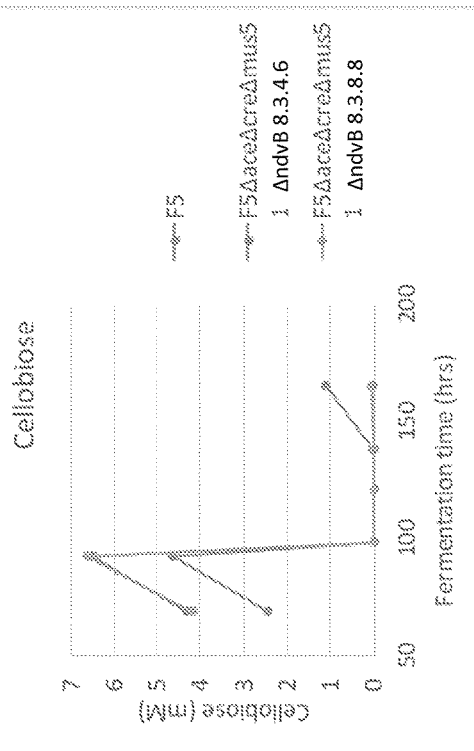
FIG. 11A illustrates cellobionate levels in various strains.
FIG. 11B illustrates cellobiose levels in various strains.
FIG. 11C illustrates cellobiose dehydrogenase (CDH) activity in various strains.
Figure 11:
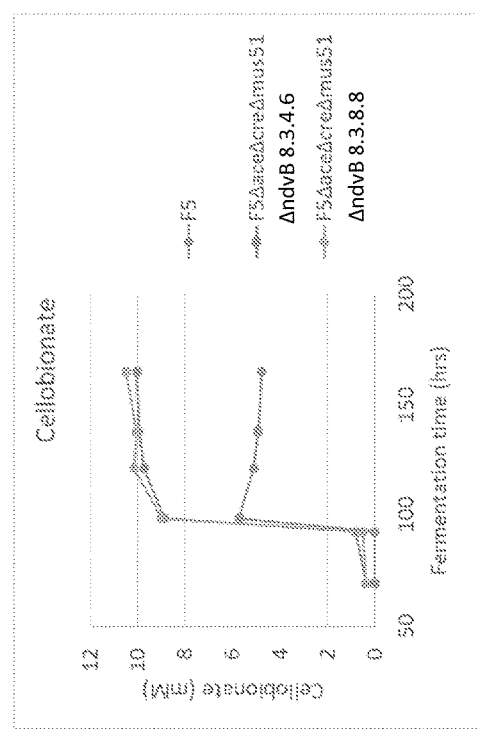
Figure 11:
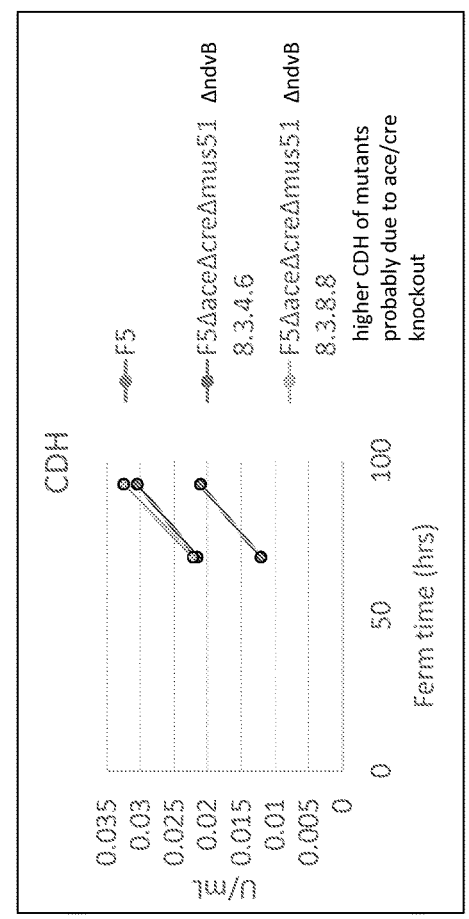

Applicants further modified the F5Δcre-1Δace strain to contain mutations in the ndvB gene, which encodes a cellobionate phosphorylase. Two ndvB knockout strains (8.3.4.6 & 8.3.8.8) were chosen for evaluation in the CDH-ABTS-laccase redox system as compared to the parent strain (F5Δcre-1Δace). The two ndvB knockout strains were further modified to contain a mus51 mutation. Without wishing to be bound by theory, it is thought that a mus51 mutation increases the ease of genetic modification of this strain. Fermentation conditions for these strains were as described above. At 92.5 hours into the fermentation, laccase (0.8 U/mL and ABTS (0.1 mM) were added to the fermentation broth to initiate conversion of cellobiose to cellobionate. The concentrations of cellobiose to cellobionate were monitored by HPLC. As can be seen in FIG. 11A and FIG. 11B, all the cellobiose was converted to cellobionate upon the addition of ABTS and laccase to the culture media. F5Δcre-1ΔaceΔmus51ΔndvB strains produced higher concentration of cellobionate as compared to the F5 strain. The F5Δcre-1ΔaceΔmus51ΔndvB strains also exhibited higher CDH activity (FIG. 11C). Without wishing to be bound by theory, it is thought that the higher CDH activity of F5Δcre-1ΔaceΔmus51 ΔndvB mutant strains is due to the loss of CRE-1 and ACE-1 activity in these strains.

Analysis of Cellobionate Consumption in F5Δcre-1ΔaceΔndvB Strains

Figure 12:
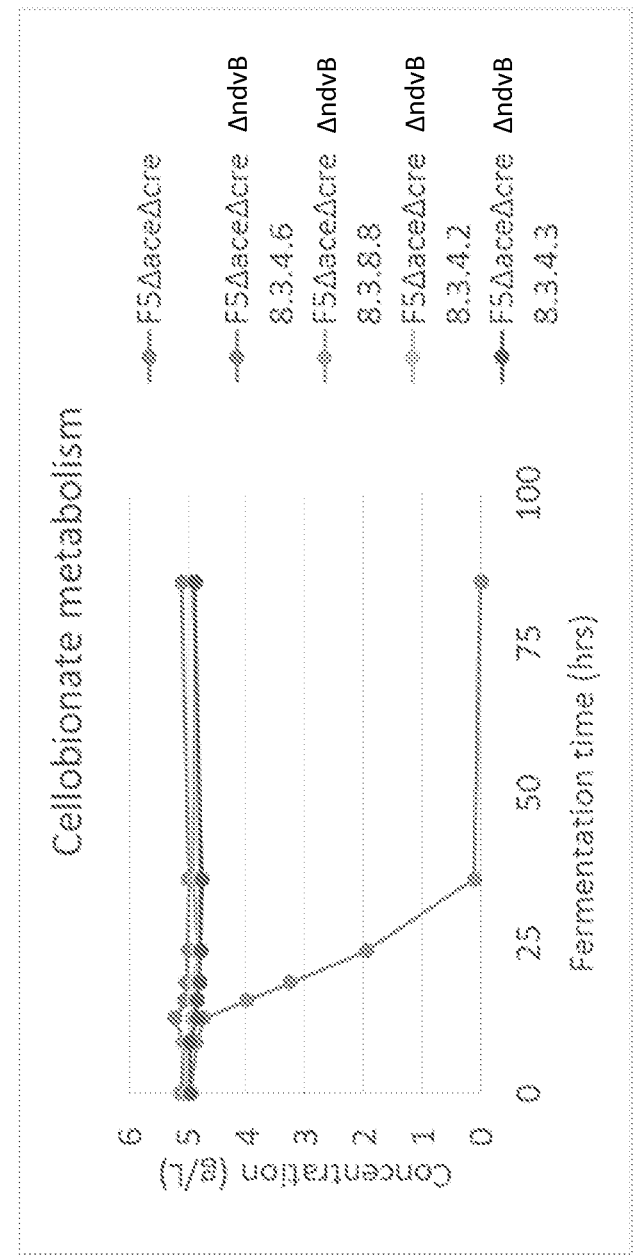
FIG. 12 illustrates cellobionate utilization by the F5Δcre-1Δace strain and the F5Δcre-1ΔaceΔndvB strains.

Without wishing to be bound by theory, it is thought that loss of cellobionate phosphorylase results in a block in cellobionate consumption. To explore this metabolism further, four separate F5Δcre-1ΔaceΔndvB knockout strains were constructed and compared to the F5ΔaceΔcre-1 strain for cellobionate consumption. All strains were evaluated in 1× Vogel's salts with 0.5 g/L glucose (to initiate cell growth) and 20 g/L cellobionate. The concentration of glucose and cellobionate in the broth supernatant was determined by HPLC using an Aminex 87C column with 4 mM CaCl2 mobile phase at 0.6 mL/minute. As can be seen in FIG. 12, all strains analyzed consumed glucose in just over 8 hours. The F5ΔaceΔcre-1 strain consumed the 5 g/L of cellobionate in just over 27 hours and only after glucose was depleted. In contrast, the F5Δcre-1ΔaceΔndvB knockout strains did not consume any cellobionate.

Laccase Overexpression in F5Δcre-1ΔaceΔndvB Strains

Figure 13:
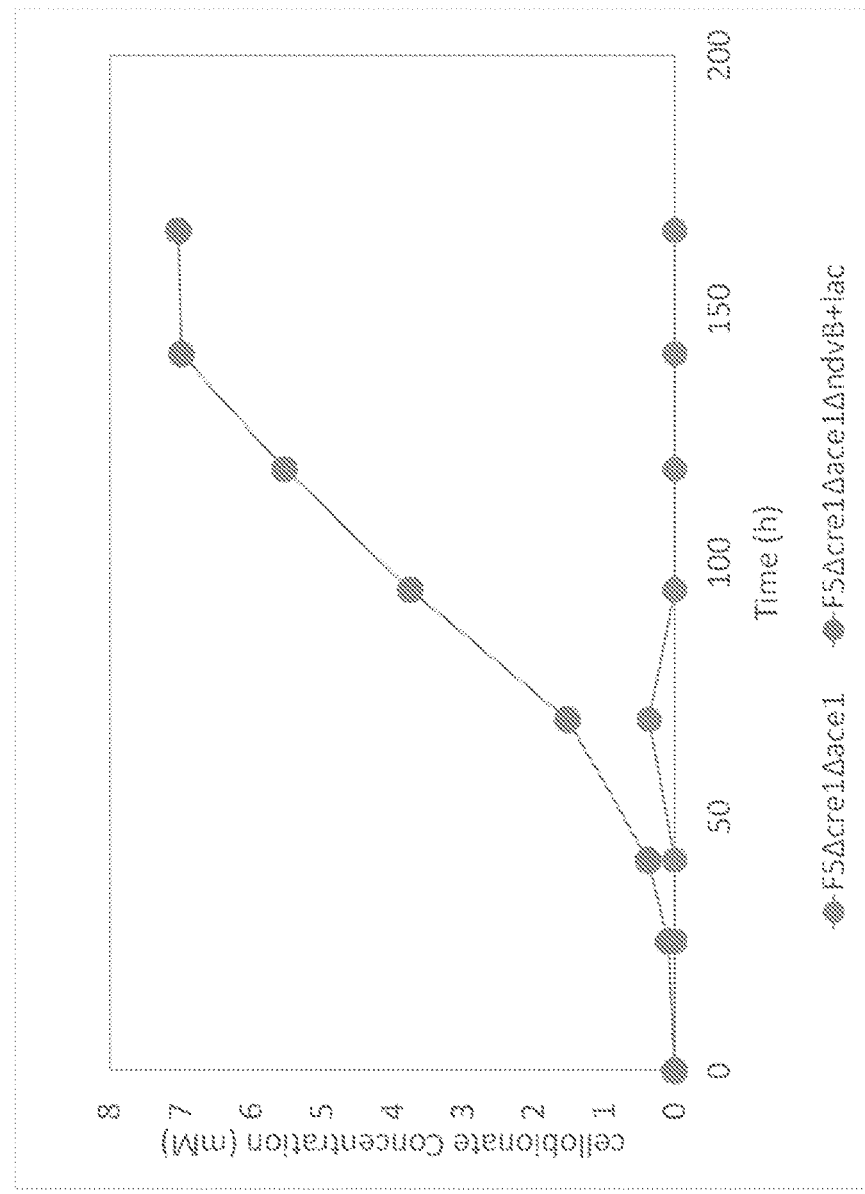
FIG. 13 illustrates cellobionate production by the F5Δcre-1Δace strain and the F5Δcre-1ΔaceΔndvB+lac strain.

Applicants analyzed cellobionate accumulation in F5Δcre-1ΔaceΔndvB strains that were genetically engineered to overexpress laccase. For testing the effect of laccase enzyme overexpression, ten day old conidia of the strain F5Δcre-1ΔaceΔndvB+lac and the control strain F5Δcre-1Δace were collected and inoculated into flasks that contain 20 g/L Avicel and 0.6 g/L glucose. The fermentations were carried out at 27° C. at 200 rpm with the light on. 0.1 mM of ABTS was added at the beginning of the culture. Samples were taken at various time intervals. Concentrations of cellobiose and cellobionate were measured by HPLC. As shown in FIG. 13, the F5Δcre-1Δace strain produced a small amount of cellobionate. However, the produced cellobionate was subsequently consumed by the fungus. However, the F5Δcre-1ΔaceΔndvB+lac strain produced about 7 mM of cellobionate, and no consumption of cellobionate by the strain was observed.

Figure 14:
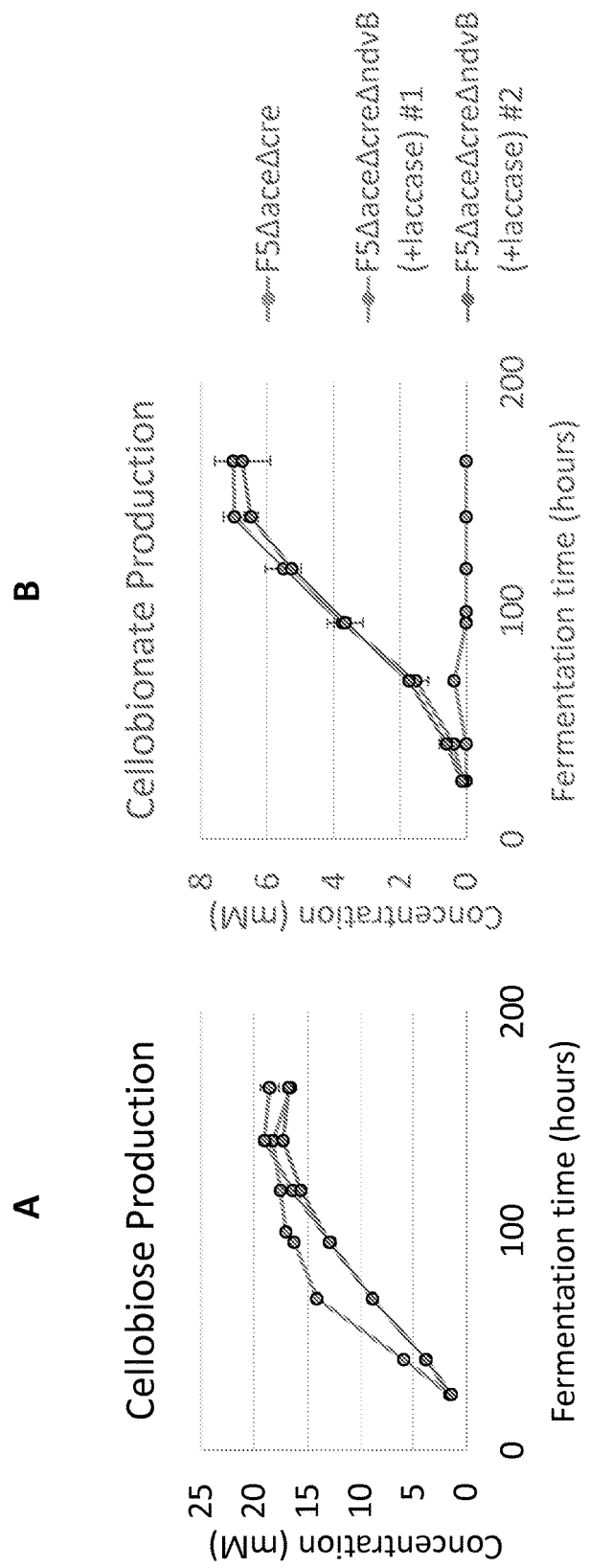
FIG. 14A illustrates cellobiose production in various strains.
FIG. 14B illustrates cellobionate production in various strains. All strains were grown on 20 g/L Avicel.

An additional laccase overexpression strain was constructed to confirm the results obtained in FIG. 13. As can be seen in FIG. 14A and FIG. 14B, mutations in cellobionate phosphorylase (ndvB) and overexpression of laccase in the F5Δcre-1Δace mutant background resulted in markedly increased cellobionate production as compared to the F5Δcre-1Δace strain.

Summary

In summary, the data presented herein demonstrates a Neurospora crassa that was engineered for increased production of cellobionate from cellulose. Multiple bgl gene deletions redirected carbon flow toward cellobiose/cellobionate production. Cre/ace gene deletions promote cellulase expression. NdvB gene deletion eliminates cellobionate consumption. Finally, laccase overexpression improves cellobionate production in the presence of CDH and a redox mediator.

Example 2: Production of Cellobionate from Cellulose Using an Engineered Neurospora crassa Strain with Laccase and Redox Mediator Addition This Example demonstrates a production process for producing cellobionic acid from cellulose using an engineered fungal strain with the exogenous addition of laccase and a redox mediator. From Example 1, an engineered strain of Neurospora crassa (F5Δace-1Δcre-1ΔndvB) was shown to produce cellobionate directly from cellulose without the addition of exogenous cellulases. N. crassa produces cellulases (which hydrolyze cellulose to cellobiose) and cellobiose dehydrogenase (CDH)(which oxidizes cellobiose to cellobionate). However, the conversion of cellobiose to cellobionate is limited by the slow re-oxidation of CDH by molecular oxygen. By adding low concentrations of laccase and a redox mediator to the fermentation, CDH can be efficiently oxidized by the redox mediator, with in-situ re-oxidation of the redox mediator by laccase. In this Example, the conversion of cellulose to cellobionate was optimized by evaluating pH, buffer, and laccase and redox mediator addition time on the yield of cellobionate. Mass and material balances were performed, and the use of the native N. crassa laccase in such a conversion system was evaluated against the exogenous Pleurotus ostreatus laccase.

Introduction

The development of microbial fermentation platforms for the production of organic acids has gained interest in the last decade (Jang et al., 2012; Sauer et al., 2008) due to the reliability and cost-effectiveness of such processes (Demain et al., 2007). In recent years, carboxylic acids, such as lactobionic acid (LBA), have emerged as specialty acids due to their unique physiochemical properties. LBA is a high value-added organic acid, with numerous applications that span the pharmaceutical, food, and cosmetics industries (Alonso et al., 2013). In order to compete with petroleum-based processes for the production of carboxylic acids, the development of microbial processes utilizing low-cost substrates is essential (Alonso et al., 2013). LBA is currently produced through chemical synthesis in an energy-intensive process requiring costly metal catalysts. Alternatively, LBA can be produced biologically by various bacterial and fungal strains using refined lactose as the substrate (Miyamoto et al., 2000; Meiberg J et al., 1990; Murakami H et al., 2006; Murakami H et al., 2003; Pedruzzi I et al., 2011; Malvessi E et al., 2013; Kiryu T et al., 2012; Alonso S et al., 2011; Alonso S et al., 2012; Alonso S et al., 2013). The inexpensive substrate cheese whey was also investigated as a substrate for LBA production by Pseudomonas taetrolens in an environmentally-friendly fermentation process (Alonso S et al., 2013; Alonso S et al., 2011; Alonso S et al., 2012). The enzyme which catalyzes the biotransformation is lactose dehydrogenase (Miyamoto et al., 2000; Meiberg J et al., 1990; Murakami H et al., 2006; Murakami H et al., 2003; Pedruzzi I et al., 2011; Malvessi E et al., 2013; Kiryu T et al., 2012; Alonso S et al., 2011; Alonso S et al., 2012; Alonso S et al., 2013).

LBA could also be produced from lactose enzymatically by the action of CDH. CDH is a hemoflavoenzyme produced by several cellulolytic fungi. It contains a C-terminal flavin adenine dinucleotide (FAD) domain responsible for oxidizing lactose or cellobiose, resulting in the formation of lactobionate or cellobionate, respectively. The two electrons are subsequently transferred from the FAD domain to the N-terminal heme domain (Henriksson G et al., 2000). In order for CDH to regain functionality, the reduced heme domain must be oxidized with the help of an electron acceptor. Oxygen is the electron acceptor in this system if no other electron acceptors are present. Although the overall reaction is thermodynamically favorable, the rate of re-oxidation of CDH by molecular oxygen is very slow and is the rate-limiting step in converting lactose to LBA (Roy B P et al., 1996; Bao W et al., 1993).

Other than oxygen, a wide variety of substrates such as metal ions, quinones, and organic dyes can be alternative electron acceptors for the heme domain of the CDH (Baminger U et al., 2001). Dichlorophenolindophenol (DCPIP) and 2,2'-azino-bis[3-ethylbenzothiazoline-6-sulphonic acid] (ABTS) are two redox mediators that can accept electrons from CDH very efficiently (Baminger U et al., 2001). However, the addition of redox mediators to facilitate electron transfer in CDH to improve the conversion rate of lactose to LBA is cost prohibitive unless the redox mediator can be regenerated in-situ.

Figure 16:
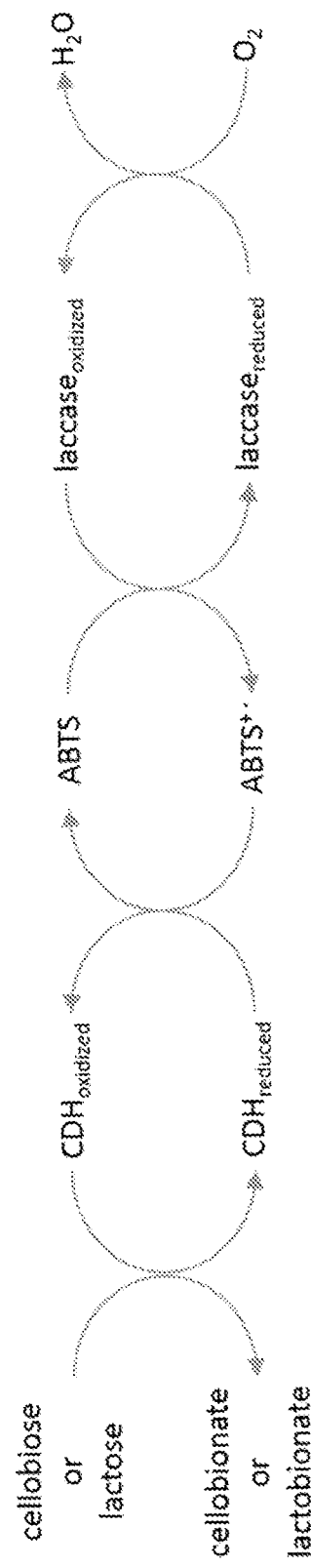
FIG. 16 illustrates the enzymatic oxidation of substrate (cellobiose/lactose) by CDH. The reduced CDH is oxidized by a redox mediator (ABTS), which is in turn oxidized by laccase. The reduced laccase is oxidized by oxygen, with water as the only byproduct.

Baminger et al. reported a novel CDH-ABTS-laccase bi-enzyme system for fast oxidation of lactose to LBA (Baminger U et al., 2001). Laccases are important multi-copper oxidases which are also widely distributed in wood degrading fungi (Madhavi V et al., 2009). They are especially prevalent in white rot and brown rot fungi, with speculative involvement in lignin degradation (Arora D S et al., 2010). In contrast to CDH, laccases oxidize a large number of reduced substances and use oxygen as the final electron acceptor very efficiently. One strategy to increase the rate of lactose oxidation by CDH with oxygen as the final electron acceptor is to employ catalytic amounts of DCPIP or ABTS with in-situ regeneration of the redox mediator by laccase. As shown in FIG. 16, CDH is reduced. When lactose is oxidized to lactobionic acid, in turn, the reduced CDH is re-oxidized with the help of a redox mediator, which is then regenerated through oxidation by laccase. Lastly, laccase is regenerated when the electrons are passed to oxygen, the final electron acceptor. Such a bi-enzyme cascade system was found to be able to drastically boost the rate of conversion of lactose to LBA using ABTS as a redox mediator (Baminger U et al., 2001; Van Hecke W et al., 2009).

Cellulosic biomass, which is available at low cost and in widespread abundance (Lynd L R et al., 1991), is a potential alternative substrate for the bio-production of carboxylic acids. In Example 1, Applicants investigated a process for the production of cellobionic acid (CBA), which is a sister carboxylic acid (stereoisomer) to LBA, directly from cellulose using an engineered *Neurospora crassa* strain with exogenous laccase and redox mediator addition.

*N. crassa* was previously engineered to produce cellobiose from cellulose by deleting six out of seven β-glucosidase (BGL) genes, resulting in a strain designated F5 (Fan Z et al., 2012; Wu W et al., 2013). The strain also produces CDH, which can oxidize cellobiose to CBA. The strain was further engineered by Applicants to prevent CBA consumption by knocking out the cellobionate phosphorylase (ndvB) gene, and cellulase expression was improved by deleting carbon catabolite repression genes, cre-1 and ace-1, in a strain designated F5Δace-1Δcre-1ΔndvB (Hildebrand A et al., 2014)(See Example 1). From 20 g/L Avicel, the F5Δace-1Δcre-1ΔndvB strain produces 20 mM (7 g/L) cellobiose and 10 mM CBA (3.5 g/L). In such a system, oxygen was the final electron acceptor. The re-oxidization of CDH by oxygen is the rate limiting step, which led to incomplete conversion of most of the cellobiose to CBA.

In this Example, Applicants explored the possibility of using the engineered *N. crassa* F5Δace-1Δcre-1ΔndvB strain to break down cellulose to cellobiose and produce CDH. Exogenous addition of laccase and ABTS will complement CDH to form the bi-enzyme cascade system to convert cellobiose to CBA. Fermentation conditions including, pH, buffer, and laccase and ABTS concentration and addition times were optimized to maximize the yield of CBA from cellulose. In addition, a material balance on the overall fermentation is included. Lastly, the possibility of using the native *N. crassa* laccase in the CDH-ABTS-laccase system was investigated.

Materials and Methods

Strains and Reagents

Wild-type *Neurospora crassa* (2489) was obtained from the Fungal Genetics Stock Center (FGSC)(McCluskey K et al., 2010). The F5 strain used in this Example is strain 2489 with six out of seven of its bgl genes knocked out (Fan Z et al., 2012; Wu W et al., 2013). The F5 strain was engineered for increased cellulase expression and cellulose hydrolysis by knocking out the ace-1, cre-1, and ndvB genes as described in Hildebrand A et al., 2014. The strains used in this Example and their sources are listed in Table 1.

TABLE 1

Exemplary Strains Used in this Example

| Strain | Genotype | Source |
|---|---|---|
| FGSC 2489 | Wild type | Fungal genetic source center |
| F5Δace-1Δcre-1ΔndvB | bgl-1::hph bgl-2::hph bgl-3::hph bgl-4::hph bgl-6::hph bgl-7::hph mus-51::ace-1::six cre-1::six mat A | (Wu W et al., 2013) |

For the construction of an *N. crassa* strain overexpressing the native *N. crassa* laccase, the native laccase gene was overexpressed using a cyclosporine A-resistance based gene placement system as previously described. The gpdA promoter (from *Aspergillus niger*), laccase gene (NCU04528.7), and trpC terminator were synthesized by Life Technologies and ligated to a vector, with flanks with csr-1 homology. The plasmid was expressed in *E. coli* and linear DNA of the insertion cassette obtained by restriction digest of the plasmid. 1200 μg of the linear DNA was combined with $2.5 \times 10^9$ conidia/mL and electroporated (0.1 cm cuvette-7.5 kV/cm; capacitance: 25 uFD; resistance: 600 ohms). Following electroporation, cells were regenerated in 750 mL of 1M ice cold sorbitol, which was then added to 2 mL of recovery medium (1× Vogel's medium, 2% yeast extract). After 6 hours of shaking at 30° C. and 200 rpm, 350 μL of the recovered cells were plated on agar plates (1× Vogel's, 2% yeast extract, 1M sorbitol, 20 g $l^{-1}$ sorbose, 0.5 μg $l^{-1}$ fructose, 0.5 g $l^{-1}$ glucose, 5 μg $ml^{-1}$ CsA, and 2% agar). After 5 days of growth at 30° C., colonies were placed on slants (Slants (5 μg $mL^{-1}$ CsA, 1× Vogel's, 2% agar slopes) and grown for an additional 4 days. Transformants were verified by PCR.

Laccase from *P. ostreatus* was obtained from Sigma Aldrich and used in certain experiments described involving the exogenous addition of laccase. ABTS was obtained from Sigma Aldrich. For in vitro experiments, the CDH used was a recombinant *N. crassa* CDH produced by an engineered *Pichia pastoris* strain. It was produced according to the method described by Zhang et al., 2011.

Conversion of Cellobiose to CBA Using the CDH-ABTS-Laccase System

To test the suitability of the CDH-laccase-ABTS redox system on converting cellobiose to cellobionate, a concentration of approximately 30 mM cellobiose was added to 50 mL falcon tubes containing laccase, ABTS, CDH, and buffer at the indicated concentrations and pH. When investigating the effect of pH, sodium citrate buffer at a concentration of 50 mM was used for acidic conditions, sodium phosphate buffer was used at a concentration of 50 mM for basic conditions, and 1× Vogel's salts medium with no pH adjustment was used for the pH 6 condition.

Fermentation Experiments

*N. crassa* strains were grown on agar with 1× Vogel's salts and 1.5% sucrose in an incubator at 30° C. with light. After 3 days, flasks were removed from the incubator and grown for 7 days at room temperature. After a total of 10 days of growth, the conidia were harvested in DI water and filtered through eight layers of cheese cloth. Fermentation experiments were conducted in 250 mL unbaffled flasks with a 50 mL working volume, 1× Vogel's salts medium, 0.5 g/L of glucose to initiate growth, and 20 g/L Avicel. Conidia were inoculated at a volume to yield a final $OD_{420}$ of 0.15. Flasks were incubated at 28° C. in a rotary shaker at 200 rpm with light. Exogenous laccase and ABTS were added to the flasks as indicated in the text. Samples were taken at various time intervals to measure cellobiose or cellobionate concentration. To investigate the effect of starting pH on cellobionate yield, sodium citrate, sodium phosphate, potassium phosphate, and sodium-potassium phosphate buffers of different concentrations were added to achieve the pH indicated. To study the effect of laccase and ABTS addition time on cellobionate production, laccase and ABTS were added to the fermentation broth at final concentrations of 0.05 U/mL and 0.01 mM, respectively.

Fermentation Experiments with *N. crassa* Laccase Overexpression Strains

*N. crassa* was grown on agar with 1× Vogels salts and 1.5% sucrose in an incubator at 30° C. with light. After 3 days, flasks were removed from the incubator and grown for 7 days at room temperature. After a total of 10 days of growth, the conidia was harvested in DI water and filtered through several layers of cheese cloth. Fermentation experiments were conducted in 250 mL unbaffled flasks with a 50 mL working volume. The growth medium contained either 1× Vogel's salts medium and 20 g/L glucose to initially test laccase overexpression, or 1× Vogel's salts medium, 0.5 g/L of glucose to initiate growth, and 20 g/L Avicel. Conidia were inoculated at a volume to yield a final $OD_{420}$ of 0.15. Flasks were incubated at 28° C. in a rotary shaker at 200 rpm with light. ABTS was added at initial concentration of 0.1 mM.

Laccase Production by *Neurospora crassa*

The wild type strain was grown in Vogel's salts medium on 1.5% sucrose. Cycloheximide, an inducer for laccase production, was added at 48 hours at a final concentration of 3 µM according to literature (Huber M et al., 1987; Linden R M et al., 1991; Froehner S C et al., 1974). Laccase expression was monitored according to the assay described below in the "enzyme concentration" section. After an additional 142 hours of fermentation, the broth was filtered to remove residual Avicel and cells in order to obtain the native laccase for evaluation in the CDH-ABTS-laccase redox system in cell-free experiments.

Sample Analysis

Concentrations of cellobiose and cellobionate in the cell-free experiments and in the fermentation broth were analyzed using a Shimadzu HPLC equipped with a CARBOSep COREGEL-87C (Transgenomic, San Jose, Calif., USA) column. 4 mM calcium chloride ($CaCl_2$) at a flow rate of 0.6 mL/min was used as the mobile phase.

Enzyme Concentration

Laccase activity was measured by monitoring the increase in absorbance of ABTS as described previously with minor modifications (Van Hecke W et al., 2009; Baminger U et al., 1999). The reaction mixture contained 5 mM ABTS in 100 mM sodium acetate buffer, pH 4.5. One unit of laccase activity is defined as the amount of enzyme oxidizing 1 µmol of ABTS per minute under the above reaction conditions.

The concentration of CDH was determined by monitoring the decrease in absorbance of DCPIP at 520 nm in a spectrophotometer according to previously established methods with slight modification (Van Hecke W et al., 2009; Baminger U et al., 1999). The reaction contained 0.1 mM DCPIP, 3 mM cellobiose, and 4 mM sodium fluoride in 100 mM sodium acetate buffer at pH 4.5. One unit of enzyme activity is defined as the amount of enzyme reducing 1 µmol of DCIP per minute under the above reaction conditions.

Mycelial Biomass Measurements

The dry weight of the mycelia contained in the fermentation samples was measured by extracting ergosterol from the mycelia and measuring the amount by HPLC (Gessner M O et al., 1991). The fermentation residues were collected by filtration through a 0.8 µm membrane. All the residue including the mycelia were harvested, frozen in liquid nitrogen for 1 hour, and ethanol (6 mL) was added to the frozen sample and incubated at 37° C. for 2 hours with shaking. An aliquot of KOH solution (60% w/v, 0.8 mL) was added to the mixture, which was then heated to 97° C. for 20 min. This sample was cooled and neutralized with HCl (36.5%, ~0.7 mL). The solution was extracted with hexane (3×5 mL), the hexane fractions were combined, and air was used to evaporate the solvent. The residue was dissolved in ethanol (1 mL), filtered through a 0.22 µm membrane filter and analyzed by HPLC with PDA detector on a reverse phase column (ZORBAX Eclipse Plus C18, 4.6×250 mm, 5 µm particle size, Agilent) and eluted at 1.0 mL/min with methanol-water (97:3 v/v). The amount of biomass was quantified using a standard curve prepared with known *N. crassa* dry biomass. The amount of residual Avicel was calculated by subtracting the mycelial biomass from the dry weight of the fermentation residues.

Results

Figure 17:
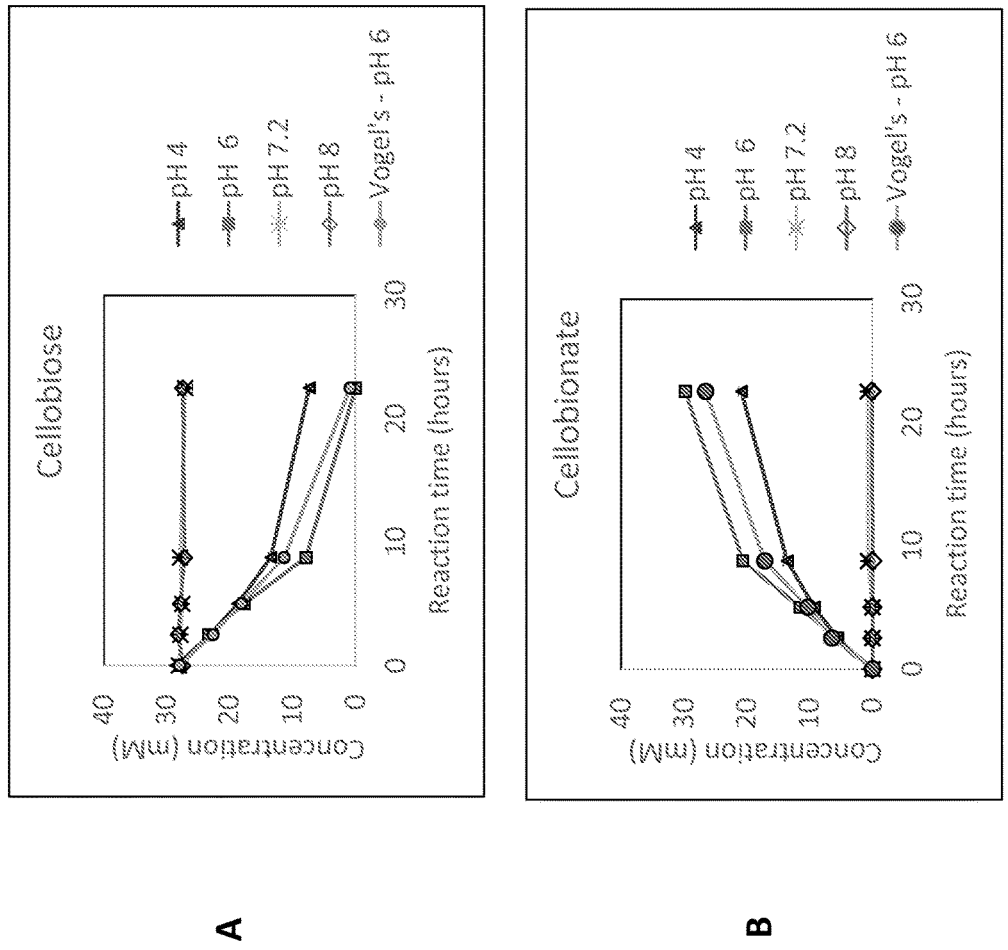
FIG. 17A and FIG. 17B illustrate the effect of pH on the conversion of cellobiose to CBA via CDH-ABTS-laccase mediated conversion. Acidic conditions (pH 4 and pH 6) used 50 mM sodium citrate buffer; pH 7.2 and pH 8 used 50 mM sodium phosphate buffer. The Vogels pH 6 condition used 1× Vogel's salts medium. The results shown are the means of biological duplicates with the error bars representing the standard deviation.

Role of pH in the Conversion of Cellobiose to CBA Using the CDH-ABTS-Laccase System Acidic, neutral, and basic conditions were tested to determine the effect of pH on the conversion of cellobiose to CBA. The time course of the conversion of cellobiose to CBA is shown in FIG. 17A and FIG. 17B. For conditions at pH 6, conversion was completed within 24 hours with an average of 27.9 mM cellobiose converted to 28.6 mM CBA, resulting in an approximate 1:1 molar conversion, as expected. The data obtained support the efficacy of CDH-ABTS-laccase system for converting cellobiose to cellobionate. However, the presence of acidic conditions was important for the efficient conversion of cellobiose to CBA for the specific CDH and laccase used in this experiment.

The Effect of Starting pH on CBA Production

Figure 18:
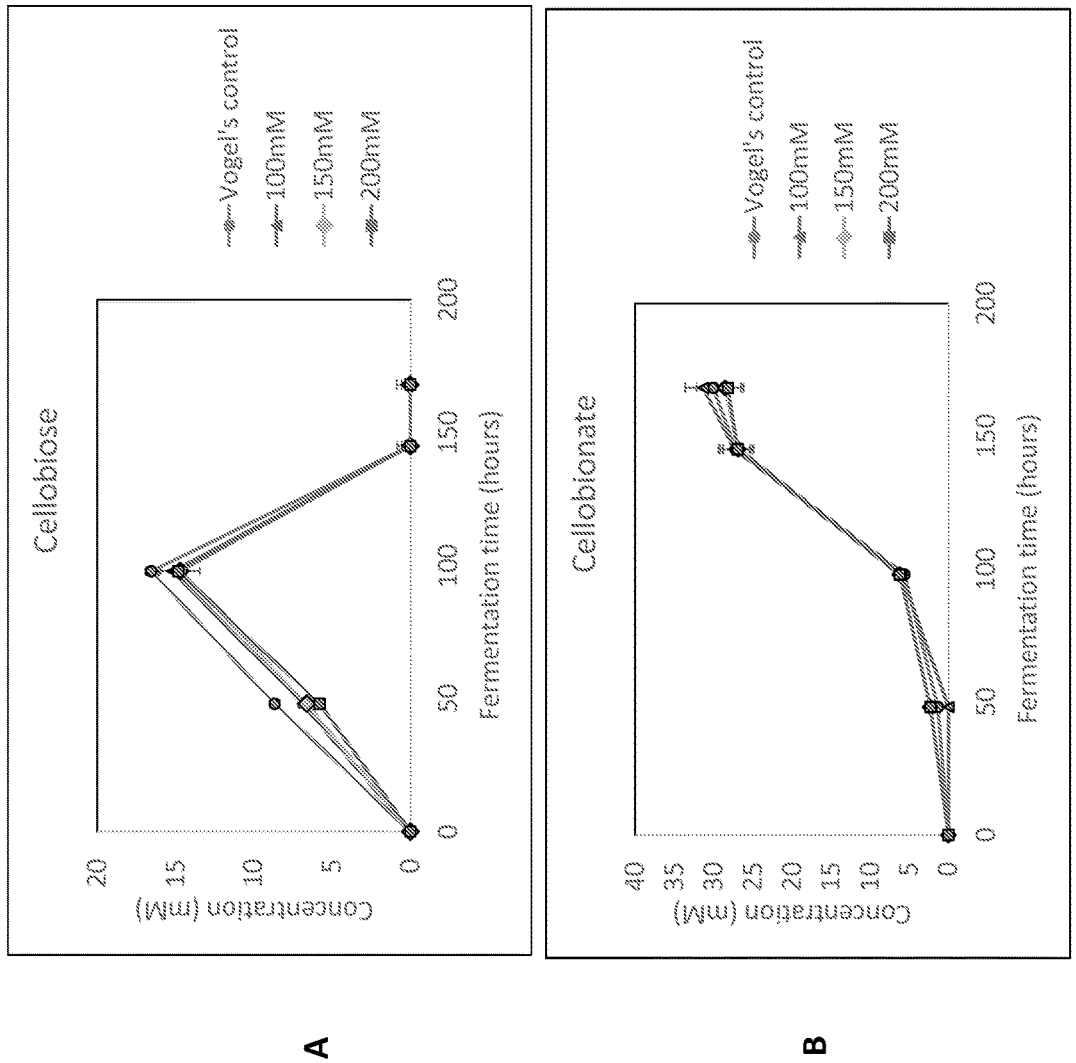
FIG. 18A and FIG. 18B illustrate the effect of potassium phosphate buffer concentration and the conversion of cellobiose to CBA via CDH-ABTS-laccase mediated conversion with the F5Δace-1Δcre-1ΔndvB strain in 1× Vogel's medium and 20 g/L Avicel. The values shown are the means of biological duplicates with the error bars representing the standard deviations.

When F5Δace-1Δcre-1ΔndvB is grown on 20 g/L Avicel, approximately 20 mM of cellobiose is produced along with 10 mM CBA. If laccase and ABTS are added to convert cellobiose to CBA, 30 mM of CBA is produced (Hildebrand A et al., 2014)(See Example 1). Because of the high level of CBA production, the pH rapidly drops from pH 6 to pH 4. The impact of buffering the fermentation medium was evaluated to determine the effect of this pH drop on the conversion of cellobiose to CBA. Three different concentrations of potassium phosphate buffer were evaluated to control the rate of pH drop and compared to the unbuffered Vogel's medium (FIG. 18A and FIG. 18B). In the case of the unbuffered Vogel's medium, the pH drops to 4 over the course of the fermentation. The addition of sodium phosphate buffer results in a slower decrease in pH and higher final pH as the buffer concentration increases. 200 mM potassium phosphate held the pH at 6 until the last day of fermentation where it dropped to 5.5. Although pH varied across the conditions tested, cellobiose and CBA production were not significantly affected. As a result, unbuffered Vogel's medium was used for the remainder of the fermentation experiments in this Example.

Production of the CBA with Laccase and ABTS Addition at Different Times

Figure 19:
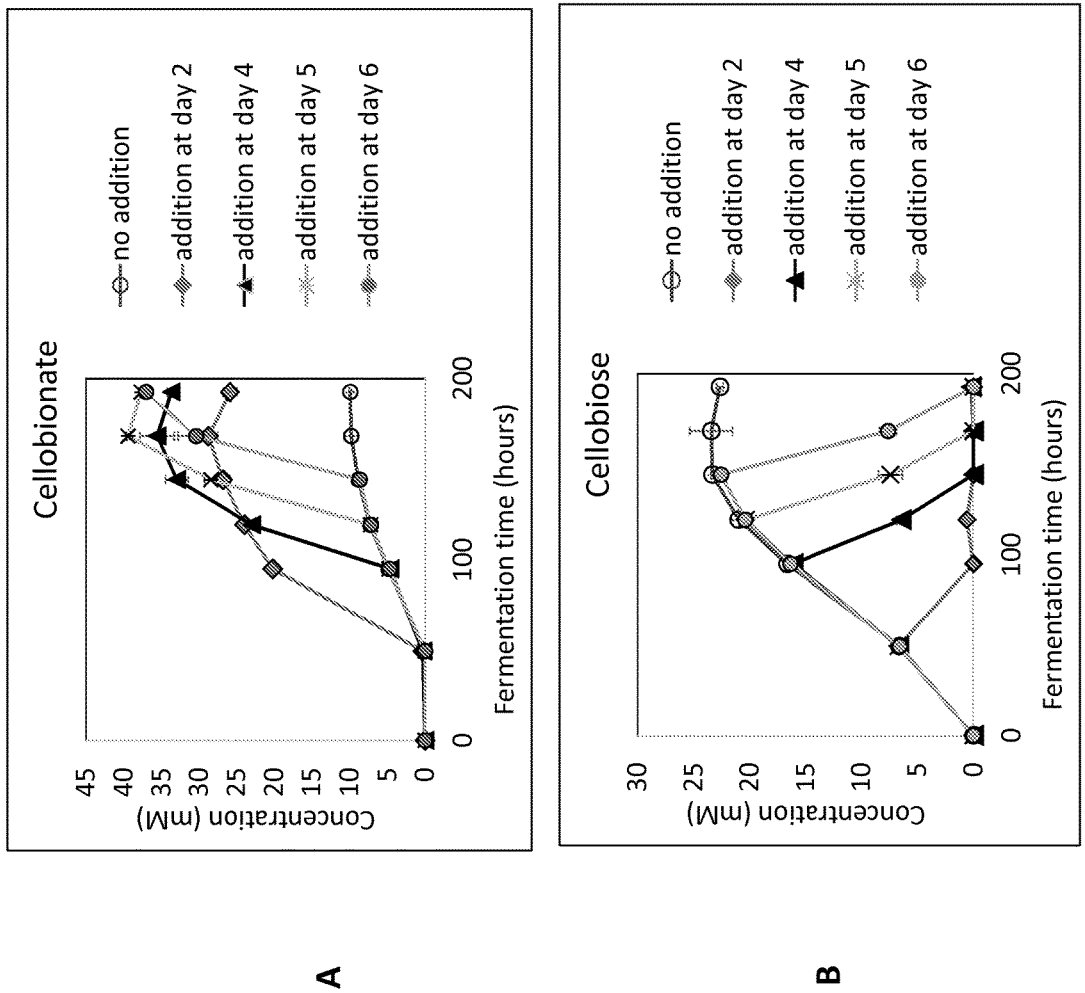
FIG. 19A and FIG. 19B illustrate optimization of laccase (0.05 U/mL) and ABTS (0.01 mM) addition time with the F5Δace-1Δcre-1ΔndvB strain grown in 1× Vogel's medium and 20 g/L Avicel. The values shown are the means of biological triplicates with the error bars representing the standard deviations.

The addition of laccase and ABTS to the fermentation system employing the F5Δace-1Δcre-1ΔndvB strain on 20 g/L Avicel was optimized. 0.05 U/mL of laccase and 0.01 mM ABTS were added at various time points. As shown in FIG. 19A and FIG. 19B, the cellobiose is completely converted to CBA within 48 hours for all addition times, with an optimal addition time at 120 hours into the fermentation.

The maximum CBA concentration occurs at 168 hours with a slight decrease after that for all cases. When no laccase and ABTS are added, maximum cellobiose concentration also occurs 168 hours into the fermentation, and cellobionate production reaches a plateau at that time point as well.

In a parallel experiment with laccase and ABTS addition 120 hours into the fermentation, flasks were harvested at 168 hours to quantify biomass production and Avicel utilization. The results, shown in Table 2, indicate that 67% of the Avicel is hydrolyzed, with 91% going toward CBA production and 4% going toward cell mass production. In the control case, where no laccase and ABTS are added, 62% of the Avicel is hydrolyzed, and a smaller fraction of the consumed Avicel goes toward CBA and cell mass production (29% and 3.3%, respectively). Without wishing to be bound by theory, the higher cellulose conversion in the case of with laccase and ABTS addition indicates that the conversion of cellobiose to CBA may relieve some cellulase inhibition by cellobiose, allowing for hydrolysis of the cello-oligosaccharides and subsequent conversion to CBA.

addition of the exogenously added laccase and ABTS, N. crassa was able to convert cellulose to CBA at very high yield. This Example showed that the native laccase produced by N. crassa works as efficiently as the P. ostreatus laccase. This opens up the possibility to engineer N. crassa to produce all the enzymes needed to convert cellulose to CBA. Homologous or heterologous expression of laccase in N. crassa could be achieved by engineering the native or heterologous laccase for expression under a constitutive or inducible promoter, allowing it to be produced under the tested fermentation conditions.

A report in the literature demonstrated over-expressing the native laccase in N. crassa at concentrations of 55 mg/L (Schilling B et al., 1992). Such concentrations would be adequate to allow for the efficient conversion of cellobiose to CBA in the presence of CDH and ABTS, and thus the overexpression of native N. crassa laccase may be done in the strains described herein. Also, one study showed that a laccase de-repressed mutant lah-1 produced laccase at levels even higher than when the wild type was induced with

TABLE 2

Percentage of Avicel hydrolyzed and the percentage directed toward fermentable products for the F5Δace-1Δcre-1ΔndvB strain grown on 20 g/L Avicel

| | Starting Avicel (g) | Residual Avicel (g) | Cellulose Conversion (%) | Mycelium produced (g) | Yield of cellobionate from consumed Avicel (mol/mol × 100%) | Yield of mycelium mass from consumed Avicel (g/g × 100%) |
|---|---|---|---|---|---|---|
| F5Δace-1Δcre-1ΔndvB With laccase/ABTS | 1.00 | 0.33 ± 0.008 | 67 ± 0.8% | 0.03 ± 0.001 | 91 ± 4% | 4.0 ± 0.2% |
| F5Δace-1Δcre-1ΔndvB No laccase/ABTS | 1.00 | 0.38 ± 0.002 | 62 ± 0.2% | 0.02 ± 0.001 | 29 ± 1% | 3.3 ± 0.2% |

Errors are calculated based upon standard deviations and error propagation theory.

In Vitro Assays with Native Laccase from N. crassa

In the experiments where exogenous laccase was added to the fermentation, the laccase host was Pleureotus ostreatus, a basidiomycete that expresses high levels of laccase (Okamoto K et al., 2000; More S et al., 2011). While N. crassa does have a native laccase, it is not naturally expressed, except under stress conditions that are not suitable for efficient fermentation. However, the suitability of using the native N. crassa laccase in the CDH-ABTS-laccase system for conversion of cellobiose to CBA was investigated.

Figure 20:
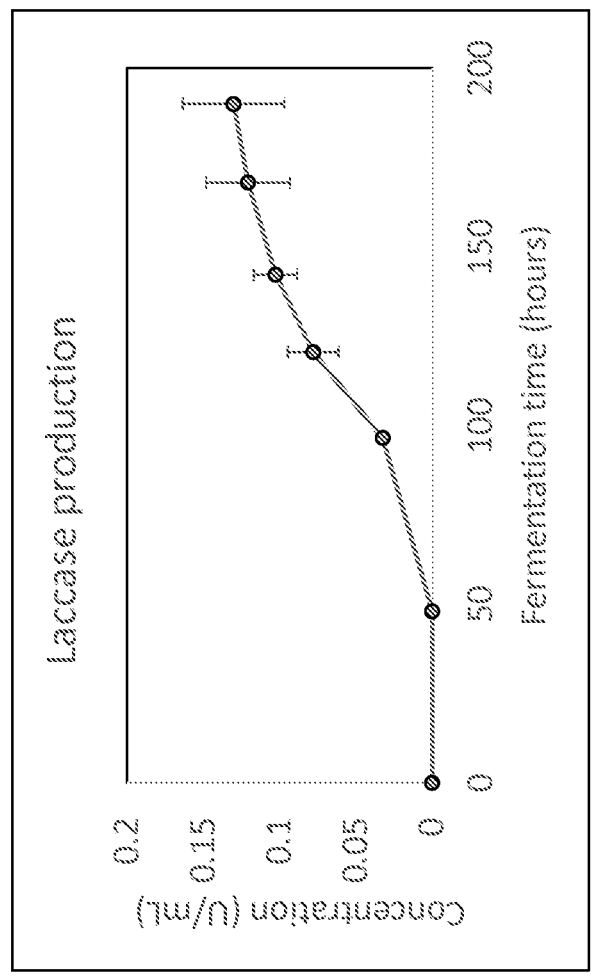
FIG. 20 illustrates laccase production by N. crassa with induction by 3 μM cycloheximide induction at 48 hours into the fermentation. Results shown are the means of biological triplicates with the error bars representing the standard deviations.

Cycloheximide, D-phenylalanine, and copper sulfate are possible inducers for the N. crassa laccase according to previous studies (Huber M et al., 1987; Linden R M et al., 1991; Froehner S C et al., 1974; Luke A K et al., 2001). To induce laccase in the N. crassa F5 strain, 3 µM cycloheximide was added after 48 hours of fermentation. After an additional 142 hours of fermentation, 0.15 U/mL of laccase was obtained, a suitable concentration to test in the cellobiose conversion system as shown in FIG. 20.

Figure 21:
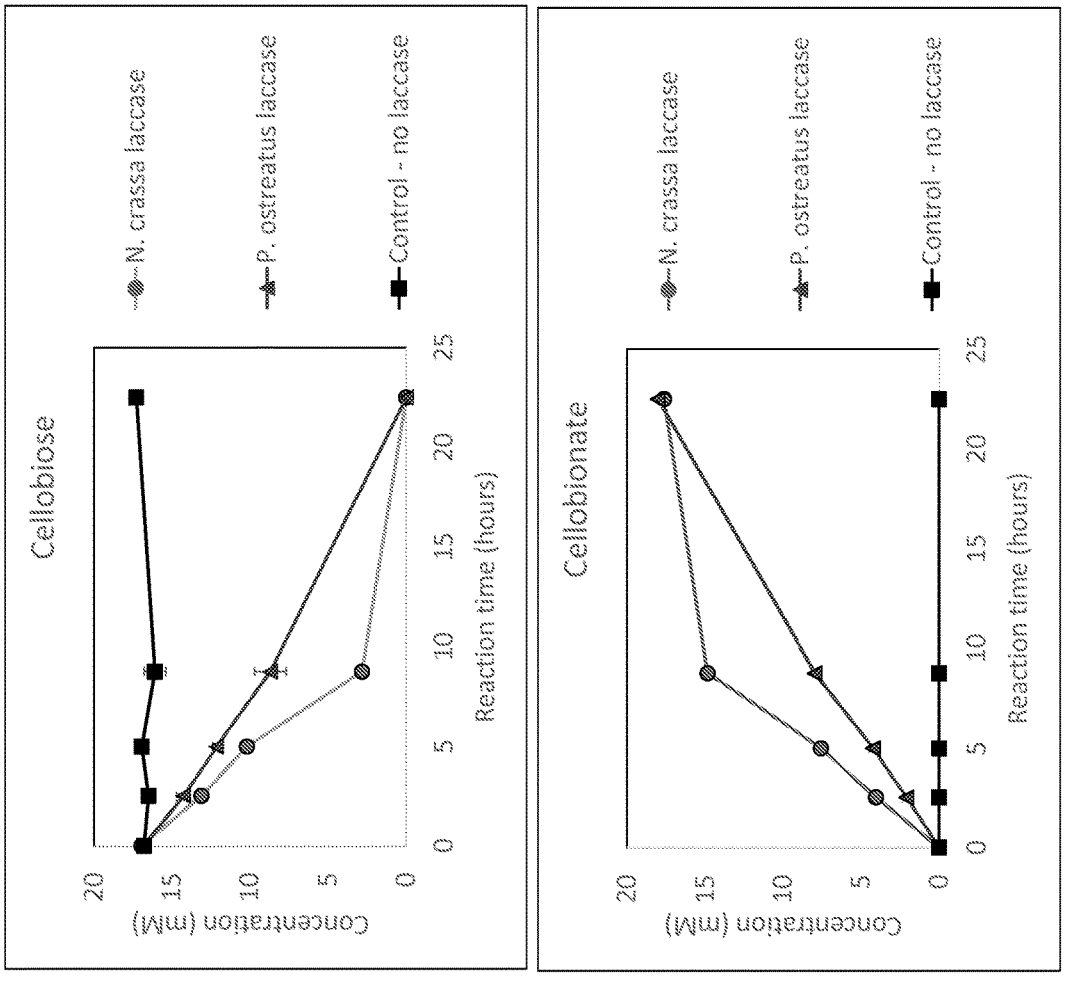
FIG. 21A and FIG. 21B illustrate comparisons of the N. crassa laccase to the P. ostreatus laccase in the conversion of cellobiose to CBA using the CDH-ABTS-laccase conversion system. The data shown are the means of biological duplicates with the error bars representing the standard deviations.

The produced laccase was tested against the P. ostreatus laccase in a falcon tube experiment (no cells), where cellobiose, CDH, and ABTS were added and the conversion of cellobiose to CBA was monitored as shown in FIG. 21A and FIG. 21B. The results indicate that the two laccases have comparable activities, both allowing for efficient conversion of cellobiose to CBA in the CDH-ABTS-laccase conversion system.

Cellulolytic fungi such as N. crassa can potentially produce all the enzymes needed to convert cellulose to CBA. N. crassa was able to produce cellulases and CDH. With the cycloheximide (Tamaru H et al., 1989). The de-repression was a result of a single mutation in an unknown gene mapped between nit-2 and leu-3 in linkage group I. Similarly de-repressing the F5Δace-1Δcre-1ΔndvB strain or overexpressing laccase in this strain could create a strain which would require only the addition of a low concentration of ABTS to produce CBA from cellulose.

In Vivo Assays with Native Laccase from N. crassa

Figure 22:
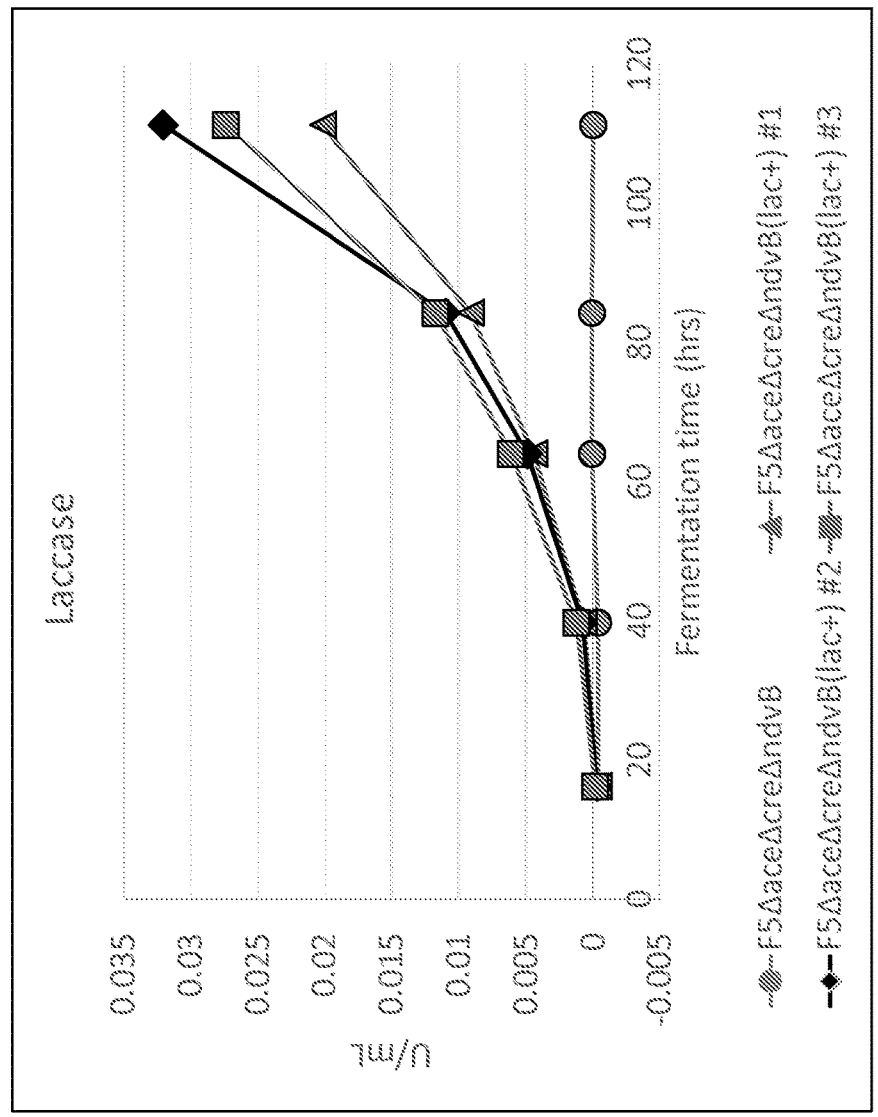
FIG. 22 illustrates laccase production by recombinant N. crassa strains.

The in vitro experiments with the endogenous N. crassa laccase as described above demonstrated the potential for overexpressing this endogenous gene in lieu of adding exogenous laccase in cellobionate production assays. To explore this, an N. crassa strain overexpressing the native N. crassa laccase gene was constructed as described above in the F5Δace-1Δcre-1ΔndvB strain background. The native laccase was successfully expressed when strains were grown on glucose. Three different strains produced about 0.03 U/mL laccase (FIG. 22). The best producing transformant, 2-2, was selected for additional analysis.

Figure 23:
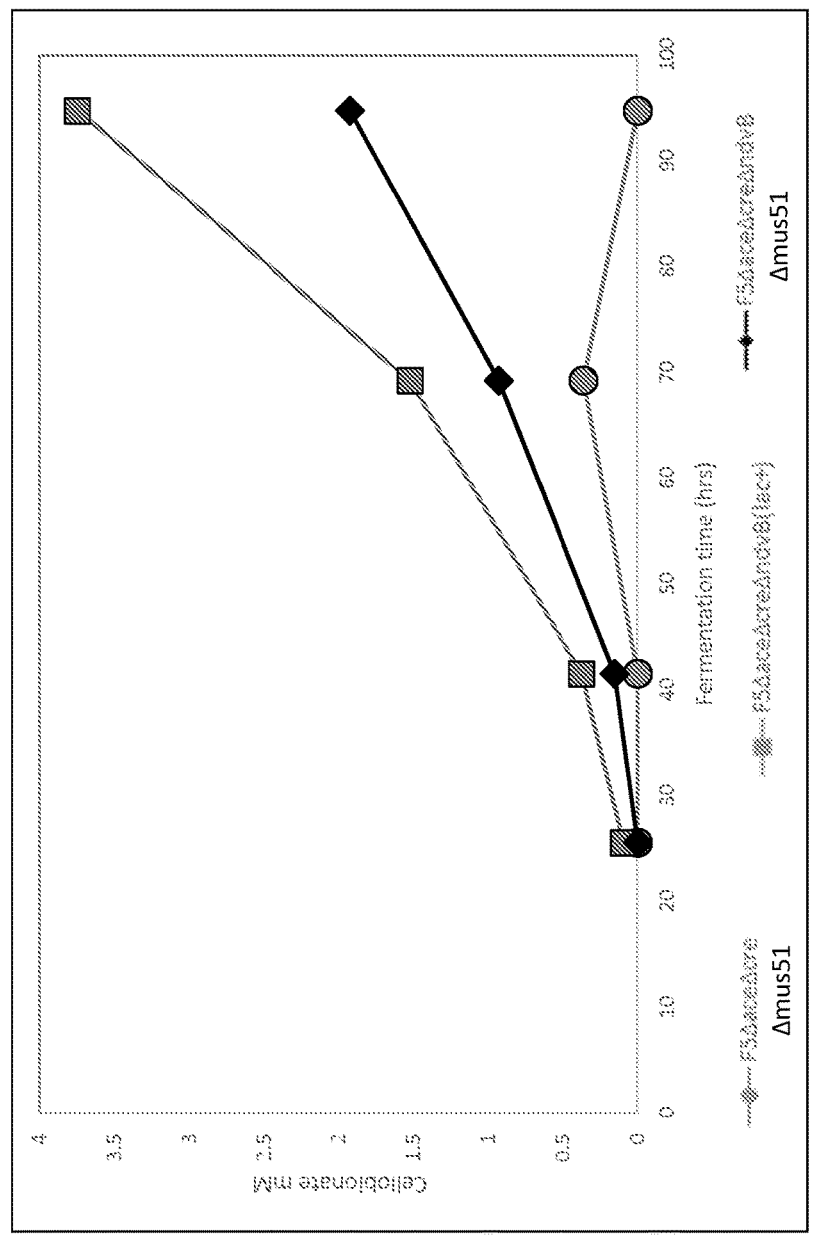
FIG. 23 illustrates cellobionate production in the indicated strains with ABTS addition (with ABTS addition at 0 hr).

Next, cellobionate production from Avicel by the recombinant strains was explored. As shown in FIG. 23, the strains overexpressing laccase (F5Δace-1Δcre-1ΔndvB (Lac+)) produced more cellobionate than the control strain (F5Δace-1Δcre-1ΔndvB Δmus51), which does not produce laccase. Both of these strains produced more cellobionate than F5Δace-1Δcre-1Δmus51. 0.1 mM of ABTS was added at the beginning of the fermentation.

Figure 24:
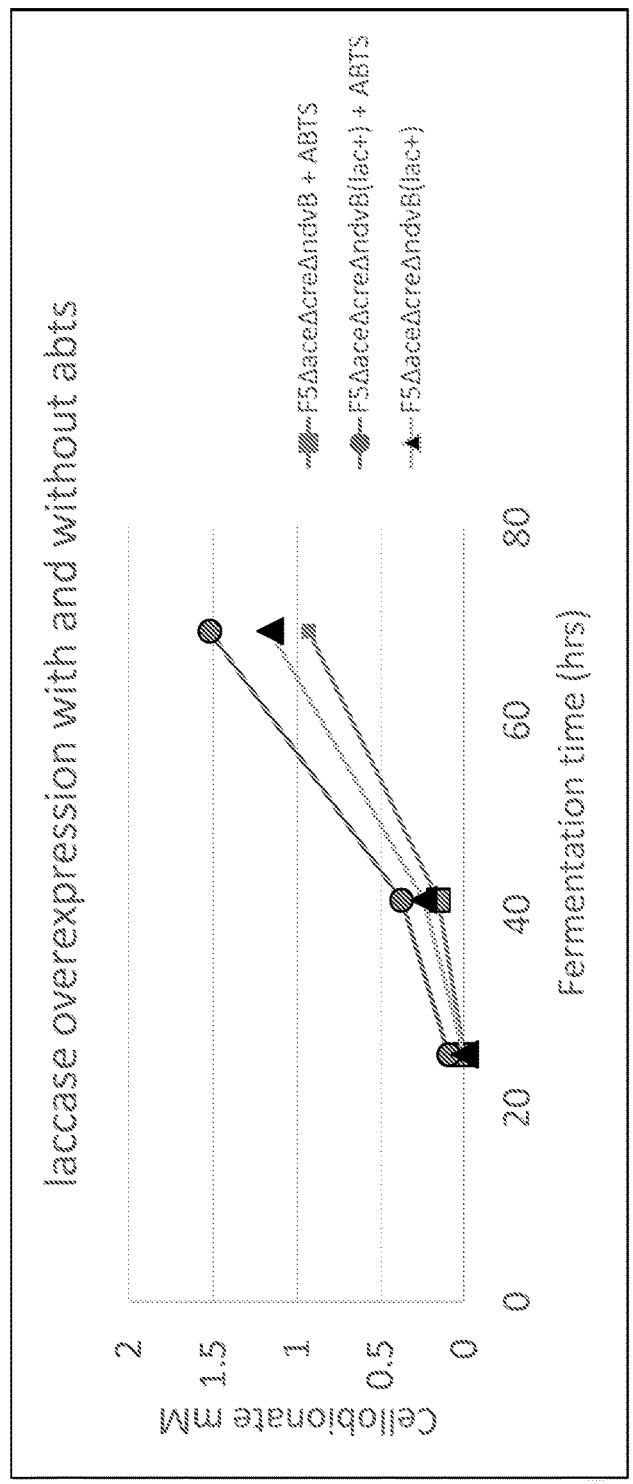
FIG. 24 illustrates cellobionate production in the indicated strains with or without the addition of ABTS.

The impact of adding ABTS on cellobionate production in the recombinant strain overexpressing the native N. crassa laccase was also examined. As can be seen in FIG. 24, the addition of ABTS increased the amount of the cellobionate produced in this strain (F5Δace-1Δcre-1ΔndvB (Lac+)). However, it was also observed that cellobionate could still be produced even without ABTS addition, indicating that some other reagents such as $FeSO_4$ in the medium could act as the electron mediator as well.

Discussion

ABTS was used as the redox mediator in the tested system. Although it is only needed in catalytic amount, it is very expensive for industrial application and an alternative low-cost redox mediator may be more preferable. A wide variety of inorganic metals and organic dyes may be used as redox mediators (Kunamneni, A et al., 2008). Noteworthy, lignin degradation products such as vanillin, ferulic acid or p-coumaric acid, which are generated as waste in the paper and pulp industry, have been demonstrated to be very efficient naturally-occurring laccase mediators (Camarero S et al., 2005; Cañas A et al., 2007; Camarero S et al., 2007; Gutíerrez A et al., 2007). These compounds could also be used as a cheap redox mediator source (Kunamneni, A et al., 2008). Further, if pretreated lignocellulosic biomass was used as the substrate instead of pure cellulose, these compounds may be naturally present in the feedstock stream, and the exogenous addition of a redox mediator could be potentially reduced or avoided.

Summary

This Example has demonstrated that CBA can be produced from cellulose by an engineered *N. crassa* strain with exogenous laccase addition or with overexpression of an endogenous laccase gene. The native laccase produced by *N. crassa* functioned as well as the exogenously added laccase. The tested strains are useful for microbial conversion of cellulose to CBA. The conversion concept is applicable to other industrially relevant cellulolytic fungi for CBA production from cheap feedstocks (e.g. cellulosic biomass).

REFERENCES

Lynd, L. R., Zyl, W. H., McBride, J. E., and Laser, M. (2005) Consolidated bioprocessing of cellulosic biomass: an update, Curr Opin Biotechnol.

Lynd, L. R., Weimer, P. J., van Zyl, W. H., and Pretorius, I. S. (2002) Microbial cellulose utilization: fundamentals and biotechnology, Microbiol Mol Biol Rev 66, 506-577, table of contents.

Lynd, L. R., Wyman, C. E., and Gerngross, T. U. (1999) Biocommodity Engineering, Biotechnol Prog 15, 777-793.

Lynd, L. R., Cushman, J. H., Nichols, R. J., and Wyman, C. E. (1991) Fuel Ethanol from Cellulosic Biomass, Science 251, 1318-1323.

Fan, Z., Wu, W., Hildebrand, A., Kasuga, T., Zhang, R., and Xiong, X. (2012) A novel biochemical route for fuels and chemicals production from cellulosic biomass. PLoS One 7, e31693.

Wu, W., Hildebrand, A., Kasuga, T., Xiong, X., and Fan, Z. (2013) Direct cellobiose production from cellulose using sextuple beta-glucosidase gene deletion *Neurospora crassa* mutants. Enzyme and Microbial Technology 52, 184-189.

Zhang, R., Fan, Z., and Kasuga, T. (2011) Expression of cellobiose dehydrogenase from *Neurospora crassa* in *Pichia pastoris* and its purification and characterization. Protein Expression and Purification 75, 63-69.

Szewczyk, E., Kasuga, T., and Fan, Z. (2013) Efficient sequential repetitive gene deletions in *Neurospora crassa*, employing self-excising beta-recombinase/six cassette. Journal of Microbiological Methods 92, 236-243.

Baminger, U., Ludwig, R., Galhaup, C., Leitner, C., Kulbe, K. D., and Haltrich, D. (2001) Continuous enzymatic regeneration of redox mediators used in biotransformation reactions employing flavoproteins. Journal of Molecular Catalysis B-Enzymatic 11, 541-550.

Jang Y-S, Kim B, Shin J H, Choi Y J, Choi S, et al. (2012) Bio-based production of C2-C6 platform chemicals. Biotechnol Bioeng 109: 2437-2459.

Sauer M, Porro D, Mattanovich D, Branduardi P (2008) Microbial production of organic acids: expanding the markets. Trends Biotechnol 26: 100-108.

Demain A L (2007) The business of biotechnology. Ind Biotechnol 3: 269-283.

Alonso S, Rendueles M, Díaz M (2013) Bio-production of lactobionic acid: current status, applications and future prospects. Biotechnol Adv 31: 1275-1291.

Miyamoto Y, Ooi T, Kinoshita S (2000) Production of lactobionic acid from whey by *Pseudomonas* sp. LS13-1. Biotechnol Lett 22: 427-430.

Meiberg J, P M B, Sloots B (1990) A process for the fermentative oxidation of reducing disaccharides. EP 0384534 A1

Murakami H, Kiryu T, Kiso T, Nakano H (2006) Production of Aldonic Acids from Monosaccharides by Washed Cells of *Burkholderia cepacia* and their Calcium Binding Capability. J Appl glycosci 279: 277-279.

Murakami H, Seko A, Azumi M, Ueshima N, Yoshizumi H, et al. (2003) Fermentative Production of Lactobionic Acid by *Burkholderia cepacia*. J Appl glycosci 120: 117-120.

Pedruzzi I, da Silva E A B, Rodrigues A E (2011) Production of lactobionic acid and sorbitol from lactose/fructose substrate using GFOR/GL enzymes from *Zymomonas mobilis* cells: a kinetic study. Enzyme Microb Technol 49: 183-191.

Malvessi E, Carra S, Pasquali F C, Kern D B, da Silveira M M, et al. (2013) Production of organic acids by periplasmic enzymes present in free and immobilized cells of *Zymomonas mobilis*. J Ind Microbiol Biotechnol 40: 1-10.

Kiryu T, Yamauchi K, Masuyama A, Ooe K, Kimura T, et al. (2012) Optimization of Lactobionic Acid Production by *Acetobacter orientalis* Isolated from Caucasian Fermented Milk, "Caspian Sea Yogurt." Biosci Biotechnol Biochem 76: 361-363.

Alonso S, Rendueles M, Díaz M (2011) Efficient lactobionic acid production from whey by *Pseudomonas taetrolens* under pH-shift conditions. Bioresour Technol 102: 9730-9736.

Alonso S, Rendueles M, Díaz M (2012) Role of dissolved oxygen availability on lactobionic acid production from whey by *Pseudomonas taetrolens*. Bioresour Technol 109: 140-147.

Alonso S, Rendueles M, Díaz M (2013) Feeding strategies for enhanced lactobionic acid production from whey by *Pseudomonas taetrolens*. Bioresour Technol 134: 134-142.

Henriksson G, Johansson G, Pettersson G (2000) A critical review of cellobiose dehydrogenases. J Biotechnol 78: 93-113.

Roy B P, Dumonceaux T, Koukoulas A A, Archibald F S (1996) Purification and Characterization of Cellobiose Dehydrogenases from the White Rot Fungus *Trametes versicolor*. Appl Environ Microbiol 62: 4417-4427.

Bao W, Usha S N, Renganathan V (1993) Purification and characterization of cellobiose dehydrogenase, a novel extracellular hemoflavoenzyme from the white-rot fungus *Phanerochaete chrysosporium*. Arch Biochem Biophys 300: 705-713.

Baminger U, Ludwig R, Galhaup C, Leitner C, Kulbe K D, et al. (2001) Continuous enzymatic regeneration of redox mediators used in biotransformation reactions employing flavoproteins. J Mol Catal B Enzym 11: 541-550.

Madhavi V, Lele S S (2009) Laccase: properties and applications. 4: 1694-1717. Arora D S, Sharma R K, Singh Arora D, Kumar Sharma R (2010) Ligninolytic fungal laccases and their biotechnological applications. Appl Biochem Biotechnol 160: 1760-1788.

Van Hecke W, Bhagwat A, Ludwig R R, Dewulf J, Haltrich D, et al. (2009) Kinetic Modeling of a Bi-Enzymatic System for Efficient Conversion of Lactose to Lactobionic Acid. Biotechnol Bioeng 102: 1475-1482.

Lynd L R, Cushman J, Nichols R, Wyman C (1991) Fuel ethanol from cellulosic biomass. Science 251: 1318-1323.

Fan Z, Wu W, Hildebrand A, Kasuga T, Zhang R, et al. (2012) Novel Biochemical Route for Fuels and Chemicals production from Cellulosic Biomass. PLoS One 7: 8.

Wu W, Hildebrand A, Kasuga T, Xiong X, Fan Z (2013) Direct cellobiose production from cellulose using sextuple beta-glucosidase gene deletion *Neurospora crassa* mutants. Enzyme Microb Technol 52: 184-189.

Hildebrand A, Szewczyk E, Lin H, Kasuga T, Fan J (2014) Engineering *Neurospora crassa* for improved cellobiose and cellobionate production. Appl Environ Microbiol: In press.

McCluskey K, Wiest A, Plamann M (2010) The fungal genetics stock center: A repository for 50 years of fungal genetics research. J Biosci 35: 119-126.

Zhang R, Fan Z, Kasuga T (2011) Expression of cellobiose dehydrogenase from *Neurospora crassa* in *Pichia pastoris* and its purification and characterization. Protein Expr Purif 75: 63-69.

Huber M, Lerch K (1987) The influence of copper on the induction of tyrosinase and laccase in *Neurospora crassa*. 219: 335-338.

Linden R M, Schilling B C, Germann U a, Lerch K (1991) Regulation of laccase synthesis in induced *Neurospora crassa* cultures. Curr Genet 19: 375-381.

Froehner S C, Eriksson K E (1974) Induction of *Neurospora crassa* laccase with protein synthesis inhibitors. J Bacteriol 120: 450-457.

Baminger U, Nidetzky B, Kulbe K D, Haltrich D (1999) A simple assay for measuring cellobiose dehydrogenase activity in the presence of laccase. 35: 253-259.

Gessner M O, Bauchrowitz M A, Escautier M, Renouvelables R, Marvig J (1991) Extraction and quantification of ergosterol as a measure of fungal biomass in leaf litter. Microb Ecol: 285-291.

Okamoto K, Yanagi S O, Sakai T (2000) Purification and characterization of extracellular laccase from *Pleurotus ostreatus*. Mycoscience 41: 7-13.

More S, S. RP, K. P, M. S, S. Malini, et al. (2011) Isolation, Purification, and Characterization of Fungal Laccase from *Pleurotus* sp. Enzyme Res 2011: 7.

Luke A K, Burton S G (2001) A novel application for *Neurospora crassa*: Progress from batch culture to a membrane bioreactor for the bioremediation of phenols. Enzyme Microb Technol 29: 348-356.

Schilling B, Linden R M, Kupper U, Lerch K (1992) Expression of *Neurospora crassa* laccase under the control of the copper-inducible metallothionein-promoter. Curr Genet 22: 197-203.

Tamaru H, Inoue H (1989) Isolation and characterization of a laccase-derepressed mutant of *Neurospora crassa*. J Bacteriol 171: 6288-6293.

Kunamneni, A., Camarero, S., Garcia-Burgos, C., Plou, F. J., Ballesteros, A., and Alcalde, M. (2008) Engineering and Applications of fungal laccases for organic synthesis, *Microbial cell factories* 7, 17.

Camarero S, Ibarra D, Martínez M J, Martínez A T. Lignin-derived compounds as efficient laccase mediators for decolorization of different types of recalcitrant dyes. Appl Environ Microbiol. 2005; 71:1775-1784.

Cañas A, Alcalde M, Plou F J, Martínez M J, Martínez A T, Camarero S. Transformation of polycyclic aromatic hydrocarbons by laccase is strongly enhanced by phenolic compounds present in soil. Environ Sci Technol. 2007; 41:2964-2971.

Camarero S, Ibarra D, Martínez A T, Romero J, Gutíerrez A, del Río J C. Paper pulp delignification using laccase and natural mediators. Enzyme Microb Technol. 2007; 40:1264-1271.

Gutíerrez A, Rencores J, Ibarra D, Molina S, Camarero S, Romero J, del Río J C, Martínez A T. Removal of lipophilic extractives from paper pulp by laccase and lignin-derived phenols as natural mediators. Environ Sci Technol. 2007; 41:4124-4129.

What is claimed is:

1. A method of producing cellobionate, the method comprising:
   a) providing an *N. crassa* cell comprising:
      a knockout mutation in each of NCU00130 (SEQ ID NO: 2), NCU04952 (SEQ ID NO: 4), NCU05577 (SEQ ID NO: 6), NCU07487 (SEQ ID NO: 8), NCU08755 (SEQ ID NO: 10), and NCU03641 (SEQ ID NO: 12) genes;
      a knockout mutation in the NCU09425 (SEQ ID NO: 14) gene;
      a knockout mutation in each of NCU08807 (SEQ ID NO: 16) and NCU09333 (SEQ ID NO: 18) genes, and;
   b) culturing the cell in a medium comprising cellulose, whereby the cell produces cellobionate from the cellulose.

2. The method of claim 1, further comprising a step of purifying the cellobionate from the medium.

3. The method of claim 1, wherein consumption of cellobionate by the cell is reduced by at least 80% as compared to a corresponding wild type cell.

4. The method of claim 1, wherein the cell is cultured in the presence of an exogenous source of laccase.

5. The method of claim 2, wherein the cell is cultured in the presence of an exogenous source of cellobiose dehydrogenase.

6. The method of claim 2, wherein the medium further comprises a redox mediator.

7. The method of claim 1, wherein the cell further comprises a laccase having increased expression or activity as compared to a wild type *N. crassa* cell.

* * * * *

SEQUENCE LISTING

```
<160> NUMBER OF SEQ ID NOS: 24

<210> SEQ ID NO 1
<211> LENGTH: 476
<212> TYPE: PRT
<213> ORGANISM: Neurospora crassa

<400> SEQUENCE: 1

Met Ser Leu Pro Lys Asp Phe Leu Trp Gly Phe Ala Thr Ala Ala Tyr
1               5                   10                  15

Gln Ile Glu Gly Ala Ile His Ala Asp Gly Arg Gly Pro Ser Ile Trp
            20                  25                  30

Asp Thr Phe Cys Asn Ile Pro Gly Lys Ile Ala Asp Gly Ser Ser Gly
        35                  40                  45

Ala Val Ala Cys Asp Ser Tyr Asn Arg Thr Lys Glu Asp Ile Asp Leu
    50                  55                  60
```

-continued

```
Leu Lys Ser Leu Gly Ala Thr Ala Tyr Arg Phe Ser Ile Ser Trp Ser
 65                  70                  75                  80

Arg Ile Ile Pro Val Gly Gly Arg Asn Asp Pro Ile Asn Gln Lys Gly
                 85                  90                  95

Ile Asp His Tyr Val Lys Phe Val Asp Asp Leu Leu Glu Ala Gly Ile
            100                 105                 110

Thr Pro Phe Ile Thr Leu Phe His Trp Asp Leu Pro Asp Gly Leu Asp
        115                 120                 125

Lys Arg Tyr Gly Gly Leu Leu Asn Arg Glu Glu Phe Pro Leu Asp Phe
    130                 135                 140

Glu His Tyr Ala Arg Thr Met Phe Lys Ala Ile Pro Lys Cys Lys His
145                 150                 155                 160

Trp Ile Thr Phe Asn Glu Pro Trp Cys Ser Ser Ile Leu Gly Tyr Asn
                165                 170                 175

Ser Gly Tyr Phe Ala Pro Gly His Thr Ser Asp Arg Thr Lys Ser Pro
            180                 185                 190

Val Gly Asp Ser Ala Arg Glu Pro Trp Ile Val Gly His Asn Leu Leu
        195                 200                 205

Ile Ala His Gly Arg Ala Val Lys Val Tyr Arg Glu Asp Phe Lys Pro
    210                 215                 220

Thr Gln Gly Gly Glu Ile Gly Ile Thr Leu Asn Gly Asp Ala Thr Leu
225                 230                 235                 240

Pro Trp Asp Pro Glu Asp Pro Leu Asp Val Glu Ala Cys Asp Arg Lys
                245                 250                 255

Ile Glu Phe Ala Ile Ser Trp Phe Ala Asp Pro Ile Tyr Phe Gly Lys
            260                 265                 270

Tyr Pro Asp Ser Met Arg Lys Gln Leu Gly Asp Arg Leu Pro Glu Phe
        275                 280                 285

Thr Pro Glu Glu Val Ala Leu Val Lys Gly Ser Asn Asp Phe Tyr Gly
    290                 295                 300

Met Asn His Tyr Thr Ala Asn Tyr Ile Lys His Lys Lys Gly Val Pro
305                 310                 315                 320

Pro Glu Asp Asp Phe Leu Gly Asn Leu Glu Thr Leu Phe Tyr Asn Lys
                325                 330                 335

Lys Gly Asn Cys Ile Gly Pro Glu Thr Gln Ser Phe Trp Leu Arg Pro
            340                 345                 350

His Ala Gln Gly Phe Arg Asp Leu Leu Asn Trp Leu Ser Lys Arg Tyr
        355                 360                 365

Gly Tyr Pro Lys Ile Tyr Val Thr Glu Asn Gly Thr Ser Leu Lys Gly
    370                 375                 380

Glu Asn Ala Met Pro Leu Lys Gln Ile Val Glu Asp Asp Phe Arg Val
385                 390                 395                 400

Lys Tyr Phe Asn Asp Tyr Val Asn Ala Met Ala Lys Ala His Ser Glu
                405                 410                 415

Asp Gly Val Asn Val Lys Gly Tyr Leu Ala Trp Ser Leu Met Asp Asn
            420                 425                 430

Phe Glu Trp Ala Glu Gly Tyr Glu Thr Arg Phe Gly Val Thr Tyr Val
        435                 440                 445

Asp Tyr Glu Asn Asp Gln Lys Arg Tyr Pro Lys Lys Ser Ala Lys Ser
    450                 455                 460

Leu Lys Pro Leu Phe Asp Ser Leu Ile Lys Lys Asp
465                 470                 475
```

<210> SEQ ID NO 2
<211> LENGTH: 1431
<212> TYPE: DNA
<213> ORGANISM: Neurospora crassa

<400> SEQUENCE: 2

```
atgtctcttc ctaaggattt cctctggggc ttcgctactg cggcctatca gattgagggt      60
gctatccacg ccgacggccg tggcccctct atctgggata cttctctgcaa cattcccggt    120
aaaatcgccg acggcagctc tggtgccgtc gcctgcgact cttacaaccg caccaaggag    180
gacattgacc tcctcaagtc tctcggcgcc accgcctacc gcttctccat ctcctggtct    240
cgcatcatcc ccgttggtgg tcgcaacgac cccatcaacc agaagggcat cgaccactat    300
gtcaagtttg tcgatgacct gctcgaggct ggtattaccc cctttatcac cctcttccac    360
tgggatcttc ccgatggtct cgacaagcgc tacggcggtc ttctgaaccg tgaagagttc    420
cccctcgact ttgagcacta cgcccgcact atgttcaagg ccattcccaa gtgcaagcac    480
tggatcacct tcaacgagcc ctggtgcagc tccatcctcg ctacaactc gggctacttt    540
gcccctggcc acacctccga ccgtaccaag tcacccgttg gtgacagcgc tcgcgagccc    600
tggatcgtcg gccataacct gctcatcgct cacgggcgtg ccgtcaaggt gtaccgagaa    660
gacttcaagc ccacgcaggg cggcgagatc ggtatcacct tgaacggcga cgccactctt    720
cccctgggatc cagaggaccc cttggacgtc gaggcgtgcg accgcaagat tgagttcgcc    780
atcagctggt tcgcagaccc catctacttt ggaaagtacc ccgactcgat gcgcaaacag    840
ctcggtgacc ggctgcccga gtttacgccc gaggaggtgg cgcttgtcaa gggttccaac    900
gacttctacg gcatgaacca ctacacagcc aactacatca gcacaagaa gggcgtccct    960
cccgaggacg acttcctcgg caacctcgag acgctcttct acaacaagaa gggtaactgc   1020
atcgggcccg agacccagtc gttctggctc cggccgcacg cccagggctt ccgcgacctg   1080
ctcaactggc tcagcaagcg ctacggatac cccaagatct acgtgaccga gaacgggacc   1140
agtctcaagg gcgagaacgc catgccgctc aagcaaattg tcgaggacga cttccgcgtc   1200
aagtacttca cgactacgt caacgccatg gccaaggcgc atagcgagga cggcgtcaac   1260
gtcaagggat atcttgcctg gagcttgatg gacaactttg agtgggccga gggctatgag   1320
acgcggttcg gcgttaccta tgtcgactat gagaacgacc agaagaggta ccccaagaag   1380
agcgccaaga gcttgaagcc gctctttgac tctttgatca agaaggacta a             1431
```

<210> SEQ ID NO 3
<211> LENGTH: 735
<212> TYPE: PRT
<213> ORGANISM: Neurospora crassa

<400> SEQUENCE: 3

```
Met His Leu Arg Ile Phe Ala Val Leu Ala Ala Thr Ser Leu Ala Trp
1               5                   10                  15

Ala Glu Thr Ser Glu Lys Gln Ala Arg Gln Ala Gly Ser Gly Phe Ala
            20                  25                  30

Ala Trp Asp Ala Ala Tyr Ser Gln Ala Ser Thr Ala Leu Ser Lys Leu
        35                  40                  45

Ser Gln Gln Asp Lys Val Asn Ile Val Thr Gly Val Gly Trp Asn Lys
    50                  55                  60

Gly Pro Cys Val Gly Asn Thr Pro Ala Ile Ala Ser Ile Gly Tyr Pro
65                  70                  75                  80
```

-continued

Gln Leu Cys Leu Gln Asp Gly Pro Leu Gly Ile Arg Phe Gly Gly Ser
                85                  90                  95

Val Thr Ala Phe Thr Pro Gly Ile Gln Ala Ala Ser Thr Trp Asp Val
            100                 105                 110

Glu Leu Ile Arg Gln Arg Gly Val Tyr Leu Gly Ala Glu Ala Arg Gly
            115                 120                 125

Val Gly Val His Val Leu Leu Gly Pro Val Ala Gly Ala Leu Gly Lys
130                 135                 140

Ile Pro Asn Gly Gly Arg Asn Trp Glu Gly Phe Gly Pro Asp Pro Tyr
145                 150                 155                 160

Leu Thr Gly Ile Ala Met Ser Glu Thr Ile Glu Gly Ile Gln Ser Asn
                165                 170                 175

Gly Val Gln Ala Cys Ala Lys His Phe Ile Leu Asn Glu Gln Glu Thr
            180                 185                 190

Asn Arg Asp Thr Ile Ser Ser Val Val Asp Asp Arg Thr Met His Glu
            195                 200                 205

Leu Tyr Leu Phe Pro Phe Ala Asp Ala Val His Ser Asn Val Ala Ser
210                 215                 220

Val Met Cys Ser Tyr Asn Lys Val Asn Gly Thr Trp Ala Cys Glu Asn
225                 230                 235                 240

Asp Lys Ile Gln Asn Gly Leu Leu Lys Lys Glu Leu Gly Phe Lys Gly
                245                 250                 255

Tyr Val Met Ser Asp Trp Asn Ala Gln His Thr Thr Asn Gly Ala Ala
            260                 265                 270

Asn Ser Gly Met Asp Met Thr Met Pro Gly Ser Asp Phe Asn Gly Lys
            275                 280                 285

Thr Ile Leu Trp Gly Pro Gln Leu Asn Thr Ala Val Asn Asn Gly Gln
290                 295                 300

Val Ser Lys Ala Arg Leu Asp Asp Met Ala Lys Arg Ile Leu Ala Ser
305                 310                 315                 320

Trp Tyr Leu Leu Glu Gln Asn Ser Gly Tyr Pro Ala Thr Asn Leu Lys
                325                 330                 335

Ala Asn Val Gln Gly Asn His Lys Glu Asn Val Arg Ala Val Ala Arg
            340                 345                 350

Asp Gly Ile Val Leu Leu Lys Asn Asp Asn Ile Leu Pro Leu Lys
            355                 360                 365

Lys Pro Ser Lys Leu Ala Ile Ile Gly Ser Ser Val Val Asn Pro
            370                 375                 380

Ala Gly Arg Asn Ala Cys Thr Asp Arg Gly Cys Asn Thr Gly Ala Leu
385                 390                 395                 400

Gly Met Gly Trp Gly Ser Gly Thr Ala Asp Tyr Pro Tyr Phe Val Ala
                405                 410                 415

Pro Tyr Asp Ala Leu Lys Thr Arg Ala Gln Ser Asp Gly Thr Thr Val
            420                 425                 430

Asn Leu Leu Ser Ser Asp Ser Thr Ser Gly Val Ala Asn Ala Ala Ser
            435                 440                 445

Gly Ala Asp Ala Ala Leu Val Phe Ile Thr Ala Asp Ser Gly Glu Gly
            450                 455                 460

Tyr Ile Thr Val Glu Gly Val Thr Gly Asp Arg Pro Asn Leu Asp Pro
465                 470                 475                 480

Trp His Asn Gly Asn Gln Leu Val Gln Ala Val Ala Gln Ala Asn Lys
                485                 490                 495

Asn Thr Ile Val Val Val His Ser Thr Gly Pro Ile Ile Leu Glu Thr

```
                500             505             510
Ile Leu Ala Gln Pro Gly Val Lys Ala Val Val Trp Ala Gly Leu Pro
            515                 520                 525

Ser Gln Glu Asn Gly Asn Ala Leu Val Asp Val Leu Tyr Gly Leu Val
            530                 535             540

Ser Pro Ser Gly Lys Leu Pro Tyr Thr Ile Ala Lys Ser Glu Ser Asp
545                 550                 555                 560

Tyr Gly Thr Ala Val Gln Arg Gly Gly Thr Asp Leu Phe Thr Glu Gly
                565                 570                 575

Leu Phe Ile Asp Tyr Arg His Phe Asp Lys Asn Gly Ile Ala Pro Arg
            580                 585                 590

Tyr Glu Phe Gly Phe Gly Leu Ser Tyr Thr Asn Phe Thr Tyr Ser Ser
            595                 600                 605

Leu Ser Ile Thr Ser Thr Ala Ser Ser Gly Pro Ala Ser Gly Asp Thr
            610                 615                 620

Ile Pro Gly Gly Arg Ala Asp Leu Trp Glu Thr Val Ala Thr Val Thr
625                 630                 635                 640

Ala Val Val Lys Asn Thr Gly Gly Val Gln Gly Ala Glu Ala Pro Gln
                645                 650                 655

Leu Tyr Ile Thr Leu Pro Ser Ser Ala Pro Ser Ser Pro Pro Lys Gln
                660                 665                 670

Leu Arg Gly Phe Ala Lys Leu Lys Leu Ala Pro Gly Glu Ser Lys Thr
                675                 680                 685

Ala Thr Phe Ile Leu Arg Arg Arg Asp Leu Ser Tyr Trp Asp Thr Gly
            690                 695                 700

Ser Gln Asn Trp Val Val Pro Ser Gly Ser Phe Gly Val Val Val Gly
705                 710                 715                 720

Ala Ser Ser Arg Asp Leu Arg Leu Asn Gly Lys Phe Asp Val Tyr
                725                 730                 735

<210> SEQ ID NO 4
<211> LENGTH: 2208
<212> TYPE: DNA
<213> ORGANISM: Neurospora crassa

<400> SEQUENCE: 4
atgcaccttc gaatatttgc ggtgttggcc gcgacttccc tcgcctgggc cgagactagc      60
gagaaacaag ctcgtcaagc tggctcaggt tttgcggcgt gggacgcagc ctattctcag     120
gcaagcactg ctctctccaa gctttcacag caagacaagg tcaacatcgt caccggagtc     180
ggctggaata agggcccatg tgttggcaac accccagcta ttgcatcaat cggttatccc     240
cagctctgtt tacaagacgg ccctctcggc attcggtttg gaggaagtgt caccgcgttc     300
acgcctggta tccaggcggc ttcaacatgg gacgtcgaac tgattcgaca gcgcggcgtc     360
tacctcggtg cagaagccag aggggttggc gtacatgtcc ttcttggacc cgtggccgga     420
gcgcttggca agatccccaa tggtggacgt aactgggagg ctttggtcc ggatccctac      480 ctcacaggta ttgccatgag cgaaacaatt gaagggatcc agagcaatgg tgtacaagct     540
tgcgccaagc acttcattct caacgaacag gagacaaacc gcgatactat cagcagtgtc     600
gtcgacgacc gcaccatgca tgaactatac ctcttcccct tgccgatgc cgtacactca      660 aatgttgcaa gtgtgatgtg cagctacaac aaggtcaacg tacgtgggc atgtgagaat      720 gacaaaatcc agaatggcct tctcaagaaa gagctaggct tcaaaggata tgtcatgagt     780
gattggaacg cccagcacac cacgaacggc gctgcaaaca gtggtatgga tatgacgatg     840
```

```
ccaggcagtg actttaatgg caagacgatc ctgtggggac cacagctcaa caccgccgtc    900
aacaatggcc aggtctccaa agcaagactg gacgacatgg ccaagcgcat tctcgcatcg    960
tggtatttac tcgagcaaaa ctcaggctac cctgcgacta acctcaaggc caatgttcaa   1020
ggaaaccaca aggagaacgt tcgcgcagtg gcaagagacg gcattgttct gctgaagaac   1080
gacgataaca tcctcccgct caagaagcct agcaagctgg caatcattgg gtcatcgtcc   1140
gttgtcaacc ctgcgggaag gaacgcctgc accgatcgag gatgcaacac cggtgcgctc   1200
ggcatgggtt ggggctccgg cacggccgat taccoctact tcgtagcacc ctatgatgct   1260
ctcaagacgc gggctcagtc cgacggaaca actgtcaacc tactcagctc tgacagcacc   1320
agcggcgtag ccaacgctgc ctccggagcc gacgcggcac tagtcttcat cacagccgat   1380
tccggcgaag gctacatcac ggtcgagggc gtgaccggcg accgtcccaa cctcgatccc   1440
tggcacaacg gcaaccagct agtccaagcc gtggctcaag ccaacaagaa caccattgtc   1500
gtcgtccaca gtaccggccc catcattctg gagactatcc tcgcgcagcc gggcgtcaag   1560
gcggtcgtgt gggccggtct ccccagccaa gagaacggca acgcccttgt cgatgtccta   1620
tacggcttgg tctctcccte gggtaagctg ccgtatacta tcgccaagag cgaaagcgac   1680
tacggcactg ccgtgcaaag ggagggacg gatctgttca ctgagggtct gttcatcgat   1740
taccgccact ttgacaagaa cggtatcgct ccccggtatg agttcggttt cggtctttcc   1800
tacacgaact tcacctactc ctccctctcc atcacctcca ccgcctcctc cggtcccgcc   1860
tcgggtgaca ccatccctgg cggccgcgcc gacctctggg aaaccgtggc aaccgtcact   1920
gccgtcgtca aaaacacggg tggtgtgcag ggcgccgagg caccccagct atacatcacc   1980
ttgccctctt ccgcgccgtc gagcccgccg aaacagctca gagggtttgc aaagctgaag   2040
ctggcgcccg gggagagcaa gacagctacg ttcattttgc ggaggaggga tttgagttat   2100
tgggatacgg gcagccagaa ttgggtggtg cctagtggca gctttggggt ggtagtgggt   2160
gctagttcga gggatttgag gttgaatggg aagtttgatg tttattga              2208
```

<210> SEQ ID NO 5
<211> LENGTH: 849
<212> TYPE: PRT
<213> ORGANISM: Neurospora crassa

<400> SEQUENCE: 5

```
Met Asn His Leu Ser Ser Leu Tyr Glu Gln Leu Leu Arg Leu Pro Thr
1               5                   10                  15

Ser Leu Pro Gly Pro Gly Tyr Phe Ala Asn Gln Ala Lys Glu Val Val
            20                  25                  30

Phe Ser Met Lys Gly Ala Val Ala Leu Ile Cys Thr Ala Val Ser Leu
        35                  40                  45

Gln Ser Cys Ser Ser Leu Pro Ser Ser Ser Ser Ser Ser Ser Thr
    50                  55                  60

Ser Ser Ser Gln His His Asp Gly Gln His Pro Ser Glu Leu Pro Tyr
65                  70                  75                  80

Tyr Gly Leu Ser Pro Pro Phe Tyr Pro Thr Pro Val Ala Asn Gly Thr
                85                  90                  95

Ser Ser Ser Arg Trp Ser Ser Ala Tyr Gln His Ala Leu Ala Leu Thr
            100                 105                 110

Ser Gln Met Thr Leu Leu Glu Leu Gln Asn Leu Thr Arg Gly Phe Pro
        115                 120                 125
```

-continued

```
Gly Pro Cys Val Gly Asn Thr Gly Ser Ile Asp Arg Leu Ser Ile Pro
    130                 135                 140

Pro Leu Cys Phe Tyr Asp Gly Pro Ser Gly Val Arg Gly Gln Glu Phe
145                 150                 155                 160

Ala Ser Ala Phe Pro Ala Gly Ile His Leu Ala Ala Thr Trp Asp Ala
                165                 170                 175

Asp Leu Met Tyr Arg Tyr Gly Arg Ala Val Gly Ala Glu Tyr Arg Gly
            180                 185                 190

Lys Gly Val Asn Ile Ala Leu Gly Pro Leu Ala Gly Pro Leu Gly Arg
        195                 200                 205

Val Ala Lys Gly Gly Arg Asn Trp Glu Gly Leu Gly Ser Asp Pro Tyr
210                 215                 220

Leu Ala Gly Val Gly Met Gly Arg Ile Val Glu Gly Val Gln Gly Glu
225                 230                 235                 240

Gly Val Ile Ala Thr Ala Lys His Phe Leu Leu Asn Glu Gln Glu Tyr
                245                 250                 255

Arg Arg Arg Trp Gly Gln Asp Ala Pro Asp Gly Glu Gly His Ala Ile
            260                 265                 270

Ser Ala Asn Val Gly Asp Arg Ala Leu Arg Glu Tyr Val Trp Pro Phe
        275                 280                 285

Met Asp Ala Leu Arg Ala Gly Ala Gly Ala Val Met Cys Gly Tyr Asn
    290                 295                 300

Arg Ala Asn His Ser Tyr Val Cys Gln Asn Ser Lys Leu Leu Asn Gly
305                 310                 315                 320

Ile Leu Lys Thr Glu Leu Gly Phe Glu Gly Phe Val Val Thr Asp Trp
                325                 330                 335

Asp Ala Gln Met Ser Gly Val Ala Ser Ala Asn Ala Gly Ala Asp Met
            340                 345                 350

Val Met Pro Arg Asp Gly Phe Trp Gly Glu Lys Leu Ile Glu Ala Val
        355                 360                 365

Lys Asn Gly Ser Val Ala Glu Glu Arg Leu Asn Asp Met Ala Thr Arg
370                 375                 380

Val Leu Ala Ala Trp Leu Tyr Ala Gly Gln Asp Asp Gly Thr Tyr Pro
385                 390                 395                 400

Pro Val Gly Val Ala Pro Gly Gly Glu Leu Pro Gly Pro Val Asp Val
                405                 410                 415

Gln Ala Asp His Ala Asp Leu Ile Arg Glu Ile Gly Ala Ala Gly Thr
            420                 425                 430

Val Leu Val Lys Asn Ile Asn Gly Thr Leu Pro Leu Thr Arg Pro Lys
        435                 440                 445

Phe Leu Cys Val Tyr Gly Tyr Asp Ala Ile Val Lys Ser Thr Pro Trp
450                 455                 460

Glu Asn Pro Asp Arg Tyr Gly Gly Gly Tyr Asp Val Asn Arg Gly Trp
465                 470                 475                 480

Thr Thr Phe Asn Gly Thr Leu Ile Thr Gly Gly Ser Gly Ser Gly Ser
                485                 490                 495

Thr Pro Pro Tyr Val Val Ser Pro Phe Glu Ala Leu Ser His Arg Ile
            500                 505                 510

Arg Lys Asp Arg Gly Met Leu Arg Trp Asp Phe His Ser Ala Asn Pro
        515                 520                 525

Ser Gln Gln Tyr Leu Asn Ala Asp Ala Cys Leu Val Phe Ile Asn Ala
530                 535                 540

Tyr Ala Ser Glu Met Ser Asp Arg Pro Ala Leu Ser Asp Thr Phe Ser
```

```
                545                 550                 555                 560
Asp Asp Leu Val Leu Asn Ile Ala Ser Trp Cys Ser Gln Thr Ile Val
                    565                 570                 575
Ile Val His Ser Ala Gly Ile Arg Leu Val Asp Pro Trp Ile Ser His
                580                 585                 590
Pro Asn Val Thr Ala Val Leu Met Ala Gly Leu Pro Gly Gln Glu Ser
                595                 600                 605
Gly Asn Ser Leu Val Asp Ile Leu Tyr Gly Asp Val Asn Pro Ser Gly
            610                 615                 620
Arg Leu Pro Tyr Thr Ile Ala Lys Lys Glu Ser Asp Tyr Gly His Leu
625                 630                 635                 640
Leu Asn Pro Ser Thr Gly Gln Glu Glu Glu Gly Asp Pro Phe Phe
                645                 650                 655
Pro Glu Asp Asn Phe Val Glu Gly Leu His Ile Asp Tyr Arg Phe Phe
                660                 665                 670
Asp Arg His Gly Ile Ala Pro Arg Phe Glu Phe Gly Phe Gly Leu Ser
                675                 680                 685
Tyr Thr Thr Phe Ser Tyr Ser Asp Leu Gln Ile Tyr Val Ser Ile Ala
                690                 695                 700
Pro Gly Val Val Gln Glu Thr Thr Met Pro Ser Leu Ala Ala Thr Thr
705                 710                 715                 720
Arg Phe Ala Glu Phe Pro Asp Pro Asp Thr Pro Val Ile Gln Gly Gly
                    725                 730                 735
His Pro Asp Leu Trp Glu Thr Leu Phe Val Val Arg Cys Arg Val Glu
                740                 745                 750
Asn Ser Gly Gly Lys Tyr Glu Gly Arg Glu Val Val Gln Leu Tyr Val
            755                 760                 765
Gly Ile Pro Ala Leu Asn Gly Gly Glu Asp Lys Glu Thr Pro Val
                770                 775                 780
Arg Gln Leu Arg Gly Phe Lys Arg Val Gly Pro Leu Ala Pro Gly Glu
785                 790                 795                 800
Asp Gly Glu Ala Glu Phe Glu Leu Thr Arg Arg Asp Leu Ser Val Trp
                    805                 810                 815
Asp Val Glu Met Gln Gln Trp Arg Leu Arg Arg Gly Lys Tyr Lys Ile
                820                 825                 830
Trp Val Gly Ala Ser Ser Arg Asp Leu Arg Leu Ser Gly Thr Phe Asp
            835                 840                 845
Ile

<210> SEQ ID NO 6
<211> LENGTH: 2550
<212> TYPE: DNA
<213> ORGANISM: Neurospora crassa

<400> SEQUENCE: 6
atgaaccatc tcagcagtct ctacgagcaa ctgctacggc tgccaacgag cctcccaggc      60
ccaggctact tgccaaccaa gccaaagaa gtcgtcttct ccatgaaggg cgccgtagcc     120
ctcatctgca ccgccgtctc tctgcaatca tgcagtagtc taccatcatc atcatcatca     180
tcatcatcaa catcgtcctc acaacatcat gacgggcaac accctctga actcccctac      240 tacggtctca gtccgccgtt ttaccccacc ccgtcgcca acggcacctc ctcctctcgc      300
tggtcatccg cctaccagca cgccctcgct ctcacctcgc aaatgacgct cttggaactc      360
caaaacctca ctcgcggttt tcctggtcct tgcgtgggaa acacgggctc aatcgaccgc      420
```

```
ctatccatac caccgctctg cttctacgat ggcccctccg gtgtgcgcgg ccaggaattc      480
gcctccgctt ttcccgcggg cattcacctc gccgcgacat gggacgcgga cctcatgtac      540
cgctacggcc gggctgtggg cgctgagtat cgcggtaaag gtgtgaacat tgctctaggg      600
ccgctggccg ggccgttggg acgggtggca aagggaggga ggaattggga aggcttgggg      660
agtgatccgt acctggctgg tgttgggatg ggaggatcg tggagggcgt gcaaggggag       720
ggggtcattg ccactgcgaa gcatttcttg ctcaacgaac aggagtatag cgaagatgg       780 ggacaggatg cgccagacgg agaaggacat gccatcagcg cgaatgttgg ggacagagcg      840
ctgagggagt acgtctggcc gtttatggac gcactgcgcg cgggtgccgg agccgtgatg      900
tgtggatata ataggcgaa tcacagctat gtgtgccaga attccaagtt attgaatgga       960
atactcaaga cggagctagg gtttgaagga tttgtggtta ctgattggga tgcgcagatg      1020
agcggggtcg cgtcagccaa cgccggagcg gatatggtga tgccacggga cgggttctgg      1080
ggcgagaagt tgattgaagc tgtaaagaac ggatctgtgg ccgaggagcg cttgaacgac      1140
atggcgaccc gcgtgctggc ggcatggcta tacgcaggcc aggacgatgg gacctaccca      1200
cccgttggtg tcgcgccggg cggtgagctg cccggcccgg ttgacgtaca agcggaccac      1260
gcggatctca tccgcgaaat cggagcggcg ggcacagtcc tggtcaagaa tatcaacggc      1320
accctccccc taacccgacc caaattcctc tgcgtttacg gctacgacgc catcgtcaaa      1380
tccactccct gggagaaccc cgaccgctac ggcggcggct acgacgtcaa ccgcggctgg      1440
accaccttca acggcacctt gatcaccggc ggcggctccg gcagctccac gcccccttac      1500
gtcgtttccc ccttcgaagc cttgtcccac cgtatccgca agaccgcgg catgctccgc       1560 tgggacttcc actcggccaa cccctcccag caatacctca cgcggacgc ctgcctcgtc        1620 ttcatcaacg cctacgcctc cgagatgtcc gaccgtcctg ccctctccga caccttcagc      1680
gacgacctcg tgctcaatat agcctcctgg tgctcccaaa ccatcgtcat cgtcccactcg     1740 gccggcatcc ggctcgtcga cccgtggatc tcccacccca acgtcaccgc cgtgctcatg      1800
gccggcttac ccggccaaga atccggtaac agtctggtcg acatcttata cggcgacgtc      1860 aaccccttccg gccgtttacc ttataccatt gccaaaaaag agtccgatta cgggcatcta     1920
ctcaaccctt ccaccggcca agaagaagag ggcggcgacc cgttttttccc cgaagataac     1980 tttgtggagg gactacacat cgattaccgc ttcttcgacc gtcatggcat cgctcccccgc    2040 ttcgaattcg gcttcggttt gtcttatacc actttctctt attcggactt gcaaatttac     2100
gtctcaatcg ctcccggtgt cgtgcaagag acgacgatgc cctccctcgc tgccaccacc     2160
cggttcgccg agtttcccga tccggacaca cctgttatcc agggcggaca tccggacttg     2220
tgggagactt tgttcgtggt aaggtgtcgc gtggagaatt ccgggggaa atatgaggga      2280 agagaagttg tgcagttata cgttggtatt cccgctttga atgaggggg agaggataag     2340 gaaacgccgg ttcgtcagct gcgcgggttt aaacgcgtgg gaccgctggc gccgggggag    2400 gatgggagg cggagtttga gttgacgaga agggatttga gcgtttggga tgtggagatg      2460
cagcagtggc ggttgaggag agggaagtat aagatttggg tgggggctag tagtagggat     2520
ttgaggttga gtgggacatt tgatatttga                                      2550

<210> SEQ ID NO 7
<211> LENGTH: 871
<212> TYPE: PRT
<213> ORGANISM: Neurospora crassa
```

<400> SEQUENCE: 7

```
Met Thr Ser Leu Ser Ser Ile Ala Val Gly Gly Pro Phe Glu Arg
1               5                   10                  15

Asp Thr Asp Pro Asn Pro Ser Pro Ser Ser Ile Asp Ser Asn Thr
            20                  25                  30

Thr Pro Asp Thr Asp Phe Thr Pro Met Gly Ser Pro Phe Gln Glu Val
        35                  40                  45

Ala Val Pro Lys Asn Lys Arg Phe Leu Ala Lys Lys Leu Ala Asn
    50                  55                  60

Leu Thr Gln Glu Glu Lys Ile Ser Leu Leu Thr Ala Ala Asp Phe Trp
65                  70                  75                  80

Arg Thr Lys Ser Ile Pro Glu Lys Gly Ile Pro Ala Val Lys Thr Ser
                85                  90                  95

Asp Gly Pro Asn Gly Ala Arg Gly Gly Ile Phe Val Gly Gly Thr Lys
            100                 105                 110

Ala Ala Leu Phe Pro Cys Gly Ile Ser Leu Ala Ala Thr Trp Asn Lys
        115                 120                 125

Ala Leu Leu Arg Glu Val Gly Arg His Leu Ala Glu Glu Ala Lys Ala
    130                 135                 140

Arg Gln Ala Asn Ile Leu Leu Ala Pro Thr Val Cys Met His Arg His
145                 150                 155                 160

Pro Leu Gly Gly Arg Asn Phe Glu Ser Phe Ser Glu Asp Pro Leu Leu
                165                 170                 175

Thr Gly Lys Leu Ala Ala Gln Tyr Ile Lys Gly Leu Gln Glu Arg Gly
            180                 185                 190

Val Ala Ala Thr Ile Lys His Phe Val Gly Asn Glu Gln Glu Thr His
        195                 200                 205

Arg Leu Thr Val Asn Ser Val Ile Ala Glu Arg Pro Leu Arg Glu Ile
    210                 215                 220

Tyr Leu Arg Pro Phe Glu Ile Ala Val Arg Glu Ala Lys Pro Trp Ala
225                 230                 235                 240

Val Met Ser Ser Tyr Asn Leu Glu Val Leu Arg Asp Glu Trp Lys Phe
                245                 250                 255

Asp Gly Ala Val Met Ser Asp Trp Gly Val Asn Ser Thr Ala Glu
            260                 265                 270

Ser Ile Lys Ala Gly Cys Asp Ile Glu Phe Pro His Ser Lys Lys Trp
        275                 280                 285

Arg Tyr Glu Lys Val Met Glu Ala Leu Asn Lys Gly Glu Leu Ser Gln
    290                 295                 300

Ala Asp Ile Asp Arg Ala Ala Glu Asn Val Leu Thr Leu Val Glu Arg
305                 310                 315                 320

Thr Lys Gly Ser Asp Leu Thr Pro Glu Ala Ala Glu Arg Glu Asp Asp
                325                 330                 335

Arg Glu Glu Thr Arg Glu Leu Ile Arg Glu Ala Gly Ile Gln Gly Leu
            340                 345                 350

Thr Leu Leu Lys Asn Glu Gly Ser Ile Leu Pro Ile Asn Pro Lys Thr
        355                 360                 365

Thr Lys Val Ala Val Ile Gly Pro Asn Ala Asn Arg Ala Ile Ala Gly
    370                 375                 380

Gly Gly Gly Ser Ala Ser Leu Asn Pro Tyr Tyr Thr Thr Leu Pro Leu
385                 390                 395                 400

Asp Ser Ile Arg Lys Val Ala Glu Lys Pro Val Thr Tyr Ala Gln Gly
                405                 410                 415
```

```
Cys His Ile Tyr Lys Trp Leu Pro Val Ala Ser Pro Tyr Cys Ser Asp
            420                 425                 430

Lys Thr Gly Lys Pro Gly Val Thr Ile Glu Trp Phe Lys Gly Asp Lys
            435                 440                 445

Phe Lys Gly Glu Pro Val Val Ile Gln Arg Arg Thr Asn Thr Asp Leu
450                 455                 460

Phe Leu Trp Asp Ser Ala Pro Leu Ala Gln Thr Gly Pro Glu Trp Ser
465                 470                 475                 480

Ala Ile Ala Thr Thr Tyr Leu Thr Pro Lys His Ser Gly Lys His Thr
                485                 490                 495

Ile Ser Tyr Met Ser Val Gly Pro Gly Lys Leu Tyr Ile Asn Gly Lys
            500                 505                 510

Leu Ser Leu Asp Leu Trp Asp Trp Thr Glu Gly Glu Ala Met Phe
            515                 520                 525

Asp Gly Ser Val Asp Tyr Leu Val Glu Leu Glu Met Val Ala Asn Arg
            530                 535                 540

Pro Val Glu Leu Arg Val Glu Met Thr Asn Glu Leu Arg Pro Leu Ser
545                 550                 555                 560

Lys Gln Lys Gln Met Gly Met Thr His Arg Tyr Gly Gly Cys Arg Ile
                565                 570                 575

Gly Tyr Lys Glu Ala Asp Gln Ile Asp Tyr Leu Gln Gln Ala Ile Ala
            580                 585                 590

Ala Ala Ser Ser Ala Asp Val Ala Ile Val Val Gly Leu Asp Ala
            595                 600                 605

Glu Trp Glu Ser Glu Gly Tyr Asp Arg Gln Thr Met Asp Leu Pro Tyr
610                 615                 620

Asn Gly Ser Gln Asp Arg Leu Ile Glu Ala Val Val Ala Ala Asn Pro
625                 630                 635                 640

Asn Thr Val Val Val Asn Gln Ser Gly Ser Pro Val Thr Met Pro Trp
                645                 650                 655

Ala Asp Arg Val Pro Ala Ile Leu Gln Ala Trp Tyr Gln Gly Gln Glu
            660                 665                 670

Ala Gly Asn Ala Leu Ala Asp Val Leu Phe Gly Leu Arg Asn Pro Ser
            675                 680                 685

Gly Lys Leu Pro Cys Thr Phe Pro Lys Arg Leu Glu Asp Thr Pro Ala
690                 695                 700

Tyr His Asn Trp Pro Gly Glu Asn Leu Glu Val Ile Tyr Gly Glu Gly
705                 710                 715                 720

Ile Tyr Ile Gly Tyr Arg His Tyr Asp Arg Thr Lys Ile Ala Pro Leu
                725                 730                 735

Phe Pro Phe Gly His Gly Leu Ser Tyr Thr Lys Phe Glu Tyr Gly Arg
            740                 745                 750

Pro Ser Leu Ser Ser Arg Val Leu Arg Glu Asn Gly Val Ile Glu Leu
            755                 760                 765

Cys Val Ala Ile Ser Asn Val Gly Glu Tyr Asp Gly Ala Glu Thr Val
            770                 775                 780

Gln Val Tyr Val Arg Asp Glu Lys Ser Lys Leu Pro Arg Pro Glu Lys
785                 790                 795                 800

Glu Leu Val Ala Phe Glu Lys Val Ala Leu Glu Arg Gly Glu Thr Lys
                805                 810                 815

His Leu Arg Met Glu Leu Asp Lys Tyr Ala Val Gly Tyr Tyr Asp Thr
            820                 825                 830
```

| Asp | Lys | Lys | Gly | Trp | Val | Ala | Glu | Glu | Gly | Arg | Phe | Val | Val | Leu | Val |
|---|---|---|---|---|---|---|---|---|---|---|---|---|---|---|---|
| | | 835 | | | | | 840 | | | | | 845 | | | |

| Gly | Ser | Ser | Ala | Gly | Asp | Ile | Lys | Tyr | Ser | Val | Pro | Phe | Glu | Val | Lys |
|---|---|---|---|---|---|---|---|---|---|---|---|---|---|---|---|
| 850 | | | | | 855 | | | | | 860 | | | | | |

| Gln | Thr | Phe | Thr | Trp | Val | Phe |
|---|---|---|---|---|---|---|
| 865 | | | | 870 | | |

<210> SEQ ID NO 8
<211> LENGTH: 2616
<212> TYPE: DNA
<213> ORGANISM: Neurospora crassa

<400> SEQUENCE: 8

```
atgacttcac tttcctcgat agccgttggg ggaggcccct tcgagcggga tactgatccc      60
aatccctccc cttccagcag tatcgacagc aacaccacgc ccgataccga cttcacgccc     120
atgggaagcc cgttccagga agtggccgtc cccaagaaca agaggttcct ggcgaagaag     180
aagttggcaa atctgacaca ggaggagaag atttccctcc taactgccgc agacttctgg     240
aggacaaagt ccattccgga agggtattct cctgcagtga aaacaagtga tggacccaat     300
ggcgcccgag gtggtatctt tgttggcggt accaaggccg cattattccc ctgcggcatt     360
tcattggccg ccacatggaa caaggccctc ctccgcgaag taggccgtca tttggccgag     420
gaagcaaagg ctcgtcaggc caacattctc ctcgcaccca cggtctgcat gcacaggcat     480
cccttgggag gaaggaactt tgagtctttc tctgaggatc cgcttcttac aggcaagctt     540
gccgctcagt atatcaaggg tcttcaggag agaggtgtgg ctgccaccat caagcacttt     600
gttggcaatg agcaagagac acacagattg acggtcaact ccgtgattgc cgaaaggcca     660
ctccgtgaga tttacctacg gccatttgag attgccgtgc gcgaggccaa gccgtgggct     720
gtcatgtctt cgtacaacct tgaggttctt cgagatgagt ggaaatttga cggtgctgtc     780
atgtccgatt ggggtggcgt caactctacc gcggagtcca tcaaggccgg ctgtgacatc     840
gaattccccc actccaaaaa atggcgttat gaaaaggtca tggaggccct gaacaagggc     900
gaactctccc aggctgacat tgacagagcg gctgaaaacg tcctgactct tgtcgagcga     960
acaaagggaa gcgatctgac acccgaagct gcggaaagag aagatgacag agaggaaacc    1020
cgggagctga tccgcgaggc tggcatccag ggtctcaccc ttttgaaaaa cgaaggatca    1080
attctgccca tcaatcccaa gaccaccaag gttgccgtca tcggcccaa cgccaaccga    1140
gccatcgctg gaggtggtgg gagtgccagc ttgaaccccct attacaccac cctgcctctt    1200
gatagcatcc gcaaggttgc cgaaaagcct gttacctatg cccaaggctg ccacatctac    1260
aagtggctcc ctgttgcctc tccttactgc tccgacaaga ctggcaagcc cggtgttacc    1320
atagagtggt caagggtga caagttcaag ggagagcccg tagtcatcca cgacggacc    1380
aacaccgatc tcttcctctg ggactctgct ccccctcgccc aaaccggccc cgaatggtcc    1440
gccattgcca ccacctacct caccccccaag cactccggca acacaccat ctcctacatg    1500
tccgtcggcc ccggcaagct ctacatcaac ggcaagctct ccctcgacct ctgggactgg    1560
accgaagaag cgaagccat gttcgacggc tccgtcgact acctcgtcga gctcgaaatg    1620
gtcgccaacc gccccgtcga gctccgcgtc gaaatgacca cgagctccg ccccctttcc    1680
aagcaaaagc aaatgggcat gacccaccgc tacggcggct gccgcatcgg ctacaaggaa    1740
gccgaccaaa tcgactacct ccaacaagcc atcgccgccg cctcctccgc cgacgtggcc    1800
atcgtcatcg tcggcctcga cgccgagtgg gaatccgagg ggtacgatcg ccaaaccatg    1860
```

```
gacctgccct acaacggctc gcaagaccgg ctcatcgaag ccgtcgtggc cgccaaccct   1920
aacaccgtcg tcgtcaacca gtccggttca cccgtcacca tgccctgggc tgatcgcgtc   1980
cctgccatct tgcaagcgtg gtaccaaggc caagaagcag gtaacgccct ggccgacgtg   2040
ctctttgggc tgcgcaaccc cagcggaaaa ctccccctgca cgttccccaa gcgtctcgaa   2100
gatacgccgg cgtaccataa ttggccgggc gagaacctcg aggttattta cggcgagggg   2160
atctacattg gctatcgaca ctatgaccgg accaaaatcg cgccgctctt cccctttggt   2220
catggtcttt cgtatacgaa gtttgagtat gggcggccgt cgctgtctag tcgcgtgttg   2280
agggagaatg gagttatcga gctgtgtgtg gcgattagta atgtgggcga gtatgatggg   2340
gcggagacgg tgcaggtgta tgtgcgggat gagaaatcca aactgccgag gccggagaag   2400
gagctggtgg cgtttgagaa ggtggcgctg gaaaggggggg agacgaagca tttgaggatg   2460
gaactggata agtatgcggt ggggtattat gatacagaca aaaagggtg gtggcggag    2520 gaagggaggt ttgtggtttt ggtggggagt tcggcggggg atatcaagta ctctgtgcca   2580
tttgaggtta agcagacttt cacttgggtc ttttag                             2616
```

<210> SEQ ID NO 9
<211> LENGTH: 875
<212> TYPE: PRT
<213> ORGANISM: Neurospora crassa

<400> SEQUENCE: 9

Met Lys Phe Ala Ile Pro Leu Ala Leu Leu Ala Ser Gly Asn Leu Ala
1               5                   10                  15

Leu Ala Ala Pro Glu Pro Ile His Pro Ser His Gln Gln Leu Asn Lys
            20                  25                  30

Arg Ser Leu Ala Tyr Ser Glu Pro His Tyr Pro Ser Pro Trp Met Asp
        35                  40                  45

Pro Lys Ala Ile Gly Trp Glu Glu Ala Tyr Glu Lys Ala Lys Ala Phe
    50                  55                  60

Val Ser Gln Leu Thr Leu Leu Glu Lys Val Asn Leu Thr Thr Gly Ile
65                  70                  75                  80

Gly Trp Gly Ala Glu Gln Cys Val Gly Gln Thr Gly Ala Ile Pro Arg
                85                  90                  95

Leu Gly Leu Lys Ser Met Cys Met Gln Asp Ala Pro Leu Ala Ile Arg
            100                 105                 110

Gly Thr Asp Tyr Asn Ser Val Phe Pro Ala Gly Val Thr Thr Ala Ala
        115                 120                 125

Thr Phe Asp Arg Gly Leu Met Tyr Lys Arg Gly Tyr Ala Leu Gly Gln
    130                 135                 140

Glu Ala Lys Gly Lys Gly Val Thr Val Leu Leu Gly Pro Val Ala Gly
145                 150                 155                 160

Pro Leu Gly Arg Ala Pro Glu Gly Gly Arg Asn Trp Glu Gly Phe Ser
                165                 170                 175

Thr Asp Pro Val Leu Thr Gly Ile Ala Met Ala Glu Thr Ile Lys Gly
            180                 185                 190

Thr Gln Asp Ala Gly Val Val Ala Cys Ala Lys His Phe Ile Gly Asn
        195                 200                 205

Glu Gln Glu His Phe Arg Gln Val Gly Glu Ser Gln Asp Tyr Gly Tyr
    210                 215                 220

Asn Ile Ser Glu Thr Leu Ser Ser Asn Ile Asp Asp Lys Thr Met His
225                 230                 235                 240

```
Glu Met Tyr Leu Trp Pro Phe Val Asp Ala Ile Arg Ala Gly Val Gly
            245                 250                 255

Ser Phe Met Cys Ala Tyr Thr Gln Ala Asn Asn Ser Tyr Ser Cys Gln
        260                 265                 270

Asn Ser Lys Leu Leu Asn Asn Leu Leu Lys Gln Glu Asn Gly Phe Gln
        275                 280                 285

Gly Phe Val Met Ser Asp Trp Gln Ala His His Ser Gly Val Ala Ser
        290                 295                 300

Ala Ala Ala Gly Leu Asp Met Ser Met Pro Gly Asp Thr Met Phe Asn
305                 310                 315                 320

Ser Gly Arg Ser Tyr Trp Gly Thr Asn Leu Thr Leu Ala Val Leu Asn
                325                 330                 335

Gly Thr Val Pro Gln Trp Arg Ile Asp Asp Met Ala Met Arg Ile Met
                340                 345                 350

Ala Ala Phe Phe Lys Val Gly Gln Thr Val Glu Asp Gln Glu Pro Ile
            355                 360                 365

Asn Phe Ser Phe Trp Thr Leu Asp Thr Tyr Gly Pro Leu His Trp Ala
    370                 375                 380

Ala Arg Lys Asp Tyr Gln Gln Ile Asn Trp His Val Asn Val Gln Gly
385                 390                 395                 400

Asp His Gly Ser Leu Ile Arg Glu Ile Ala Ala Arg Gly Thr Val Leu
                405                 410                 415

Leu Lys Asn Thr Gly Ser Leu Pro Leu Lys Lys Pro Lys Phe Leu Ala
            420                 425                 430

Val Ile Gly Glu Asp Ala Gly Pro Asn Pro Leu Gly Pro Asn Gly Cys
        435                 440                 445

Ala Asp Asn Arg Cys Asn Asn Gly Thr Leu Gly Ile Gly Trp Gly Ser
450                 455                 460

Gly Thr Gly Asn Phe Pro Tyr Leu Val Thr Pro Asp Gln Ala Leu Gln
465                 470                 475                 480

Ala Arg Ala Val Gln Asp Gly Ser Arg Tyr Glu Ser Val Leu Arg Asn
                485                 490                 495

His Ala Pro Thr Glu Ile Lys Ala Leu Val Ser Gln Gln Asp Ala Thr
                500                 505                 510

Ala Ile Val Phe Val Asn Ala Asn Ser Gly Glu Gly Phe Ile Glu Ile
            515                 520                 525

Asp Gly Asn Lys Gly Asp Arg Leu Asn Leu Thr Leu Trp Asn Glu Gly
    530                 535                 540

Asp Ala Leu Val Lys Asn Val Ser Ser Trp Cys Asn Asn Thr Ile Val
545                 550                 555                 560

Val Leu His Thr Pro Gly Pro Val Leu Leu Thr Glu Trp Tyr Asp Asn
                565                 570                 575

Pro Asn Ile Thr Ala Ile Leu Trp Ala Gly Met Pro Gly Gln Glu Ser
                580                 585                 590

Gly Asn Ser Ile Thr Asp Val Leu Tyr Gly Arg Val Asn Pro Ser Gly
            595                 600                 605

Arg Thr Pro Phe Thr Trp Gly Ala Thr Arg Glu Ser Tyr Gly Thr Asp
    610                 615                 620

Val Leu Tyr Glu Pro Asn Gly Asn Glu Ala Pro Gln Leu Asp Tyr
625                 630                 635                 640

Thr Glu Gly Val Phe Ile Asp Tyr Arg His Phe Asp Lys Ala Asn Ala
                645                 650                 655

Ser Val Leu Tyr Glu Phe Gly Phe Gly Leu Ser Tyr Thr Thr Phe Glu
```

```
                   660             665             670
Tyr Ser Asn Leu Lys Ile Glu Lys His Gln Val Gly Glu Tyr Thr Pro
            675                 680                 685

Thr Thr Gly Gln Thr Glu Ala Ala Pro Thr Phe Gly Asn Phe Ser Glu
        690                 695                 700

Ser Val Glu Asp Tyr Val Phe Pro Ala Ala Glu Phe Pro Tyr Val Tyr
705                 710                 715                 720

Gln Phe Ile Tyr Pro Tyr Leu Asn Ser Thr Asp Met Ser Ala Ser Ser
                725                 730                 735

Gly Asp Ala Gln Tyr Gly Gln Thr Ala Glu Glu Phe Leu Pro Pro Lys
            740                 745                 750

Ala Asn Asp Gly Ser Ala Gln Pro Leu Leu Arg Ser Ser Gly Leu His
        755                 760                 765

His Pro Gly Gly Asn Pro Ala Leu Tyr Asp Ile Met Tyr Thr Val Thr
    770                 775                 780

Ala Asp Ile Thr Asn Thr Gly Lys Val Ala Gly Asp Glu Val Pro Gln
785                 790                 795                 800

Leu Tyr Val Ser Leu Gly Gly Pro Glu Asp Pro Lys Val Val Leu Arg
                805                 810                 815

Gly Phe Asp Arg Leu Arg Val Glu Pro Gly Glu Lys Val Gln Phe Lys
            820                 825                 830

Ala Val Leu Thr Arg Arg Asp Val Ser Ser Trp Asp Thr Val Lys Gln
        835                 840                 845

Asp Trp Val Ile Thr Glu Tyr Ala Lys Lys Val Tyr Val Gly Pro Ser
    850                 855                 860

Ser Arg Lys Leu Asp Leu Glu Glu Val Leu Pro
865                 870                 875

<210> SEQ ID NO 10
<211> LENGTH: 2628
<212> TYPE: DNA
<213> ORGANISM: Neurospora crassa

<400> SEQUENCE: 10
atgaagttcg ccattccgct tgccttgctg gcgagcggca atctcgccct ggctgcgccc      60
gagccgatcc atccttctca tcaacagctc aataagaggt cgcttgccta ctcagaaccc     120
cattatccat caccatggat ggaccccaag gccatcggct gggaagaagc ctacgaaaag     180
gcaaaggcct ttgtgtccca gttgaccctg ctcgaaaaag tcaaccttac aaccggcatc     240
ggctggggcg ctgaacaatg cgttggccaa acaggtgcca tccctcggct tggcttgaag     300
agcatgtgta tgcaagatgc ccccttggcc atccgtggca ccgactacaa ctcagtcttc     360
cccgccgggg tcacaaccgc cgctacgttt gatcgaggtc tcatgtataa cgcggatat      420 gctttaggcc aggaagccaa gggcaaggga gtcacggttc ctctcggacc tgttgccggt     480
cccctcggcc gggcacccga aggcggccgc aactgggaag cttctcgac cgaccctgtt      540 ctcaccggta tcgccatggc ggagaccatc aagggaacac aggacgctgg cgtcgtcgct     600
tgcgccaagc actttatcgg caacgagcaa gaacacttca gacaggttgg agagtcacag     660
gactacggat acaacatctc cgaaacgcta tcctccaaca ttgacgacaa gaccatgcac     720
gaaatgtatt tgtggccgtt tgttgatgcc atcagagctg gtgtaggctc cttcatgtgc     780
gcctacactc aggccaacaa ctcgtacagc tgccagaact cgaagctcct caacaacctg     840
ctcaagcaag aaaacggatt ccagggcttt gtgatgagcg attggcaagc ccatcactct     900
```

```
ggtgtcgcga gcgctgctgc cggtctcgac atgagcatgc ccggtgatac tatgtttaac      960
agcggccgca gctactgggg aaccaacctc acactcgccg tcctcaatgg aactgtcccg     1020
cagtggcgca ttgacgacat ggccatgcgc atcatggctg ctttcttcaa ggttggccaa     1080
accgtcgagg accaagagcc catcaacttc tccttctgga ccctcgacac gtacggcccg     1140
ctgcactggg ccgctcgcaa agattatcag cagatcaact ggcatgttaa cgttcagggc     1200
gatcacggaa gccttattag ggagattgca gctcgcggaa cagttctgtt gaaaaacacc     1260
ggctcccttc ccctgaaaaa gcccaagttt ctggccgtca ttggtgagga tgctgggccg     1320
aaccctcttg gccgaacgg atgcgccgac aatagatgta acaatggtac cttgggtatt      1380
ggctggggtt ccggcaccgg taacttccct tatcttgtga cgcccgacca gccctgcaa      1440
gcccgcgctg ttcaggatgg atctcgctac gagagtgtct tgaggaacca tgcgcccacg     1500
gaaatcaagg ccctggtttc ccagcaggac gcaactgcca ttgtctttgt caacgccaac     1560
tctggtgaag gcttcatcga gattgatggc aacaaaggtg atcggctgaa cctcacccttt    1620
tggaatgagg gcgatgctct ggtcaagaat gtttccagct ggtgtaacaa caccattgtc     1680
gtcctccaca cacctggtcc cgttttgctc acggaatggt acgacaaccc caatattacc     1740
gccattctct gggccggtat gcccggtcag gagagcggca actccatcac ggacgtcttg     1800
tacggtagag tcaacccatc tgggcgcact cccttcacct ggggtgccac gcgcgaaagc     1860
tacggcaccg atgttctcta tgagccgaac aacgggaacg aagctcctca gctggactac     1920
accgaaggag tctttatcga ttaccgtcac tttgacaagg ccaacgcctc ggtcctttac     1980
gagtttggct ttggattgag ctataccacc tttgagtaca gcaacttgaa gatcgagaag     2040
caccaagtcg gcgagtacac tcccaccaca gggcagacgg aagctgcgcc cacttttgga     2100
aacttttctg aaagcgtgga agactacgta ttccctgccg cagagttccc ctacgtctac     2160
cagtttatt accctacct caacagcacc gacatgtctg cttccagcgg cgatgcgcag      2220
tacggccaga ctgccgagga gttcttgccg cccaaggcca acgatggatc ggcgcagcct     2280
ttgcttcgct catccggcct tcatcacccc ggtggaaacc ctgctcttta cgacatcatg     2340
tacactgtta cggcggatat caccaacacg ggcaaggtgg cgggtgatga agtaccgcag     2400
ctgtacgtga gcctcggtgg gccagaggat cccaaggtgg tgctgagagg gtttgacaga     2460
cttagggttg agcctgggga aaggtgcag ttcaaggcgg tgctgacgag gagggatgtg      2520
agttcatggg atacggtgaa gcaggattgg gtgattactg agtacgcgaa gaaggtgtac     2580
gtcgggccaa gctcgaggaa gttggatctc gaggaggttc ttccctga                2628
```

<210> SEQ ID NO 11
<211> LENGTH: 827
<212> TYPE: PRT
<213> ORGANISM: Neurospora crassa

<400> SEQUENCE: 11

Met Ala Val Arg Ser Asn Phe Val Trp Leu Thr Leu Ala Leu Ser Phe
1               5                   10                  15

Phe Asp Leu Thr Cys Asn Ala Ser Pro Val Arg Gln Arg Ala Ala Val
            20                  25                  30

Pro Asp Gly Phe Tyr Ala Ala Pro Tyr Tyr Thr Pro Tyr Gly Gly
        35                  40                  45

Trp Glu Asp Ser Trp Lys Asp Ser Tyr Ala Lys Ala Gln Ala Leu Val
    50                  55                  60

Gly Lys Met Thr Leu Ala Glu Lys Thr Asn Ile Thr Gly Gly Ser Gly

```
            65                  70                  75                  80
Met Phe Met Gly Pro Cys Val Gly Asn Ser Gly Ser Ala Tyr Arg Val
                        85                  90                  95

Gly Phe Pro Gln Leu Cys Leu Gln Asp Gly Ala Leu Gly Val Gly Asn
                100                 105                 110

Thr Asp His Asn Thr Ala Phe Pro Ala Gly Ile Thr Thr Gly Ala Thr
            115                 120                 125

Phe Asp Lys Asp Leu Ile Tyr Ala Arg Ala Val Ala Ile Gly Lys Glu
        130                 135                 140

Phe Arg Gly Lys Gly Ala His Val Phe Leu Gly Pro Met Val Gly Pro
145                 150                 155                 160

Leu Gly Arg Lys Pro Leu Gly Gly Arg Asn Trp Glu Gly Phe Gly Ala
                165                 170                 175

Asp Pro Val Leu Gln Gly Ile Ala Gly Ala Leu Thr Ile Lys Gly Val
                180                 185                 190

Gln Glu Gln Gly Val Ile Ala Thr Ile Lys His Leu Ile Gly Asn Glu
            195                 200                 205

Gln Glu Met Tyr Arg Met Tyr Asn Pro Phe Gln Ala Gly Tyr Ser Ser
        210                 215                 220

Asn Ile Val Ala Ser Ala Leu Ala Gly Leu Asp Met Ser Met Pro Gly
225                 230                 235                 240

Asp Thr Gln Ile Pro Leu Phe Gly Asn Ser Pro Phe Lys Phe His Leu
                245                 250                 255

Thr Glu Ala Val Leu Asn Gly Ser Val Pro Val Asp Arg Leu Asn Asp
            260                 265                 270

Met Ala Thr Arg Ile Val Ala Ala Trp Tyr Gln Phe Gly Gln Asp Lys
        275                 280                 285

Asn Phe Pro Ala Val Asn Phe His Ser Tyr Val Ser Ser Glu Lys Gly
            290                 295                 300

Leu Leu Tyr Pro Gly Ala Leu Pro Val Ser Pro Ile Gly Lys Val Asn
305                 310                 315                 320

Trp Phe Val Asp Val Gln Ala Asp His Gly Ser Val Ala Arg Gln Val
                325                 330                 335

Ala Gln Asp Ala Ile Thr Leu Leu Lys Asn Asp Asp Asn Phe Leu Pro
            340                 345                 350

Leu Ser Thr Lys Ser Ser Leu Arg Ile Phe Gly Ser Asp Ala Arg Val
        355                 360                 365

Asp Pro Asp Gly Pro Asn Ala Cys Gly Asn Arg Ala Cys Asn Lys Gly
        370                 375                 380

Thr Leu Gly Met Gly Trp Gly Ser Gly Val Ala Asn Tyr Pro Tyr Phe
385                 390                 395                 400

Asp Asp Pro Ile Thr Ala Ile Lys Lys Arg Val Glu Asn Val Lys Leu
                405                 410                 415

Tyr Asp Ser Asp Asp Phe Pro His Thr Leu Thr Pro Ser Pro Thr Asp
                420                 425                 430

Asp Asp Ile Ala Ile Val Phe Ile Asn Ser Ala Ala Gly Glu Asn Ser
            435                 440                 445

Leu Thr Val Glu Gly Asn His Gly Asp Arg Asp Asn Asp Lys Phe Ser
        450                 455                 460

Ala Trp His Asn Gly Asp Asn Leu Val Gln Lys Ala Ala Glu Asn Tyr
465                 470                 475                 480

Lys Asn Val Ile Val Val His Thr Val Gly Pro Leu Ile Leu Glu
                485                 490                 495
```

```
Pro Trp Ile Asp Leu Pro Ser Val Lys Ala Val Leu Phe Ala His Leu
            500                 505                 510

Pro Gly Gln Glu Ala Gly Glu Ser Leu Ala Asn Val Leu Phe Gly Asp
        515                 520                 525

Val Ser Pro Ser Gly His Leu Pro Tyr Ser Ile Thr Lys Lys Glu Asn
    530                 535                 540

Asp Leu Pro Asp Ser Val Thr Lys Leu Val Lys Glu Ile Ile Gly Gln
545                 550                 555                 560

Pro Gln Asp Thr Tyr Ser Glu Gly Leu Tyr Ile Asp Tyr Arg Trp Leu
                565                 570                 575

Asn Lys Gln Gly Ile Lys Pro Arg Tyr Ala Phe Gly His Gly Leu Ser
            580                 585                 590

Tyr Thr Thr Phe Asn Tyr Thr Asp Ala His Ile Lys Ile Val Asn Ala
        595                 600                 605

Leu Ser Ser Ala Leu Pro Pro Ala Arg Gln Pro Lys Pro Ser Val Ala
    610                 615                 620

Ile Leu Ser Thr Glu Ile Pro Pro Ala Ser Asp Ala Tyr Glu Pro Ala
625                 630                 635                 640

Gly Phe Ser Lys Val Trp Arg Tyr Ile Tyr Ser Trp Leu Ser Lys Ser
                645                 650                 655

Asp Ala Asp Lys Ala Tyr Ala Val Gly Thr Ser Ser Ser Lys Ser
            660                 665                 670

Gly Ser Gln Thr Tyr Pro Tyr Pro Glu Gly Tyr Ser Ser Val Gln Lys
        675                 680                 685

Pro Gly Val Pro Ala Gly Gly Gln Gly Gly Asn Pro Ala Leu Phe
    690                 695                 700

Asp Thr Ile Leu Glu Leu Asp Val Thr Val Gln Asn Thr Gly Ser Arg
705                 710                 715                 720

His Lys Gly Lys Ala Ser Val Gln Ala Tyr Ile Gln Phe Pro Thr Asp
                725                 730                 735

Ser Gly Tyr Asp Thr Pro Ile Ile Gln Leu Arg Asp Phe Ala Lys Thr
            740                 745                 750

Lys Glu Leu Gly Thr Gly Glu Ser Glu Thr Val Thr Leu Arg Leu Arg
        755                 760                 765

Arg Lys Asp Leu Ser Val Trp Asp Thr Gln Lys Gln Asn Trp Val Ala
    770                 775                 780

Pro Gly Ala Leu Gly Ala Asn Gly Lys Ser Lys Arg Tyr Ile Val Trp
785                 790                 795                 800

Leu Gly Glu Gly Ser Asp Lys Leu Phe Thr Arg Cys Phe Ser Asp Thr
                805                 810                 815

Leu Val Cys Glu Arg Gly Val Glu Pro Pro Val
            820                 825

<210> SEQ ID NO 12
<211> LENGTH: 2484
<212> TYPE: DNA
<213> ORGANISM: Neurospora crassa

<400> SEQUENCE: 12
atggctgtcc gatcgaactt tgtgtggctc actctcgcct tgagcttttt cgaccttacc      60
tgcaatgcaa gtccagtgcg acaacgagcg gccgtcccag atggtttcta tgcggctcct     120
tactacccaa cgccatacgg tggctgggaa gattcatgga agacagcta tgcaaaggca      180 caggcactgg tgggcaagat gacactagca gagaagacga acatcacggg tggaagtggt     240
```

```
atgtttatgg gcccttgtgt aggaaacagc ggcagtgcat accgagtcgg ctttcctcag    300
ctttgtttgc aggatggtgc tctcggtgtg ggcaacacgg accataacac tgcatttcca    360
gctggtatca ccacgggagc gacgttcgac aaggacctta tctatgctcg cgcagtggct    420
attggtaaag aatttcgcgg caaaggagcc acgttttc ttggtcccat ggtaggtccc      480
ctaggtcgca agccactcgg tggccgcaac tgggaaggct tcggtgccga tcccgttctc    540
caaggtattg ccggtgcctt gactatcaag ggtgtccagg aacagggtgt tattgctact    600
atcaagcatc tcattggaaa cgagcaggag atgtatcgca tgtacaaccc atttcaagca    660
ggatacagtt cgaatattgt cgcatcagca ctggccggcc ttgacatgag catgcctgga    720
gacactcaaa tacctctctt tggtaatagc cccttcaagt tccatctcac ggaggctgtc    780
ttgaacggct ccgtgccagt ggacaggcta acgacatgg caaccaggat gtggccgct      840 tggtatcagt tcggccaaga caagaacttc ccagctgtta actttcactc atacgtatcg    900
agtgagaagg gacttctata tccaggtgct cttccggtct cgcccattgg taaggttaac    960
tggtttgtgg atgttcaagc ggaccacggc tcggtcgcac gccaggtcgc ccaagatgcc   1020
attactcttc tgaagaatga tgataatttc ctgccccttt ctaccaagtc atccctcagg   1080
atcttcggct ctgatgctcg ggttgaccct gatgcccaa atgcttgcgg aaaccgcgcc    1140
tgcaacaagg gcactctggg aatgggctgg ggctccggcg ttgcgaacta ccctatttt    1200 gatgacccca tcactgccat caagaagcgg gtcgaaaatg tcaagctcta cgacagcgat   1260
gacttccccc acacactcac tccctcgccc actgatgacg acattgcaat tgtctttatc   1320
aactccgccg cgggcgaaaa ctcgctcacc gttgaaggca accatggtga tcgcgacaat   1380
gacaagttct ccgcttggca caatggagat aatctcgtcc agaaggccgc ggagaactac   1440
aaaaacgtca tagtcgttgt ccacacagtc ggccccctta tactcgagcc ctggattgac   1500
ctgccctccg tgaaggccgt cctcttcgcc cacctccccg ccaagaagc cggcgagtcg    1560 ctcgccaacg ttctcttcgg cgacgtctca ccctccggcc acctccccta ctccatcacc   1620
aagaaggaga cgacctcccc tgacagtgta accaagctcg tcaaggaaat catcggccag   1680
ccccaagata cctacagtga aggcctctat atcgattacc gctggctcaa taagcaaggc   1740
atcaagcccc gctatgcctt cggccacggt ctgagttaca ccaccttcaa ctacaccgac   1800
gctcacatca agatcgtcaa cgccctctcc tccgccctgc cgcccgctcg ccagcccaag   1860
ccctccgtcg ccatcctctc caccgagata ccgcccgctt cagatgccta tgagcccgcc   1920
ggcttctcca aggtctggcg ctacatttac tcctggctat ccaagtccga cgccgacaag   1980
gcctatgccg tcggtacctc ttcttcttcc aagtccggct cccaaactta cccctacccc   2040
gagggctact cgagcgtcca aaagcctggt gtccctgccg gcgggggaca gggtggtaac   2100
ccggccctct ttgacaccat cctcgagctg gacgtgactg tgcaaaacac tggttctcga   2160
cacaagggta agcctctgt gcaggcgtat atccagtttc ccacggacag cgggtacgac    2220
acgcctatta tccagttgcg tgactttgcc aagacgaagg agttgggcac cggggagagc   2280
gagacggtta cgttaaggct gaggaggaag gatttgagcg tgtgggatac gcaaaagcag   2340
aattgggtgg ctcctggtgc cttggggggct aatgggaaga gtaagcggta cattgtgtgg   2400
ttgggtgagg ggagtgataa gcttttcact aggtgtttca gcgatacttt ggtttgtgaa   2460
aggggggttg agccacctgt ttga                                          2484
```

<210> SEQ ID NO 13

<211> LENGTH: 791
<212> TYPE: PRT
<213> ORGANISM: Neurospora crassa

<400> SEQUENCE: 13

```
Met Thr Arg Lys Met Pro Thr Leu Val Arg Pro Thr His Asn Gly Glu
1               5                   10                  15

Arg Tyr Glu Ile Thr Asn Pro Thr Ala Met Pro Lys Ala Ala Gly Phe
            20                  25                  30

Leu Trp Asn Gln Lys Met Met Ile Gln Ile Thr Cys Arg Gly Phe Ala
        35                  40                  45

Thr Ala Gln Phe Met Gln Pro Glu Pro Ala Lys Tyr Ala Tyr Ala Pro
    50                  55                  60

Asn Ile Glu Ala Lys Thr Phe Met Gln Pro Glu Pro Asn Tyr Tyr Ala
65                  70                  75                  80

His His Pro Gly Arg Phe Val Tyr Ile Lys Asp Glu Thr Gly Arg
                85                  90                  95

Leu Phe Ser Ala Pro Tyr Glu Pro Val Arg Ala Pro His Asp Arg Phe
            100                 105                 110

Val Phe Ser Ala Gly Lys Thr Asp Val Phe Trp Val Ile Glu Ser Met
        115                 120                 125

Gly Ile Arg Val Glu Met Thr Met Gly Leu Pro Thr His His Val Ala
    130                 135                 140

Glu Leu Trp Thr Ile Lys Val Lys Asn Leu Ser Ser Arg Pro Arg Lys
145                 150                 155                 160

Leu Ser Val Thr Pro Tyr Phe Pro Ile Gly Tyr Met Ser Trp Met Asn
                165                 170                 175

Gln Ser Ala Glu Trp Asn His Asn Leu Asn Gly Ile Val Ala Ser Cys
            180                 185                 190

Val Thr Pro Tyr Gln Lys Ala Ala Asp Tyr Phe Lys Asn Lys Tyr Leu
        195                 200                 205

Lys Asp Lys Thr Tyr Phe Leu Cys Asp Val Pro Pro Asp Ser Trp Glu
    210                 215                 220

Ala Ser Gln Gln Ala Phe Glu Gly Glu Gly Gly Leu His Asn Pro Ser
225                 230                 235                 240

Ala Leu Gln Glu Arg Asn Leu Ser Gly Ser Asp Ala Arg Tyr Glu Thr
                245                 250                 255

Pro Thr Ala Ala Val Gln Tyr Lys Ile Ala Leu Gly Thr Gly Glu Gln
            260                 265                 270

Gln Glu Tyr Arg Phe Leu Phe Gly Pro Ala His Asp Glu Ala Glu Ile
        275                 280                 285

Gly Ala Met Arg Ser Lys Tyr Leu Ser Lys Glu Gly Phe Glu Gln Thr
    290                 295                 300

Ala Ala Asp Tyr Ala Ala Tyr Met Ala Arg Gly Arg Gly Cys Leu His
305                 310                 315                 320

Val Glu Thr Pro Asp Lys Asp Leu Asp Asn Phe Ile Asn Asn Trp Leu
                325                 330                 335

Pro Arg Gln Val Tyr Tyr His Gly Asp Val Asn Arg Leu Thr Thr Asp
            340                 345                 350

Pro Gln Thr Arg Asn Tyr Leu Gln Asp Asn Met Gly Met Asn Tyr Ile
        355                 360                 365

Lys Pro Glu Val Ser Arg Arg Ala Phe Leu Thr Ala Ile Ala Gln Gln
    370                 375                 380

Glu Ala Thr Gly Ala Met Pro Asp Gly Ile Leu Leu Val Glu Gly Ala
```

```
        385                 390                 395                 400
Glu Leu Lys Tyr Ile Asn Gln Val Pro His Thr Asp His Cys Val Trp
                405                 410                 415
Leu Pro Val Thr Leu Glu Ala Tyr Leu Asn Glu Thr Gly Asp Tyr Ser
                420                 425                 430
Leu Leu Lys Glu Lys Val Pro Ser Ala Asn Gly Asp Lys Leu Thr Val
                435                 440                 445
Phe Glu Arg Phe Cys Arg Ala Met Asp Trp Leu Leu Lys Ser Arg Asp
            450                 455                 460
His Arg Gly Leu Ser Tyr Ile Ala Gln Gly Asp Trp Cys Asp Pro Met
465                 470                 475                 480
Asn Met Val Gly Tyr Lys Gly Lys Gly Val Ser Gly Trp Leu Thr Leu
                485                 490                 495
Ala Thr Ala Phe Ser Leu Asn Ile Trp Ala Lys Val Cys Asp His Glu
                500                 505                 510
Gly Glu Thr Asp Leu Ala Lys Arg Phe Arg Glu Gly Ala Asp Ala Cys
            515                 520                 525
Asn Ala Ala Ala Asn Glu His Leu Trp Asp Gly Glu Trp Phe Ala Arg
530                 535                 540
Gly Ile Thr Asp Asp Asn Val Val Phe Gly Ile Lys Glu Asp Lys Glu
545                 550                 555                 560
Gly Arg Ile Trp Leu Asn Pro Gln Ser Trp Ser Ile Leu Ser Gly Ala
                565                 570                 575
Ala Ser Pro Glu Gln Ile Asp Lys Met Leu Pro Gln Ile Asp Ser His
            580                 585                 590
Leu Asn Thr Pro Tyr Gly Ile Gln Met Phe Gly Pro Tyr Thr Lys
            595                 600                 605
Met Arg Glu Asp Val Gly Arg Val Thr Gln Lys Ala Ile Gly Ser Ala
            610                 615                 620
Glu Asn Ala Ala Val Tyr Asn His Ala Gly Ile Phe Phe Ile His Ser
625                 630                 635                 640
Leu Tyr Glu Leu Gly Ala Gln Gln Asp Arg Ala Phe Thr Leu Leu Arg
                645                 650                 655
Gln Met Leu Pro Gly Pro Thr Asp Thr Asp Tyr Ile Gln Arg Gly Gln
                660                 665                 670
Leu Pro Ile Tyr Ile Pro Asn Tyr Tyr Arg Gly Ala Trp Lys Glu Cys
                675                 680                 685
Pro Arg Thr Ala Gly Arg Ser Ser Gln Leu Phe Asn Thr Gly Thr Val
            690                 695                 700
Ser Trp Val Tyr Arg Cys Ile Ile Glu Gly Leu Cys Gly Leu Arg Gly
705                 710                 715                 720
Asp Gly Glu Gly Leu Leu Ile Arg Pro Gln Leu Pro Ser Ser Trp Asn
                725                 730                 735
Ser Met Lys Val Thr Arg Glu Phe Arg Gly Ala Thr Phe Asn Val Asp
                740                 745                 750
Ile Arg Arg Gly Asn Val Lys Glu Val Thr Val Arg Asn Gly Asp Lys
                755                 760                 765
Val Leu Pro Ala Pro His Val Lys Asp Ile Glu Pro Gly Gln Thr Tyr
            770                 775                 780
Asn Leu Thr Val Thr Ile Pro
785                 790

<210> SEQ ID NO 14
```

<211> LENGTH: 2376
<212> TYPE: DNA
<213> ORGANISM: Neurospora crassa

<400> SEQUENCE: 14

| | | | | | |
|---|---|---|---|---|---|
| atgaccagga | aaatgccgac | tctggtccgc | ccgacccata | acggcgagcg | ctacgaaatc | 60 |
| accaacccca | cagccatgcc | caaggccgct | ggcttcctgt | ggaaccaaaa | gatgatgatt | 120 |
| cagatcacct | gccgtggttt | tgcgactgcc | cagttcatgc | agcccgagcc | tgcaaagtac | 180 |
| gcctatgcgc | ccaatatcga | ggccaagacc | ttcatgcaac | cggagccgaa | ctactacgcc | 240 |
| caccatcccg | gccgctttgt | gtacatcaag | gatgaggaga | ccggccggct | tttctctgct | 300 |
| ccctacgaac | ccgtccgcgc | cccacacgat | cgcttcgtct | tctccgccgg | caagactgac | 360 |
| gtcttctggg | tcatcgagtc | gatgggaatt | cgcgtggaga | tgaccatggg | cctccccacc | 420 |
| caccatgttg | ccgaactctg | gaccatcaaa | gtcaaaaacc | tttcaagccg | tcctcggaaa | 480 |
| ctcagtgtga | cccccctactt | ccccattgga | tacatgtcgt | ggatgaacca | gtcggccgag | 540 |
| tggaatcata | acctcaacgg | aatcgttgcc | agctgtgtca | ccccttacca | gaaggccgcc | 600 |
| gattacttca | gaacaagta | tctcaaggac | aagacctact | tcctttgtga | tgtccctcct | 660 |
| gactcctggg | aagccagtca | gcaagccttt | gaaggtgagg | tggtcttca | caaccccagt | 720 |
| gccctacaag | agaggaatct | cagcggcagt | gatgcgcggt | acgaaactcc | cacggcagct | 780 |
| gtgcaataca | agattgctct | tggcacgggc | gagcaacaag | agtaccggtt | cctctttggc | 840 |
| cccgcccatg | atgaagctga | gatcggagcc | atgcggtcca | agtacctaag | caaggaaggt | 900 |
| ttcgaacaga | ctgcagctga | ttacgccgct | tacatggccc | gtgggcgcgg | atgtctccac | 960 |
| gtggaaaccc | cagataagga | tctcgacaac | ttcatcaaca | actggctgcc | ccgacaggtc | 1020 |
| tactaccacg | gcgatgtcaa | ccgcttgacc | actgatccac | aaaacacgcaa | ctacctacag | 1080 |
| gacaacatgg | gcatgaacta | catcaaaccc | gaagtatccc | gcagggcttt | cctcacagcc | 1140 |
| attgcccagc | aagaagctac | cggcgccatg | cccgacggca | tccttttggt | tgagggtgcc | 1200 |
| gaactcaaat | acatcaacca | ggtacctcac | actgatcact | gtgtgtggtt | gccagttaca | 1260 |
| ctggaggcat | acctcaacga | gaccggtgat | tacagcttgc | taaaggagaa | agtgccgagt | 1320 |
| gccaacggcg | acaagctcac | cgtcttcgag | cgcttctgcc | gtgctatgga | ctggctgctc | 1380 |
| aagtctcgtg | accatcgtgg | tctgagttat | attgcccagg | gtgactggtg | tgatcccatg | 1440 |
| aacatggtgg | gctacaaggg | caagggtgtt | tctggctggc | tcactctggc | cacggccttt | 1500 |
| tccctcaaca | tttgggccaa | ggtttgcgat | catgaaggcg | agaccgatct | cgccaagcgc | 1560 |
| ttccgtgagg | gtgccgacgc | atgcaacgct | gctgcaaacg | agcatctttg | ggacggtgaa | 1620 |
| tggtttgctc | gcggcatcac | tgacgacaat | gttgtctttg | gcatcaagga | ggacaaggaa | 1680 |
| ggccgcatct | ggttgaaccc | ccagtcctgg | tccatcctca | gcggtgctgc | cagccctgaa | 1740 |
| cagattgaca | agatgttgcc | ccagattgac | tcgcatctca | acaccatta | tggtatccag | 1800 |
| atgttcggtc | ccccttacac | caagatgcgc | gaggatgtcg | gtcgcgtaac | gcaaaaagcc | 1860 |
| attggctcgg | ccgagaacgc | cgctgtgtac | aaccacgctg | gaatcttctt | catccatagc | 1920 |
| ctgtacgagc | ttggagcaca | gcaagaccga | gcatttaccc | tattacggca | aatgctccct | 1980 |
| ggtcctactg | acaccgacta | tatccaacga | ggccagctgc | ccatctatat | tcccaactac | 2040 |
| taccgaggcg | cctggaagga | gtgtcctcgc | acagctggcc | ggtccagtca | gttgtttaac | 2100 |
| acgggtaccc | tttcttgggt | ttaccgctgc | atcattgaag | gctctgtgg | cttgcgcggc | 2160 |
| gatggcgaag | gtctactcat | ccggccacag | ctaccgagct | cctggaacag | catgaaggtc | 2220 |

```
actcgcgagt tcgggcgc caccttcaat gtcgacattc gtcgtggcaa tgtcaaggag    2280
gtcactgtca ggaatggcga caaggtcctg cctgcgcctc acgtcaagga catcgagcca    2340
ggccagacgt acaaccttac agtgactatt ccgtaa                              2376
```

<210> SEQ ID NO 15
<211> LENGTH: 430
<212> TYPE: PRT
<213> ORGANISM: Neurospora crassa

<400> SEQUENCE: 15

```
Met Gln Arg Val Gln Ser Ala Val Asp Phe Ser Asn Leu Leu Asn Pro
 1               5                  10                  15

Ser Glu Ser Thr Ala Glu Lys Arg Asp His Ser Gly Ser Pro Arg Gln
            20                  25                  30

Gln Thr Ala Gln Pro Gln Gln Gln Gln Gln Pro Gln Pro Glu Ala
        35                  40                  45

Asp Met Ala Thr Val Gly Leu Leu Arg Pro Asn Gly Pro Leu Pro Gly
    50                  55                  60

Ala Gln Ala Thr Glu Pro Ala Asn Glu Leu Pro Arg Pro Tyr Lys Cys
65                  70                  75                  80

Pro Leu Cys Asp Lys Ala Phe His Arg Leu Glu His Gln Thr Arg His
                85                  90                  95

Ile Arg Thr His Thr Gly Glu Lys Pro His Ala Cys Gln Phe Pro Gly
            100                 105                 110

Cys Ser Lys Lys Phe Ser Arg Ser Asp Glu Leu Thr Arg His Ser Arg
        115                 120                 125

Ile His Ser Asn Pro Asn Ser Arg Arg Gly Asn Lys Gly Gln Gln Gln
    130                 135                 140

Gln Gln His Pro Leu Val His Asn His Gly Leu Gln Pro Asp Met Met
145                 150                 155                 160

Pro Pro Pro Gly Pro Lys Ala Ile Arg Ser Ala Pro Thr Ala Met
                165                 170                 175

Ser Ser Pro Asn Val Ser Pro Pro His Ser Tyr Ser Pro Tyr Asn Phe
            180                 185                 190

Ala Pro Ser Gly Leu Asn Pro Tyr Ser His Ser Arg Ser Ser Ala Gly
        195                 200                 205

Ser Gln Ser Gly Pro Asp Ile Ser Leu Leu Ala Arg Ala Ala Gly Gln
    210                 215                 220

Val Glu Arg Asp Gly Ala Ala His His His Phe Gln Pro Arg Phe Gln
225                 230                 235                 240

Phe Tyr Gly Asn Thr Leu His Ala Ala Thr Ala Ser Arg Asn Gln Leu
                245                 250                 255

Pro Gly Leu Gln Ala Tyr His Met Ser Arg Ser His Ser His Glu Asp
            260                 265                 270

His Asp Asp His Tyr Gly Gln Ser Tyr Arg His Ala Lys Arg Ser Arg
        275                 280                 285

Pro Asn Ser Pro Asn Ser Thr Ala Pro Ser Ser Pro Thr Phe Ser His
    290                 295                 300

Asp Ser Leu Ser Pro Thr Pro Asp His Thr Pro Leu Ala Thr Pro Ala
305                 310                 315                 320

His Ser Pro Arg Leu Arg Pro His Pro Gly Leu Glu Leu Pro Pro Phe
                325                 330                 335

Arg Asn Leu Ser Leu Gly Gln Gln His Thr Thr Pro Ala Leu Ala Pro
```

```
                340                 345                 350
Leu Glu Pro Ala Leu Asp Gly Gln Phe Ser Leu Pro Gln Thr Pro Pro
            355                 360                 365

Ala Ala Pro Arg Ser Ser Gly Met Ser Leu Thr Asp Ile Ile Ser Arg
        370                 375                 380

Pro Asp Gly Thr Gln Arg Lys Leu Pro Val Pro Lys Val Ala Val Gln
385                 390                 395                 400

Asp Leu Leu Gly Pro Ala Asp Gly Phe Asn Pro Ser Val Arg Asn Ser
                405                 410                 415

Ser Ser Thr Ser Leu Ser Gly Ala Glu Met Met Asp Arg Leu
            420                 425                 430

<210> SEQ ID NO 16
<211> LENGTH: 1293
<212> TYPE: DNA
<213> ORGANISM: Neurospora crassa

<400> SEQUENCE: 16
atgcaacgcg tacagtcagc agtagatttc tccaatctgc tgaatccatc cgaatccacg      60
gccgagaaga gagatcacag cggctcccca agacaacaaa ccgcacaacc acaacagcag     120
cagcaacaac cacagcccga agcagacatg gcgacagtcg gcttgttgcg ccccaacggg     180
cccctgcccg tgcccaagcc tactgagccc gccaacgagc tcccacgccc ttacaagtgc     240
cctctgtgcg acaaggcttt ccaccgcctg gagcatcaga caagacacat tcgcacccac     300
acaggagaga gccgcacgc gtgccagttc cggggtgta gcaagaagtt ctcgcgttcg       360
gacgagctga ctcggcactc gaggatacac agcaatccta actcgcggag gggaaacaag     420
ggccagcagc agcagcagca tccccttgtc cacaaccacg ggctgcagcc cgacatgatg     480
cctcctcctg gccccaaggc tatccgctct gctccgccta ctgccatgtc ctctcccaac     540
gtgtcacccc ctcactctta cagcccttat aactttgctc cctcgggcct caaccccat     600 agccattccc gtagctccgc gggaagccaa agtggtcctg atatctcgct cctcgcgagg     660
gccgccggac aagttgagcg ggacggcgcc gctcatcatc actttcagcc acgattccag     720
ttctacggaa acactctgca tgccgccacg gcttccagga atcagctccc tgggctccag     780
gcctatcaca tgtccaggtc gcactcccac gaggatcacg atgaccacta tggccagtct     840
tacaggcatg ccaagaggtc gaggcccaac tcgcccaact cgacagcacc ttcttccccg     900
acattctctc acgactcgct atcgcctact cccgatcaca ctccacttgc tactcctgct     960
cactcgcctc gtctgcgccc tcatcctggc cttgagctgc cccctttcag gaacctttcc    1020
ttgggccaac agcacacaac gcctgcgctg gctcctctcg agcccgctct tgatgggcag    1080
ttctctcttc cccagactcc tcccgctgcg cccaggagca gtggcatgtc cttgaccgac    1140
atcatcagcc gacctgatgg cactcaaagg aaacttcctg tgcccaaggt tgctgtccag    1200
gatctgcttg accagccga tgggttcaac ccaagtgtca ggaactcttc ttctaccagc     1260
ctctctggag cggagatgat ggaccggttg taa                                 1293

<210> SEQ ID NO 17
<211> LENGTH: 714
<212> TYPE: PRT
<213> ORGANISM: Neurospora crassa

<400> SEQUENCE: 17

Met Ser Asn Pro Arg Arg Arg Pro Ala Gly Gly Leu Thr Leu Lys Thr
1               5                   10                  15
```

```
Asn Met Leu Leu Gln Lys Gly Ala Thr Phe His Ser Pro Thr Thr Pro
         20                  25                  30

Ala Ser Gly Asp Ser Ser Glu Arg Val Phe Val Pro Pro Ser Leu Pro
             35                  40                  45

Arg Arg Ser His Thr Asn Leu Asp Asp Val Ile Asp Ser Arg Cys Arg
 50                  55                  60

Arg Val Ala Leu Ala Leu Asp Ala Ile Glu Arg Gln Leu Ala Ser Ser
 65                  70                  75                  80

Asn Asp Thr Phe Ala Ser Ala Ser Arg Ser Asp Lys Cys Ile Pro Pro
                 85                  90                  95

Pro Arg Gly Leu Leu Glu Arg Asn Leu Asp Ser Pro Ile Met Pro Lys
             100                 105                 110

Glu Val Glu Pro Glu Arg Arg Met Leu Arg Pro Arg Thr Arg Arg Ser
         115                 120                 125

Ser Arg His His Asp Ser Asp Ser Gly Leu Gly Ser Ser Ile Ala Ser
 130                 135                 140

Thr Ser Glu Lys Asp Ala Ser Ser Lys Ala Lys Thr Thr Arg Thr Ser
145                 150                 155                 160

Ala Val Ala Arg Ser Ala Thr Ala Arg Ala Ala Ser Thr Pro Asp Leu
                 165                 170                 175

Pro Gly Leu Gly Asp Arg Ala Thr Asn Arg Ile Val Glu Tyr Ile Leu
             180                 185                 190

Lys Pro Leu Leu Ala Lys Pro Asn Leu Lys Glu Phe His Ser Leu Val
         195                 200                 205

Leu Glu Cys Pro Lys Lys Ile Gln Glu Lys Glu Ile Leu Cys Leu Arg
 210                 215                 220

Asp Leu Glu Lys Thr Leu Ile Leu Val Ala Pro Ala Thr Val Gln His
225                 230                 235                 240

Leu Gly Asp Arg Glu Leu Thr Arg Pro Arg Asp Leu Pro Tyr Thr Ser
                 245                 250                 255

Gly Tyr Phe Val Asp Leu Val Asp Gln Phe Tyr Asn Tyr Ala Arg Gln
             260                 265                 270

Ile Ala Glu Ser Asn Lys Thr Lys Glu Gly Ala Asn Asp Met Asp Ile
         275                 280                 285

Asp Pro Thr Asp Gln Ile Lys Ile His Gly Gly Pro His Ile Asn Gly
 290                 295                 300

Arg Leu Ser Glu Leu Val Arg Val Lys Lys Asn Gly Gln Ala Ile Ser
305                 310                 315                 320

Leu Ala Thr Gly Leu Pro Val Asp Leu Cys Asp Lys Ala Pro Glu Thr
                 325                 330                 335

Pro Val Asn Phe Lys Arg Ser Gln Ser Glu Glu Ala Leu Asp Glu Glu
             340                 345                 350

Glu Val Met Arg Ser Met Ala Arg Arg Lys Lys Asn Ala Ser Pro Glu
         355                 360                 365

Glu Leu Ala Pro Lys Arg Cys Arg Glu Pro Gly Cys Asn Lys Glu Phe
 370                 375                 380

Lys Arg Pro Cys Asp Leu Thr Lys His Glu Lys Thr His Ser Arg Pro
385                 390                 395                 400

Trp Lys Cys Pro Val Lys Thr Cys Lys Tyr His Glu Tyr Gly Trp Pro
                 405                 410                 415

Thr Glu Lys Glu Met Asp Arg His His Asn Asp Lys His Ser Ser Ala
             420                 425                 430
```

Pro Pro Met Tyr Glu Cys Leu Phe Lys Pro Cys Pro Tyr Lys Ser Lys
        435                 440                 445

Arg Glu Ser Asn Cys Lys Gln His Met Glu Lys Ala His Gly Trp Thr
    450                 455                 460

Tyr Val Arg Thr Lys Thr Asn Gly Lys Lys Pro Ser Thr Leu Pro Ser
465                 470                 475                 480

Leu Gly Pro Asp Ser Gly His Pro Thr Pro Gln Leu Gln Asn Ile Gly
            485                 490                 495

Thr Pro Ser Ser Asp Arg Ser Met Ser Ile Ala Thr Pro Ser Asp Asp
        500                 505                 510

Trp Asn Ala Gly Leu Tyr Gln Thr Asn Ile Glu Phe Pro Ala Tyr Ala
    515                 520                 525

Pro Glu Phe Asn Phe Asn Thr Ile Pro Gln Gln Leu Glu Leu Asp Tyr
530                 535                 540

Ser Pro Ile Asp Asn Gly Thr Pro Ser Pro Asp Ser Gly Met Asp His
545                 550                 555                 560

Asn Ser Ala Tyr Gln Asp Leu Asn Glu Phe Thr Leu Ile Asp Asp Ile
            565                 570                 575

Tyr Gly Ala Thr Val Gln Leu Pro Asn Gln Val Ile Ser Pro Phe Tyr
        580                 585                 590

Leu Lys Asp Met Gly Gln His Leu Gly Ala Tyr Thr Ala Pro Asp Leu
    595                 600                 605

Cys Gln Pro His Pro Ala His Ile Ser Pro Ile Gly Gln Gly Asn Thr
610                 615                 620

Met Leu Phe Thr Pro Pro Thr Ser Leu Gly Glu Val Asp Glu Gly Phe
625                 630                 635                 640

Glu Asp His Asp Phe Ala Met Ser Asn Cys Asn Asn Val Pro Gly Asp
            645                 650                 655

Phe Ile Leu Tyr Pro Pro Thr Thr Asp Ala Tyr Ser Lys Pro Thr Phe
        660                 665                 670

Thr Glu Ser Leu Phe Ala Asn Val Asp Ile Pro Ser Met Ala Ala Gly
    675                 680                 685

Tyr Ser Gln Pro Ser Ser Gln Asp Ile Leu His Ala Tyr Gln Gly Asp
690                 695                 700

Trp Thr Ser His Asp Met Asn Ala Tyr Phe
705                 710

<210> SEQ ID NO 18
<211> LENGTH: 2145
<212> TYPE: DNA
<213> ORGANISM: Neurospora crassa

<400> SEQUENCE: 18
atgtcgaacc ctcgcaggag accggcgggt ggattgaccc tcaagacgaa catgctccta    60
caaaagggag ctaccttcca ctctcccact actccagcct cggggggattc ttctgagcgc   120 gtcttcgtcc cgccgtcgct ccctcgccgc tcccacacca acttggacga tgttatcgac   180
tcccgctgcc gccgcgttgc cttagctttg gatgcgatcg agaggcaatt ggcctcttca   240
aatgacacct tgcctcggc tagtcgcagt gacaagtgca ttccccccgcc acgtgggctg    300 ctggaaagaa acttggattc gcctatcatg cccaaggagg ttgagcctga gcgccggatg    360
ctccgtccac ggacacgccg ttcatctcgg caccacgatt cagacagcgg tctaggaagc    420
tcgattgctt ctacttccga gaaggatgcc tcttccaagg ccaagacgac gaggacttcg    480
gctgtcgcca gatccgctac cgcccgcgca gcatcgacac ctgatcttcc gggccttggg   540

```
gaccgtgcta ccaaccgcat cgttgaatac attttgaagc ctctgcttgc aaagccgaat      600
ctgaaagagt ttcactcgct tgtgcttgag tgtcccaaaa agatccagga gaaggagatc      660
ttgtgcctaa gagatcttga aagactttg atcctcgtgg ctccggcaac tgtccagcac       720
cttggcgacc gcgagctgac tcgccctcgc gatctccctt acactagcgg ttattttgtt      780
gatctcgttg atcaattcta taactatgcc cggcagatcg cggaaagcaa caagaccaag      840
gaaggcgcca atgacatgga tattgatccc actgatcaaa tcaagataca cggtggccct      900
cacatcaacg gcaggctttc ggaactggtc cgcgtgaaga gaacggaca ggccatctcc       960 ttggctactg gattgcctgt ggacctttgt gataaggcgc cagaaacccc ggtaaacttc      1020
aagcgctccc agagcgagga ggccctggat gaagaggagg ttatgcgctc catggctcgc     1080
cggaagaaga acgccagccc tgaggagctg gcgccgaaga gatgccgcga gcctggttgc     1140
aacaaggagt tcaagcgccc ttgtgacctg accaagcacg agaagacaca ttctagacca     1200
tggaagtgcc cggtcaagac atgcaagtac acgagtacg gctggcccac cgagaaggaa      1260
atggatcgtc atcacaacga caagcactcc tcagccccac ctatgtacga gtgcctcttc     1320
aagccttgcc cctacaagtc caagcgcgag tccaactgca gcagcatat ggaaaaggcc      1380 catggctgga cgtacgttag gactaaaacc aatggcaaga agcccagtac gcttcccagc     1440
ttggggcccg attccggcca tcccactccc cagctgcaga acattggtac ccttcgagc      1500 gaccgcagta tgagcatcgc cactccctcc gatgattgga acgctgggct gtaccagacc     1560
aacattgagt tccctgcata tgctcccgag ttcaacttca acaccatccc gcagcagctt     1620
gagcttgact attcacccat tgacaacggc actccatcac cggattctgg catggaccac     1680
aattctgcgt atcaagatct caacgaattc acgctcattg atgacatcta cggtgcgact     1740
gtgcaactgc ccaaccaagt catttctccc ttctacctca aagacatggg acagcatctc     1800
ggcgcgtaca ccgcgcccga cctttgccag ccacatcccg cccatatttc ccccattggg     1860
caaggaaaca cgatgctttt cacgcccct acttcattgg gggaagttga tgagggctt      1920 gaggatcacg attttgccat gagtaactgc aataatgtcc ctggagactt cattttgtat    1980
cctccaacca ctgacgccta ctcaaaaccc acgttcactg aatcacttttt cgcgaacgtg    2040 gacatcccga gcatggctgc cggctattcc cagccatcat ctcaggacat cttgcacgcc     2100
tatcaaggtg attggacttc gcatgatatg aatgcttact tctaa                     2145
```

<210> SEQ ID NO 19
<211> LENGTH: 619
<212> TYPE: PRT
<213> ORGANISM: Neurospora crassa

<400> SEQUENCE: 19

Met Lys Phe Leu Gly Ile Ala Ala Leu Val Ala Gly Leu Leu Ala Pro
1               5                   10                  15

Ser Leu Val Leu Gly Ala Pro Ala Pro Gly Thr Glu Gly Val Asn Leu
            20                  25                  30

Leu Thr Pro Val Asp Lys Arg Gln Asp Ser Gln Ala Glu Arg Tyr Gly
        35                  40                  45

Gly Gly Gly Gly Gly Cys Asn Ser Pro Thr Asn Arg Gln Cys Trp
    50                  55                  60

Ser Pro Gly Phe Asn Ile Asn Thr Asp Tyr Glu Leu Gly Thr Pro Asn
65                  70                  75                  80

Thr Gly Lys Thr Arg Arg Tyr Lys Leu Thr Leu Thr Glu Thr Asp Asn

```
                85                  90                  95
Trp Ile Gly Pro Asp Gly Val Ile Lys Asp Lys Val Met Met Val Asn
            100                 105                 110
Asp Lys Ile Ile Gly Pro Thr Ile Gln Ala Asp Trp Gly Asp Tyr Ile
            115                 120                 125
Glu Ile Thr Val Ile Asn Lys Leu Lys Ser Asn Gly Thr Ser Ile His
            130                 135                 140
Trp His Gly Met His Gln Arg Asn Ser Asn Ile Gln Asp Gly Val Asn
145                 150                 155                 160
Gly Val Thr Glu Cys Pro Ile Pro Arg Gly Gly Ser Lys Val Tyr
                165                 170                 175
Arg Trp Arg Ala Thr Gln Tyr Gly Thr Ser Trp Tyr His Ser His Phe
                180                 185                 190
Ser Ala Gln Tyr Gly Asn Gly Ile Val Gly Pro Ile Val Ile Asn Gly
                195                 200                 205
Pro Ala Ser Ala Asn Tyr Asp Val Asp Leu Gly Pro Phe Pro Leu Thr
            210                 215                 220
Asp Tyr Tyr Asp Thr Ala Asp Arg Leu Val Leu Leu Thr Gln His
225                 230                 235                 240
Ala Gly Pro Pro Ser Asn Asn Val Leu Phe Asn Gly Phe Ala Lys
                245                 250                 255
His Pro Thr Thr Gly Ala Gly Gln Tyr Ala Thr Val Ser Leu Thr Lys
                260                 265                 270
Gly Lys Lys His Arg Leu Arg Leu Ile Asn Thr Ser Val Glu Asn His
                275                 280                 285
Phe Gln Leu Ser Leu Val Asn His Ser Met Thr Ile Ile Ser Ala Asp
            290                 295                 300
Leu Val Pro Val Gln Pro Tyr Lys Val Asp Ser Leu Phe Leu Gly Val
305                 310                 315                 320
Gly Gln Arg Tyr Asp Val Ile Ile Asp Ala Asn Gln Ala Val Gly Asn
                325                 330                 335
Tyr Trp Phe Asn Val Thr Phe Gly Gly Ser Lys Leu Cys Gly Asp Ser
                340                 345                 350
Asp Asn His Tyr Pro Ala Ala Ile Phe Arg Tyr Gln Gly Ala Pro Lys
                355                 360                 365
Ala Leu Pro Thr Asn Gln Gly Val Ala Pro Val Asp His Gln Cys Leu
            370                 375                 380
Asp Leu Asn Asp Leu Lys Pro Val Leu Gln Arg Ser Leu Asn Thr Asn
385                 390                 395                 400
Ser Ile Ala Leu Asn Thr Gly Asn Thr Ile Pro Ile Thr Leu Asp Gly
                405                 410                 415
Phe Val Trp Arg Val Asn Gly Thr Ala Ile Asn Ile Asn Trp Asn Lys
                420                 425                 430
Pro Val Leu Glu Tyr Val Leu Thr Gly Asn Thr Asn Tyr Ser Gln Ser
                435                 440                 445
Asp Asn Ile Val Gln Val Glu Gly Val Asn Gln Trp Lys Tyr Trp Leu
            450                 455                 460
Ile Glu Asn Asp Pro Asp Gly Ala Phe Ser Leu Pro His Pro Ile His
465                 470                 475                 480
Leu His Gly His Asp Phe Leu Ile Leu Gly Arg Ser Pro Asp Val Thr
                485                 490                 495
Ala Ile Ser Gln Thr Arg Tyr Val Phe Asp Pro Ala Val Asp Met Ala
                500                 505                 510
```

```
Arg Leu Asn Gly Asn Asn Pro Thr Arg Arg Asp Thr Ala Met Leu Pro
        515                 520                 525

Ala Lys Gly Trp Leu Leu Ile Ala Phe Arg Thr Asp Asn Pro Gly Ser
    530                 535                 540

Trp Leu Met His Cys His Ile Ala Trp His Val Ser Gly Gly Leu Ser
545                 550                 555                 560

Asn Gln Phe Leu Glu Arg Ala Gln Asp Leu Arg Asn Ser Ile Ser Pro
            565                 570                 575

Ala Asp Lys Lys Ala Phe Asn Asp Asn Cys Asp Ala Trp Arg Ala Tyr
        580                 585                 590

Phe Pro Asp Asn Ala Pro Phe Pro Lys Asp Asp Ser Gly Leu Arg Ser
            595                 600                 605

Gly Val Lys Ala Arg Glu Val Lys Met Lys Trp
        610                 615

<210> SEQ ID NO 20
<211> LENGTH: 1860
<212> TYPE: DNA
<213> ORGANISM: Neurospora crassa

<400> SEQUENCE: 20
atgaaattct tgggcattgc cgccctcgtt gcgggccttc ttgccccttc acttgttctc      60
ggtgctcctg cacctggcac cgagggagtg aatctcctca ctcccgttga taagagacag     120
gactcccaag ccgaacgtta tggaggtggc ggaggggtg gttgcaactc cccgaccaac      180
cggcagtgtt ggtctccagg attcaacatc aacaccgact atgaactcgg aactcctaat     240
accggcaaga ccagacggta caagctcacc ctcaccgaga ctgataactg gattggccct     300
gatggtgtca taaaggacaa ggtcatgatg gtcaacgaca gatcattgg acctaccatt      360
caggctgatt ggggcgacta tattgagatc accgtcatca acaaactgaa gtcgaatggc     420
acctcgatcc actggcacgg catgcaccag cgcaactcta acatccagga cggcgtcaac     480
ggcgtgaccg agtgccccat cccacccaga ggcggcagca agtgtaccg ctggcgggcc      540
acccagtacg gaacgtcgtg gtaccactcg catttctcag cgcagtacgg caatggcatt     600
gttgggccca ttgtcatcaa cggaccggcc tcggccaact acgacgtcga cctcggccct     660
ttcccgctca cggactacta ttacgacacc gctgaccgtc tcgtgctgct cacacagcat     720
gccggccctc cgccgagcaa taatgtgctc ttcaacggct cgccaagca tccgaccaca      780
ggcgctggcc agtatgccac cgtgtcgctc accaagggta agaagcatcg gctgcggctc     840
atcaacacct cggtcgagaa tcacttccaa ctgtcgctgg tgaatcactc catgaccatc     900
atctcggcgg atctggttcc cgtacagccc tacaaggtcg acagcctgtt cctcggcgtc     960
ggtcagcgct acgatgtcat catcgacgcc aaccaggccg ttggaaacta ctggttcaat    1020
gtgacgtttg tgggagcaa gctgtgcggt gattcggaca ccactaccc ggccgccatt      1080
ttccggtacc agggcgcgcc gaaggcactg ccgaccaacc agggcgttgc gccggtcgac    1140
caccaatgcc tggacctcaa cgacctgaag cccgtcctgc agcgcagcct gaacaccaac    1200
agcatcgcac tcaacactgg caacacgatc cccatcacgc tcgacgggtt cgtctggcgg    1260
gtcaatggaa cggccatcaa catcaactgg aacaagccgg tgctggagta cgtgctgacg    1320
ggcaacacca actactcgca gtccgacaac attgtgcagg tcgagggcgt caaccaatgg    1380
aagtactggc tcatcgagaa cgaccccgac ggtgccttta gctgccgca tcccatccac     1440
ctgcacggcc acgactttct catcctcggt cggtcgcccg acgtgaccgc catcagccag    1500
```

```
acgcgctacg tgtttgaccc ggccgtggac atggctcggt tgaacggcaa caacccgacg   1560
cggcgcgaca cggccatgct cccggccaag ggctggctgc tcatcgcgtt ccgcaccgac   1620
aatcccgggt cgtggctgat gcactgccac attgcctggc acgtgtcggg aggtctgtcg   1680
aaccagttcc tggagcgggc gcaggacctc agaaacagta tcagccctgc ggataagaag   1740
gcctttaacg acaactgtga cgcgtggagg gcgtacttcc ctgacaatgc gccgttcccc   1800
aaggacgact ctggcctgag gagcggtgtc aaggcgaggg aggtgaagat gaagtggtag   1860
```

<210> SEQ ID NO 21
<211> LENGTH: 829
<212> TYPE: PRT
<213> ORGANISM: Neurospora crassa

<400> SEQUENCE: 21

Met Arg Thr Thr Ser Ala Phe Leu Ser Gly Leu Ala Ala Val Ala Ser
1               5                   10                  15

Leu Leu Ser Pro Ala Phe Ala Gln Thr Ala Pro Lys Thr Phe Thr His
            20                  25                  30

Pro Asp Thr Gly Ile Val Phe Asn Thr Trp Ser Ala Ser Asp Ser Gln
        35                  40                  45

Thr Lys Gly Gly Phe Thr Val Gly Met Ala Leu Pro Ser Asn Ala Leu
    50                  55                  60

Thr Thr Asp Ala Thr Glu Phe Ile Gly Tyr Leu Glu Cys Ser Ser Ala
65                  70                  75                  80

Lys Asn Gly Ala Asn Ser Gly Trp Cys Gly Val Ser Leu Arg Gly Ala
                85                  90                  95

Met Thr Asn Asn Leu Leu Ile Thr Ala Trp Pro Ser Asp Gly Glu Val
            100                 105                 110

Tyr Thr Asn Leu Met Phe Ala Thr Gly Tyr Ala Met Pro Lys Asn Tyr
        115                 120                 125

Ala Gly Asp Ala Lys Ile Thr Gln Ile Ala Ser Ser Val Asn Ala Thr
    130                 135                 140

His Phe Thr Leu Val Phe Arg Cys Gln Asn Cys Leu Ser Trp Asp Gln
145                 150                 155                 160

Asp Gly Val Thr Gly Gly Ile Ser Thr Ser Asn Lys Gly Ala Gln Leu
                165                 170                 175

Gly Trp Val Gln Ala Phe Pro Ser Pro Gly Asn Pro Thr Cys Pro Thr
            180                 185                 190

Gln Ile Thr Leu Ser Gln His Asp Asn Gly Met Gly Gln Trp Gly Ala
        195                 200                 205

Ala Phe Asp Ser Asn Ile Ala Asn Pro Ser Tyr Thr Ala Trp Ala Ala
    210                 215                 220

Lys Ala Thr Lys Thr Val Thr Gly Thr Cys Ser Gly Pro Val Thr Thr
225                 230                 235                 240

Ser Ile Ala Ala Thr Pro Val Pro Thr Gly Val Ser Phe Asp Tyr Ile
                245                 250                 255

Val Val Gly Gly Gly Ala Gly Gly Ile Pro Val Ala Asp Lys Leu Ser
            260                 265                 270

Glu Ser Gly Lys Ser Val Leu Leu Ile Glu Lys Gly Phe Ala Ser Thr
        275                 280                 285

Gly Glu His Gly Gly Thr Leu Lys Pro Glu Trp Leu Asn Asn Thr Ser
    290                 295                 300

Leu Thr Arg Phe Asp Val Pro Gly Leu Cys Asn Gln Ile Trp Lys Asp

-continued

```
            305                 310                 315                 320
Ser Asp Gly Ile Ala Cys Ser Asp Thr Asp Gln Met Ala Gly Cys Val
                    325                 330                 335
Leu Gly Gly Gly Thr Ala Ile Asn Ala Gly Leu Trp Tyr Lys Pro Tyr
                    340                 345                 350
Thr Lys Asp Trp Asp Tyr Leu Phe Pro Ser Gly Trp Lys Gly Ser Asp
                    355                 360                 365
Ile Ala Gly Ala Thr Ser Arg Ala Leu Ser Arg Ile Pro Gly Thr Thr
            370                 375                 380
Thr Pro Ser Gln Asp Gly Lys Arg Tyr Leu Gln Gln Gly Phe Glu Val
385                 390                 395                 400
Leu Ala Asn Gly Leu Lys Ala Ser Gly Trp Lys Glu Val Asp Ser Leu
                    405                 410                 415
Lys Asp Ser Glu Gln Lys Asn Arg Thr Phe Ser His Thr Ser Tyr Met
                    420                 425                 430
Tyr Ile Asn Gly Glu Arg Gly Gly Pro Leu Ala Thr Tyr Leu Val Ser
            435                 440                 445
Ala Lys Lys Arg Ser Asn Phe Lys Leu Trp Leu Asn Thr Ala Val Lys
            450                 455                 460
Arg Val Ile Arg Glu Gly Gly His Ile Thr Gly Val Glu Val Glu Ala
465                 470                 475                 480
Phe Arg Asn Gly Gly Tyr Ser Gly Ile Ile Pro Val Thr Asn Thr Thr
                    485                 490                 495
Gly Arg Val Val Leu Ser Ala Gly Thr Phe Gly Ser Ala Lys Ile Leu
                    500                 505                 510
Leu Arg Ser Gly Ile Gly Pro Lys Asp Gln Leu Glu Val Val Lys Ala
            515                 520                 525
Ser Ala Asp Gly Pro Thr Met Val Ser Asn Ser Ser Trp Ile Asp Leu
            530                 535                 540
Pro Val Gly His Asn Leu Val Asp His Thr Asn Thr Asp Thr Val Ile
545                 550                 555                 560
Gln His Asn Asn Val Thr Phe Tyr Asp Phe Tyr Lys Ala Trp Asp Asn
                    565                 570                 575
Pro Asn Thr Thr Asp Met Asn Leu Tyr Leu Asn Gly Arg Ser Gly Ile
                    580                 585                 590
Phe Ala Gln Ala Ala Pro Asn Ile Gly Pro Leu Phe Trp Glu Glu Ile
            595                 600                 605
Thr Gly Ala Asp Gly Ile Val Arg Gln Leu His Trp Thr Ala Arg Val
            610                 615                 620
Glu Gly Ser Phe Glu Thr Pro Asp Gly Tyr Ala Met Thr Met Ser Gln
625                 630                 635                 640
Tyr Leu Gly Arg Gly Ala Thr Ser Arg Gly Arg Met Thr Leu Ser Pro
                    645                 650                 655
Thr Leu Asn Thr Val Val Ser Asp Leu Pro Tyr Leu Lys Asp Pro Asn
                    660                 665                 670
Asp Lys Ala Ala Val Val Gln Gly Ile Val Asn Leu Gln Lys Ala Leu
            675                 680                 685
Ala Asn Val Lys Gly Leu Thr Trp Ala Tyr Pro Ser Ala Asn Gln Thr
            690                 695                 700
Ala Ala Asp Phe Val Asp Lys Gln Pro Val Thr Tyr Gln Ser Arg Arg
705                 710                 715                 720
Ser Asn His Trp Met Gly Thr Asn Lys Met Gly Thr Asp Asp Gly Arg
                    725                 730                 735
```

```
Ser Gly Gly Thr Ala Val Val Asp Thr Asn Thr Arg Val Tyr Gly Thr
            740                 745                 750

Asp Asn Leu Tyr Val Val Asp Ala Ser Ile Phe Pro Gly Val Pro Thr
        755                 760                 765

Thr Asn Pro Thr Ala Tyr Ile Val Val Ala Ala Glu His Ala Ala Ala
    770                 775                 780

Lys Ile Leu Ala Gln Pro Ala Asn Glu Ala Val Pro Lys Trp Gly Trp
785                 790                 795                 800

Cys Gly Gly Pro Thr Tyr Thr Gly Ser Gln Thr Cys Gln Ala Pro Tyr
                805                 810                 815

Lys Cys Glu Lys Gln Asn Asp Trp Tyr Trp Gln Cys Val
            820                 825

<210> SEQ ID NO 22
<211> LENGTH: 2490
<212> TYPE: DNA
<213> ORGANISM: Neurospora crassa

<400> SEQUENCE: 22
```

| | | | | |
|---|---|---|---|---|
| atgaggacca cctcggcctt tctcagcggc ctggcggcgg tggcttcatt gctgtcgccc | | | | 60 |
| gccttcgccc aaaccgctcc caagaccttc actcatcctg ataccggcat tgtcttcaac | | | | 120 |
| acatggagtg cttccgattc ccagaccaaa ggtggcttca ctgttggtat ggctctgccg | | | | 180 |
| tcaaatgctc ttactaccga cgcgactgaa ttcatcggtt atctggaatg ctcctccgcc | | | | 240 |
| aagaatggtg ccaatagcgg ttggtgcggt gtttctctca gaggcgccat gaccaacaat | | | | 300 |
| ctactcatta ccgcctggcc ttctgacgga gaagtctaca ccaatctcat gttcgccacg | | | | 360 |
| ggttacgcca tgcccaagaa ctacgctggt gacgccaaga tcacccagat cgcgtccagc | | | | 420 |
| gtgaacgcta cccacttcac ccttgtcttt aggtgccaga actgtttgtc atgggaccaa | | | | 480 |
| gacggtgtca ccggcggcat ttctaccagc aataagggg cccagctcgg ttgggtccag | | | | 540 |
| gcgttcccct ctcccggcaa cccgacttgc cctacccaga tcactctcag tcagcatgac | | | | 600 |
| aacggtatgg ccagtggggg agctgccttt gacagcaaca ttgccaatcc ctcttatact | | | | 660 |
| gcatgggctg ccaaggccac caagaccgtt accggtactt gcagtggtcc agtcacgacc | | | | 720 |
| agtattgccg ccactcctgt tcccactggc gtttcttttg actacattgt cgttggtggt | | | | 780 |
| ggtgccggtg gtattcccgt cgctgacaag ctcagcgagt ccggtaagag cgtgctgctc | | | | 840 |
| atcgagaagg gtttcgcttc cactggtgag catggtggta ctctgaagcc cgagtggctg | | | | 900 |
| aataatacat cccttactcg cttcgatgtt cccggtcttt gcaaccagat ctggaaagac | | | | 960 |
| tcggatggca ttgcctgctc cgataccgat cagatggccg gctgcgtgct cggcggtggt | | | | 1020 |
| accgccatca cgccggtctc tggtacaag ccctacacca aggactggga ctacctcttc | | | | 1080 |
| ccctctggct ggaagggcag cgatatcgcc ggtgctacca gcagagccct ctcccgcatt | | | | 1140 |
| ccgggtacca ccactccttc tcaggatgga aagcgctacc ttcagcaggg tttcgaggtt | | | | 1200 |
| cttgccaacg gcctcaaggc gagcggctgg aaggaggtcg attccctcaa ggacagcgag | | | | 1260 |
| cagaagaacc gcactttctc ccacacctca tacatgtaca tcaatggcga gcgtggcggt | | | | 1320 |
| cctctagcga cttacctcgt cagcgccaag aagcgcagca acttcaagct gtggctcaac | | | | 1380 |
| accgctgtca agcgcgtcat ccgtgagggc ggccacatta ccggtgtgga ggttgaggcc | | | | 1440 |
| ttccgcaacg gcggctactc cggaatcatc ccgtcacca acaccaccgg ccgcgtcgtt | | | | 1500 |
| ctttccgccg gcaccttcgg cagcgccaag atccttctcc gttccggcat tggccccaag | | | | 1560 |

-continued

```
gaccagctcg aggtggtcaa ggcctccgcc gacggccta ccatggtcag caactcgtcc   1620
tggattgacc tccccgtcgg ccacaacctg gttgaccaca ccaacaccga caccgtcatc   1680
cagcacaaca acgtgacctt ctacgactt tacaaggctt gggacaaccc caacacgacc   1740
gacatgaacc tgtacctcaa tgggcgctcc ggcatcttcg cccaggccgc gcccaacatt   1800
ggccccttgt tctgggagga gatcacgggc gccgacggca tcgtccgtca gctgcactgg   1860
accgcccgcg tcgagggcag cttcgagacc cccgacggct acgccatgac catgagccag   1920
taccttggcc gtggcgccac ctcgcgcggc cgcatgaccc tcagccctac cctcaacacc   1980
gtcgtgtctg acctcccgta cctcaaggac cccaacgaca aggccgctgt cgttcagggt   2040
atcgtcaacc tccagaaggc tctcgccaac gtcaagggtc tcacctgggc ttaccctagc   2100
gccaaccaga cggctgctga ttttgttgac aagcaacccg taacctacca atcccgccgc   2160
tccaaccact ggatgggcac caacaagatg gcaccgacg acggccgcag cggcggcacc   2220
gcagtcgtcg acaccaacac gcgcgtctat ggcaccgaca acctgtacgt ggtggacgcc   2280
tcgattttcc ccggtgtgcc gaccaccaac cctaccgcct acattgtcgt cgccgctgag   2340
catgccgcgg ccaaaatcct ggcgcaaccc gccaacgagg ccgttcccaa gtggggctgg   2400
tgcggcgggc cgacgtatac tggcagccag acgtgccagg cgccatataa gtgcgagaag   2460
cagaatgatt ggtattggca gtgtgtgtag                                   2490
```

<210> SEQ ID NO 23
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Leu, Ile,Val, Met, Phe, Ser, Thr, or Cys
<220> FEATURE:
<221> NAME/KEY: VARIANT
<222> LOCATION: 2
<223> OTHER INFORMATION: Xaa = Leu, Ile, Val, Phe, Tyr, or Ser
<220> FEATURE:
<221> NAME/KEY: VARIANT
<222> LOCATION: 3
<223> OTHER INFORMATION: Xaa = Leu, Ile, or Val
<220> FEATURE:
<221> NAME/KEY: VARIANT
<222> LOCATION: 4
<223> OTHER INFORMATION: Xaa = Leu, Ile, Val, Met, Ser, or Thr
<220> FEATURE:
<221> NAME/KEY: VARIANT
<222> LOCATION: 8
<223> OTHER INFORMATION: Xaa = Leu, Ile, Val, Met, Phe, Ala, or Arg
<220> FEATURE:
<221> NAME/KEY: VARIANT
<222> LOCATION: 9
<223> OTHER INFORMATION: Xaa = Cys, Ser, Ala, Gly, or Asn

<400> SEQUENCE: 23

Xaa Xaa Xaa Xaa Glu Asn Gly Xaa Xaa
1               5

<210> SEQ ID NO 24
<211> LENGTH: 18
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2

```
<223> OTHER INFORMATION: Xaa = Leu, Ile, Val,or Met
<220> FEATURE:
<221> NAME/KEY: VARIANT
<222> LOCATION: 3
<223> OTHER INFORMATION: Xaa = Lys, or Arg
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 5
<223> OTHER INFORMATION: Xaa = Glu, Gln, Lys, Arg, or Asp
<220> FEATURE:
<221> NAME/KEY: VARIANT
<222> LOCATION: 6, 7, 8, 9
<223> OTHER INFORMATION: Xaa = Any Amino Acid
<220> FEATURE:
<221> NAME/KEY: VARIANT
<222> LOCATION: 11
<223> OTHER INFORMATION: Xaa = Leu, Ile, Val, Met, Phe, Thr, or Cys
<220> FEATURE:
<221> NAME/KEY: VARIANT
<222> LOCATION: 12
<223> OTHER INFORMATION: Xaa = Leu, Ile, Val, or Thr
<220> FEATURE:
<221> NAME/KEY: VARIANT
<222> LOCATION: 13
<223> OTHER INFORMATION: Xaa = Leu, Ile, Val, Met, or Phe
<220> FEATURE:
<221> NAME/KEY: VARIANT
<222> LOCATION: 14
<223> OTHER INFORMATION: Xaa = Ser, or Thr
<220> FEATURE:
<221> NAME/KEY: VARIANT
<222> LOCATION: 16, 17
<223> OTHER INFORMATION: Xaa = Any Amino Acid
<220> FEATURE:
<221> NAME/KEY: VARIANT
<222> LOCATION: 18
<223> OTHER INFORMATION: Xaa = Ser, Gly, Ala, Asp, Asn, Ile, or Thr

<400> SEQUENCE: 24

Xaa Xaa Xaa Xaa Xaa Xaa Xaa Xaa Xaa Gly Xaa Xaa Xaa Xaa Asp Xaa
1               5                   10                  15

Xaa Xaa
```